(12) United States Patent
Munn et al.

(10) Patent No.: US 7,598,287 B2
(45) Date of Patent: Oct. 6, 2009

(54) USE OF INHIBITORS OF INDOLEAMINE-2,3-DIOXYGENASE IN COMBINATION WITH OTHER THERAPEUTIC MODALITIES

(75) Inventors: David Munn, Augusta, GA (US); Andrew Mellor, Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 662 days.

(21) Appl. No.: 10/780,797

(22) Filed: Feb. 17, 2004

(65) Prior Publication Data

US 2004/0234623 A1  Nov. 25, 2004

Related U.S. Application Data

(60) Provisional application No. 60/538,647, filed on Jan. 22, 2004, provisional application No. 60/459,489, filed on Apr. 1, 2003.

(51) Int. Cl.
*A61K 31/40* (2006.01)
(52) U.S. Cl. ..................................................... 514/419
(58) Field of Classification Search ................... 514/419
See application file for complete search history.

(56) References Cited

U.S. PATENT DOCUMENTS

| | | | |
|---|---|---|---|
| 4,244,946 A | 1/1981 | Rivier et al. |
| 4,305,872 A | 12/1981 | Johnston et al. |
| 4,316,891 A | 2/1982 | Guillemin et al. |
| 4,629,784 A | 12/1986 | Stammer |
| 4,792,525 A | 12/1988 | Ruoslahti et al. |
| 4,868,116 A | 9/1989 | Morgan et al. |
| 4,980,286 A | 12/1990 | Morgan et al. |
| 5,244,807 A | 9/1993 | Murtfeldt et al. |
| 5,478,556 A | 12/1995 | Elliott et al. |
| 5,723,325 A | 3/1998 | Murtfeldt et al. |
| 5,837,231 A | 11/1998 | Low et al. |
| 5,861,159 A | 1/1999 | Pardoll et al. |
| 5,874,560 A | 2/1999 | Kawakami et al. |
| 6,251,399 B1 | 6/2001 | Diamond et al. |
| 6,395,876 B1 | 5/2002 | Munn et al. |
| 6,451,840 B1 | 9/2002 | Munn et al. |
| 6,482,416 B2 | 11/2002 | Munn et al. |
| 7,098,209 B2 | 8/2006 | Orme et al. |
| 7,160,539 B2 | 1/2007 | Munn et al. |
| 2002/0114784 A1 | 8/2002 | Li et al. |
| 2002/0155104 A1 | 10/2002 | Munn et al. |
| 2003/0194803 A1 | 10/2003 | Mellor et al. |
| 2004/0152705 A1 | 8/2004 | Orme et al. |
| 2004/0161425 A1 | 8/2004 | Munn et al. |
| 2004/0234623 A1 | 11/2004 | Munn et al. |
| 2005/0142078 A1 | 6/2005 | Dorr et al. |
| 2005/0186289 A1 | 8/2005 | Munn et al. |
| 2006/0292618 A1 | 12/2006 | Mellor et al. |
| 2007/0048769 A1 | 3/2007 | Mellor et al. |
| 2007/0077234 A1 | 4/2007 | Munn et al. |
| 2007/0099844 A1 | 5/2007 | Prendergast et al. |
| 2007/0105907 A1 | 5/2007 | Prendergast et al. |
| 2007/0173524 A1 | 7/2007 | Prendergast et al. |

FOREIGN PATENT DOCUMENTS

| | | |
|---|---|---|
| AU | 2003206496 A1 | 9/2003 |
| AU | 2002307243 A1 | 10/2003 |
| AU | 2003267088 A1 | 4/2004 |
| AU | 2003206496 B2 | 8/2007 |
| AU | 2002307243 B2 | 1/2008 |
| CA | 2445625 A1 | 12/2002 |
| CA | 2475985 A1 | 9/2003 |
| CA | 2483451 A1 | 10/2003 |
| EP | 0 385 385 A2 | 9/1990 |
| EP | 1 392 688 A1 | 6/2008 |
| JP | 2004532889 T2 | 10/2004 |
| JP | 2005524652 T2 | 8/2005 |
| MX | 3011082 A | 6/2004 |
| WO | WO 93/01286 | 1/1993 |
| WO | 99/29310 | 6/1999 |
| WO | 99/29852 | 6/1999 |
| WO | 00/66764 | * 11/2000 |
| WO | WO 02/98877 A1 | 12/2002 |
| WO | WO 03/072072 A1 | 9/2003 |
| WO | WO 03/087347 A1 | 10/2003 |
| WO | WO 2004/024075 A2 | 3/2004 |
| WO | WO 2004/024075 A3 | 10/2004 |
| WO | WO 2004/093871 A1 | 11/2004 |
| WO | WO 2004/094409 A1 | 11/2004 |
| WO | WO 2007/050405 A2 | 5/2007 |
| WO | WO 2007/081878 A2 | 7/2007 |

OTHER PUBLICATIONS

Gura et al;. System for identifying new drugs are often faulty. Science, 1997, 278:1041-1042.*

Johnson et al. Relationships between drug activity in NCI preclinical in vitro and in vivo models and early clinical trials. British J. of Cancer, 2001, 84(10):1424-1431.*

Muller et al. Indoleamine 2,3-dioxygenase in cancer: targeting pathological immune tolerance with small-molecule inhibitors. Expert Opin. Ther. Targets, 2005, vol. 9, No. 4, pp. 831-849.*

(Continued)

*Primary Examiner*—Ardin Marschel
*Assistant Examiner*—James D Anderson
(74) *Attorney, Agent, or Firm*—Cooley Godward Kronish LLP

(57) ABSTRACT

The present invention provides improved treatment methods by the administration of both an inhibitor of indoleamine-2,3-dioxygenase in addition to the administration of an additional therapeutic agent.

17 Claims, 19 Drawing Sheets

OTHER PUBLICATIONS

Tsung et al. The Journal of Immunology, 1998, vol. 160, pp. 1369-1377.*

Pinedo et al. The Oncologist, 2000, vol. 5, pp. 497-500.*

Alberti-Giani, "Regulation of the Kynurenine Metabolic Pathway by Interferon-γ in Murine Cloned Macrophages and Microglial Cells," *J. Neurochem*, 1996;66:996-1004.

Alexander et al., "Indoleamine 2,3-Dioxygenase Expression in Transplanted NOD Islets Prolongs Graft Survival After Adoptive Transfer of Diabetogenic Splenocytes," *Diabetes*, 2002;51:356-365.

Almand et al., "Clinical Significance of Defective Dendritic Cell Differentiation in Cancer," *Clin. Cancer Res.*, 2000;6:1755-1766.

Asselin-Paturel et al., "Mouse type IIFN-producing cells are immature APCs with plasmacytoid morphology," *Nat. Immunol.*, 2001;2:1144-1150.

Aune et al., "Inhibition of Tumor Cell Growth by Interferon-γ Is Mediated by Two Distinct Mechanisms Dependent upon Oxygen Tension: Induction of Tryptophan Degradation and Depletion of Intracellular Nicotinamide Adenine Dinucleotide," *J Clin Invest*, 1989;84:863-875.

Azuma, et al., "B70 antigen is a second ligand for CTLA-4 and CD28," *Nature* 1993;366:76-79.

Ben-Efraim, "Immunomodulating Anticancer Alkylating Drugs: Targets and Mechanisms of Activity," *Current Drug Targets*, 2001;2:197-212.

Benson et al., "T-cell activation and receptor downmodulation precede deletion induced by mucosally administered antigen," *J. Clin. Invest.*, 2000;106:1031-1038.

Bjorck et al., "Cutting Edge: CD19+ Pro-B Cells Can Give Rise to Dendritic Cells In Vitro, " *J. Immunol.*, 1998;161:5795-5799.

Borrello et al., "A Universal Granulocyte-Macrophage Colony-Stimulating Factor-Producing Bystander Cell Line for Use in the Formulation of Autologous Tumor Cell-Based Vaccine," *Hum. Gene. Ther.*, 1990;10:1983-1991.

Bronte et al., "Unopposed Production of Granulocyte-Macrophage Colony-Stimulating Factor by Tumors Inhibits CD8+ T Cell Responses by Dysregulating Antigen-Presenting Cell Maturation," *J. Immunol.*, 1999;162:5728-5737.

Carlin et al., "Intrferon-Induced Indoleamine 2,3-Dioxygenase Activity in Human Mononuclear Phagocytes," *J. Leuk. Biol.* 1989;45:29-34.

Cella et al., "Plasmacytoid monocytes migrate to inflamed lymph nodes and produce large amounts of type I interferon," *Nat. Med.*, 1999;5:919-923.

Chambers, "The expanding world of co-stimulation: the two-signal model revisited," *Trend Immunol.* 2001;22:217-223.

Chen et al., "The Role of Tumor Necrosis Factor α in Modulating the Quantity of Peripheral Blood-Derived, Cytokine-Driven Human Dendritic Cells and Its Role in Enhancing the Quality of Dendritic Cell Function in Presenting Soluble Antigens to CD4+ T Cells in Vitro," *Blood*, 1998;91:4652-4661.

Chon, "Cooperative Role of Interferon Regulatory Factor 1 and p91 (STAT1) Response Elements in Interferon-γ-inducible Expression of Human Indoleamine 2,3-Dioxygenase Gene," *J Biol Chem*, 1996;271:17247-17252.

Cochran et al., "Sentinel Lymph Nodes Show Profound Downregulation of Antigen-Presenting Cells of the Pracortex: Implications for Tumor Biology and Treatment," *Mod. Pathol.*, 2001;14:604-608.

Colasante et al., "Role of Cytokines in Distribution and Differentiation of Dendritic Cell/Langerhans' Cell Lineage in Human Primary Carcinomas of the Lung," *Hum. Pathol.*, 1995;26:866-872.

Corbett et al., "Response of Transplantable Tumors of Mice to Anthracenedione Derivatives Alone and in Combination with Clinically Useful Agents," *Cancer Treatment Reports*, 1982;66:1187-1200.

Corcoran et al., "The lumphoid Past of Mouse Plasmacytoid Cells and Thymic Dendritic Cells," *J. of Immunology*, 2003;170:4926-4932.

Cuenca et al., "Extra-Lymphatic Solid Tumor Growth Is Not Immunologically Ignorned and Results in Early Induction of Antigen-Specific T-Cell Anergy: Dominant Role of Cross-Tolerance to Tumor Antigens," *Cancer Res.*, 2003;63:9007-9015.

Curreli et al., "Human Primary CD+ T Cells Activated in the Presence of IFN-α2b Express Functional Indoleamine 2,3-Dioxygenase," *J. Interferon Cytokine Res.*, 2001;21:431-437.

Dai et al., "Molecular Clong, sequencing and expression of human interferon-gamma-inducible indoleamine 2,3-dioxygenase cDNA," *Biochem. Biophys. Res. Commun.*, 1990;168:1-8 GenBank Accession No. M34455.

Daubener, "Establishment of T-helper type 1- and T-helper type 2-like human *Toxoplasma* antigen-specific T-cell clones," *Immunol.* 1995;86:79-84.

Daubener, et al., "Anti-parasitic effector mechanisms in human brain tumor cells: role of interferon-γ and tumor necrosis factor-α," *Eur. J. Immunol.* 1996;26:487-492.

Dranoff, "GM-CSF-based cancer vaccines," *Immunol. Rev.* 2002;188:147-154.

Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci.* USA, 1993;90:3539-3543.

Dudley et al., "Cancer Regression and Autoimmunity in Patients After Clonal Repopulation with Antitumor Lymphocytes," *Science*, 2002;298:850-854. Supplemental On-line Material can be retrieved from www.sciencemag.org/cqi/content/full/1076514/DC1.

Dzionek et al., "BDCA-2, BDCA-3, and BDCA-4: Three Markers for Distinct Subsets of Dendritic Cells in Human Peripheral Blood," *J Immunol.*, 2000;165:6037-6046.

Fallarino et al., "Functional expression of indoleamine 2,3-dioxygenase by murine CD8α+ dendritic cells," *Int. Immunol.*, 2002;14:65-68.

Fallarino et al., "Modulation of tryptophan catabolism by regulator T cells," *Nat. Immunol.*, 2003;4:1206-1212. Epub Oct. 26, 2003.

Fearon et al., The Instructive Role of Innate Immunity in the Acquired Immune Response, *Science* 1996;272:50-54.

Fearon et al., "Regulation of B Lymphocyte Responses to Foreign and Self-Antigens by the CD19/CD21 Complex," *Ann. Rev. Immunol.*, 2000;18:393-422.

Feng et al., "Interferon γ-resistant mutants are defective in the induction of indoleamine 2,3-dioxygenase," *Proc. Natl. Acad. Sci.*, USA, 1989;86:7144-7148.

Friberg et al., "Indoleamine 2,3-dioxygenase contributes to tumor cell evasion of T cell mediated rejection," *Intl J of Cancer*, 2002;101:151-155.

Grant et al., "Induction of Indolamine 2,3-Dioxygenase in Primary Human Macrophages by Human Immunodeficiency Virus Type 1 Is Strain Dependent," *J. Virol.*, 2000;74:4110-4115.

Grohmann et al., "IFN-γ Inhibits Presentation of a Tumor/Self Peptide by CD8α Dendritic Cells Via Potentiation of the CD8α[+]Subset[1]," *J. Immunol.*, 2000;165:1357-1363.

Grohmann et al., "CD40 Ligation Ablates the Tolerogenic Potential of Lymphoid Dendritic Cells[1]," *J. Immunol.* 2001;166:277-283.

Grohmann et al., "IL-6 Inhibits the Tolerogenic Function of CD8α[+]Dendritic Cells expressing Indoleamine 2,3-Dioxygenase[1]," *J. Immunol.* 2001;167:708-714.

Grohmann et al., "CTLA-4-Ig regulates tryptophan catabolism in vivo," *Nature Immunology* 2003;3:1097-1101.

Grohmann et al., "CTLA-4-Ig regulates tryptophan catabolism in vivo," 2002 Nature Publishing Group. Available at http://www.nature.com/natureimmunology Advance online publication. pp. 1-5.

Grohmann et al., "Tolerance, Dcs and tryptophan: much ado about IDO," *Trends in Immunology* 2003;24:242-248.

Grohmann et al., "A Defect in Tryptophan Catabolism Impairs Tolerance in Nonobese Diabetic Mice," *J. Exp. Med.* 2003;198:153-160.

Gupta, "Antiparasitic and Antiproliferative Effects of Indoleamine 2,3-Dioxygenase Enzyme Expression in Human Fibroblasts," *Infect. Immun.* 1994;62:2277-2284.

Hashimoto et al., "Determination of free amino acid enantiomers in rat brain and serum by high-performance liquid chromatography after derivatization with N-*tert.*-butyloxycarbonyl-L-cysteine and o-phthaldialdehyde," *J. Chromatography* 1992;582:41-48.

Hawiger et al., "Dendritic Cells Induce Peripheral T Cell Unresponsiveness Under Steady State Conditions in Vivo," *J. Exp. Med.*, 2001;194:769-779.

Huang et al., "Role of Bone Marrow-Derived Cells in Presenting MHC Class I-Restricted Tumor Antigens," *Science*, 1994;264:961-965.

Hwu et al., "Indoleamine 2,3-Dioxygenase Production by Human Dendritic Cells Results in the Inhibition of T Cell Proliferation," *J. Immunol.* 2000;164:3596-3599.

Izon et al., "A Common Pathway for Dendritic Cell and Early B Cell Development," *J. Immunol.*, 2001;167:1387-1392.

Jonuleit et al., "Pro-inflammatory cytokines and prostaglandins induce maturation of potent immunostimulatory dendritic cells under fetal calf serum-free conditions," *Eur. J. Immunol.*, 1997;27:3135-3142.

Kamimura et al., "Localization and Developmental Change of Indoleamine 2,3-Dioxygenase Activity in the Human Placenta," *Acta. Med.* Okayama, 1991;45:135-139.

Karsunky et al., "Flt3 Ligand Regulates Dendritic Cell Development from Flt3$^+$ Lymphoid and Myeloid-committed Progenitors to Flt3$^+$ Dendritic Cells In Vivo," *J. Exp. Med.*, 2003;198:305.

Koide, "The Signal Transduction Mechanism Responsible for Gamma Interferon-Induced Indoleamine 2,3-Dioxygenase Gene Expression," *Infect. Immun.* 1994;62:948-955.

Konan, "Importance of the Two Interferon-stimulated Response Element (ISRE) Sequences in the Regulation of the Human Indoleamine 2,3-Dioxygenase Gene," *J Biol Chem*, 1996;271:19140-19145.

Konieczny et al., "IFN-γ Is Critical for Long-Term Allograft Survival Induced by Blocking the CD28 and CD40 Ligand T Cell Costimulation Pathways$^1$," *J. Immunol.*, 1998;160:2059.

Kotera et al., "Comparative Analysis of Necrotic and Apoptotic Tumor Cells As a Source of Antigen(s) in Dendritic Cell-based Immunization$^1$," *Cancer Research* 2001;61(22):8105-8109.

Kudo et al., "Human placental indoleamine 2,3-dioxygenase: cellular localization and characterization of an enzyme preventing fetal rejection," *Biochem. Biophys. Acta*, 2000;1500:119-124.

Lee et al., "Pattern of Recruitment of Immunoregulatory Antigen-Presenting Cells in Malignant Melanoma," *Laboratory Investigation*, 2003;83:1457-1466.

Lee et al., "Tryptophan deprivation sensitizes activated T cells to apoptosis prior to cell division," *Immunology* 2002;107:452-460.

Logan et al., "HeLa cells cocultured with peripheral blood lymphocytes acquire an immuno-inhibitory phenotype through up-regulation of indoleamine 2,3-dioxygenase activity," *Immunol.*, 2002;105:478.

Mackensen, et al., "Delineation of the Dendritic Cell Lineage by Generating Large Numbers of Birbeck Granule-Positive Langerhans Cells from Human Peripheral Blood Progenitor Cells in Vitro," *Blood* 1995;86:2699-2707.

Manegold et al., "Gemcitabine in non-small cell lung cancer (NSCLC)", *Invest New Drugs.* 2000;18(1):29-42.

Martin et al., "Characterization of a new subpopulation of mouse CD8α$^+$B220$^+$dendritic cells endowed with type 1 interferon production capacity and tolerogenic potential," *Blood*, 2002;100:383-390.

Mattei et al., "Expression of Cytokine/Growth Factors and Their Receptors in Human Melanoma and Melanocytes," *Int. J. Cancer*, 1994;56:853-857.

McIlroy et al., "Investigation of human spleen dendritic cell phenotype and distribution reveals evidence of in vivo actibation in a subset of organ donors," *Blood*, 2001;97:3470-3477.

Medawar, "Some Immunological and Endocrinological Problems Raised by the Evolution of Viviparity in Vertebrates," *Symp. Soc. Exp. Biol.* 1953;7:320-388.

Mellor et al., "Cells expressing indoleamine 2,3-dioxygenase inhibit T cell responses," *J Immunol.*, 2002;168:3771-3776.

Mellor et al., "Cutting Edge: Induced Indoleamine 2,3 dioxygenase expression in dendritic cell subsets suppresses T cell clonal expansion," *J Immunol*, 2003;171:1652-1655.

Mellor et al., "Prevention of T cell-driven complement activation and inflammation by Tryptophan catabolism during pregnancy," *Nature Immunol* 2001;2:64-68.

Mellor et al., "Indoleamine 2,3-dioxygenase, immunosuppression and pregnancy," *J. Reprod. Immunol.* 2002;57:143-150.

Mellor et al., "Tryptophan catabolism and regulation of adaptive immunity," J. Immunol. 2003;170:5809-5813.

Mellor et al., "Tryptophan catabolism and T cell tolerance: immunosuppression by starvation?," *Immunol. Today* 1999;20:469-473.

Miki et al., "Blockade of Tryptophan Catabolism Prevents Spontaneous Tolerogenicity of Liver Allografts" *Transplantation Proceedings* 2001;33:129-130.

Mikkola et al., "Reversion of B Cell Commitment Upon Loss of Pax5 Expression," *Science*, 2002;297:110-113.

Moffett et al., "Antibodies to quinolinic acid and the determination of its cellular distribution within the rat immune system," *Cell Tissue Res*, 1994;278:461-469.

Mondino, et al., "The anatomy of T-cell activation and tolerance," *Proc. Natl. Acad. Sci* USA 1996;93:2245-2252.

Morahan, et al., In: Heppner GA, Fulton AM, eds. *Macrophages and Cancer*, Boca Raton, FL: CRC Press 1988:1-25.

Moser, "Dendritic Cells in Immunity and Tolerance—Do They Display Opposite Functions?" *Immunity*, 2003;19:5-8.

Munn, "Cytokine Regulation of Human Monocyte Differentiation in Vitro: The Tumor-Cytotoxic Phenotype Induced by Macrophage Colony-Stimulating Factor is Developmentally Regulated by γ-Interferon," *Cancer Res.* 1993;53:2603-2613.

Munn et al., "Selective Activation-Induced Apoptosis of Peripheral T Cells Imposed by Macrophages," *J. Immunol.*, 1996;156:523-532.

Munn et al., "Prevention of Allogeneic Fetal Rejection by Tryptophan Catabolism," *Science* 1998;281:1191-1193.

Munn et al., "Inhibition of T cell proliferation by macrophage tryptophan catabolism," *J Exp Med*, 1999;189:1363-1372.

Munn et al., "Potential regulatory function of human dendritic cells expressing indoleamine 2,3-dioxygenase," *Science*, 2002;297:1867-1870. Supporting On-Line Material available at www.sciencemag.org/cgi/data/297/5588/1867/DC1/1.

Munn, "Selecting the right dentritic cell subset," Lecture Presented Jan. 31, 2003 at Tandem BMT Meetings at Keystone. Jan. 30-Feb. 3, 2003, 57 pages.

Munn et al., "Expression of indolemine 2,3-dioxygenase by plasmacytoid dendritic cells in tumor-draining lymph nodes," *J. Clin Invest* 2004;114:280-290.

Munn et al., "IDO and tolerance to tumors," *Trends Molec Med.* 2004;10:15-18.

Musso, "Interleukin-r Inhibits Indoleamine 2,3-Dioxygenase Expression in Human Monocytes," *Blood* 1994; 83:1408-1411.

Nagineni, "Mechanisms of Interferon-Induced Inhibition of *Toxoplasma gondii* Replication in Human retinal Pigment Epithelial Cells," *Infect. Immun.* 1996;64(10):4188-4196.

Nguyen et al., "Tumor Growth Enhances Cross-Presentation Leading to Limited T Cell Activation without Tolerance," *J. Exp. Med.*, 2002;195:423-435.

Nossal, "Negative Selection of Lymphocytes," *Cell* 1994;76:229-239.

Nowak et al., "Synergy between Chemotherapy and Immunotherapy in the Treatment of Established Murine Solid Tumors," *Cancer Research* 2003;63:4490-4496.

Nutt et al., "Identification of BSAP (Pax-5) target genes in early B-cell development by loss- and gain-of-function experiments," *EMBO J.*, 1998;17:2319-2333.

Nutt et al., "Committment to the B-lymphoid lineage depends on the transcription factor Pax5," *Nature*, 1999;401:556-562.

Oettle, et al., "Phase I Trail of gemcitabine (Gemzar(, 24 h infusion 5-fluorouracil and folinic acid in patients with inoperable pancreatic cancer", *Anticancer Drugs*, 1999;10(8):699-704.

O'Keefe et al., "Mouse Plasmacytoid Cells: Long-lived Cells, Heterogeneous in Surface Phenotype and Function, that Differentiate Into CD8$^+$Dendritic Cells Only after Microbial Stimulus," *J. Exp. Med.*, 2002;196:1307-1319.

Orenstein et al., "The Macrophage Origin of the HIV-Expressing Multinucleated Giant Cells in Hyperplastic Tonsils and Adenoids," *Ultrastruct. Pathol.*, 1999;23:79-91.

Orlando et al., "Gemcitabine in ovarian cancer", *Semin Oncol.* Jun. 2001;28(3 Suppl 10):62-69.

Pardoll, "Does the Immune System See Tumors as Foreign or Self?," *Ann. Rev. Immunol*, 2003;21:807-839.

Pfefferkorn, "Interferon γ blocks growth of *Toxoplasma gondii* in human fibroblasts by inducing the host cells to degrade tryptophan," *Proc. Natl. Acad. Sci.* USA 1984;81:908-912.

Probst et al., "Inducible Transgenic Mice Reveal Resting Dendritic Cells as Potent Inducers of CD8+Cell Tolerance," *Immunity*, 2003;18:713-720.

Quill, "Anergy as a Mechanism of Peripheral T Cell Tolerance," *J. Immunol.* 1996;156:1325-1327.

Reddy et al., "A Monocyte Conditioned Medium Is More Effective Than Defined Cytokines in Mediating the Terminal Maturation of Human Dendritic Cells," *Blood*, 1997;90:3640-3646.

Report on the Rare Diseases Research Activities at the National Institutes of Health FY 2003. NSC No. 721782 (Group 2A, p. 13). 17 pages. Retrieved from the Internet on Jul. 29, 2004 at http://rarediseases.info.nih.gov/html/reports/fy2003/nci.html.

Restito et al., "Basic Aspects of Tumor Immunology," #346 Keystone Symposia 2003 Abstract Book. Abstract/Poster. Keystone, Colorado, Feb. 17-23, 2003. Meetings on Biomedical and Life Sciences that Encourage Scientific Information Exchange and Networking.

Ridgway, "The First 1000 Dendritic Cell Vaccinees," *Cancer Invest.* 2003;21(6):873-886.

Rissoan et al., "Subtractive hybridization reveals the expression of immunoglobulinlike transcript 7, Eph-B1, granzyme B, and 3 novel transcripts in human plasmacytoid dendritic cells," *Blood*, 2002;100:3295-3303.

Romani et al., "Generation of mature dendritic cells from human blood: An improved method with special regard to clinical applicability," *J. Immunol. Methods*, 1996;196:137-151.

Rosenzwajg, et al., "Human Dendritic Cell Differentiation Pathway from CD34+Hematopoietic Precursor Cells," *Blood* 1996;87:535-544.

Sallusto et al., "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factor α," *J. Exp. Med.*, 1994;179:1109-1118.

Sardar, "Frontal cortex indoleamine-2,3-dioxygenase activity is increased in HIV-1-associated dementia," *Neurosci Let*, 1995;187:9-12.

Shortman et al., "Immunity or tolerance? That is the question for dendritic cells," *Nature Immunol.* 2001;2:988-989.

Shurin et al., "FLT3 Ligand Induces the Generation of Functionally Active Dendritic Cells in Mice," *Cell Immunol.* 1997;179:174-184.

Smith et al., "The host environment promotes the development of primary and metastatic squamous cell carcinomas that constitutively express proinflammatory cytokines IL-1α, IL-6, GM-CFS, and KC," *Clin. Exp. Metastasis*, 1998;16:655-664.

Smyth et al., "A Fresh look at tumor immunosurveillance and immunotherapy," *Nat. Immunol.*, 2001;2:293-299.

Sotomayor et al., "Cross-presentation of tumor antigens by bone marrow-derived antigen-presenting cells is the dominant mechanism in the induction of T-cell tolerance during B-cell lymphoma progression," *Blood*, 2001;98,1070-1077.

Southan et al., "Structural Requirements of the Competitive Binding Site of Recombinant Human Indoleamine 2,3-Dioxygenase," *Med. Chem. Res.*, 1996;343-352.

Speiser et al. "Self Antigens expressed by solid tumors do not efficiently stimulate naive or activated T cells: implications for immunotherapy," *J. Exp. Med.*, 1997;186:645-653.

Springer et al., "*Traffic Signals for Lymphocyte Recirculation and Leukocyte* Emigration: The Multistep Paradigm," *Cell* 1994;76:301-314.

Staveley-O'Carroll et al., "Induction of antigen-specific T cell anergy: an early event in the course of tumor progression," *Proc. Natl. Acad. Sci.* USA, 1998;95:1178-1183.

Steinbrink et al., "Induction of Tolerance by IL-10-Treated Dendritic Cells[1]," J. Immunol., 1997;159:4772-4780.

Steinman, "Escape from "Horror Autotoxicus": Pathogenesis and Treatment of Autoimmune Disease," *Cell* 1995;80:7-10.

Steinman et al., "The Endocytic Activity of Dendritic Cells," *Exp. Med.* 1995;182:283-288.

Steinman et al., "Avoiding horror autotoxicus: the importance of dendritic cells in peripheral T cell tolerance," *Proc. Natl. Acad. Sci.* USA 2002;99:351-358.

Summers et al., "Phenotypic Characterization of Five Dendritic Cell Subsets in Human Tonsils," *Am. J. Pathol.* 2001;159:285-295.

Sutmuller et al., "Synergism of Cytotoxic T Lymphocyte-associated Antigen 4 Blockade and Depletion of CD25+Regulatory T Cells in Antitumor Therapy Reveals Alternative Pathways for Suppression of Autoreactive Cytotoxic T Lymphocyte Responses," *J. Exp. Med.*, 2001;194:823-832.

Szabolcs, et al., "Dendritic Cells and Macrophages Can Mature Independently from a Human Bone Marrow-Derived, Post-Colony-Forming Unit Intermediate," *Blood* 1996;87:4520-4530.

Tafuri et al., "T Cell Awareness of Paternal Alloantigens During Pregnancy," *Science*, 1995;270:630-633.

Takikawa et al., "Induction of Indoleamine 2,3-Dioxygenase in tumor cells transplanted into allogeneic mouse: Interferon-γ Is the Inducer," In: Schwarcz R, ed. Kynurenine and Serotonin Pathways, NY: Plenum Press, 1991:437-444.

Tarazona et al., "Effects of different antigenic microenviroments on the course of CD8+T cell responses in vivo," *Int. Immunol.*, 1996;8:351-358.

Taylor et al., "Relationship between interferon-γ, indoleamine 2,3-dioxygenase, and tryptophan catabolism," *FASEB Journal* 1991;5:2516-2522.

Thomas, "IFN-γ-Mediated Antimicrobial Response," *J. Immunol.* 1993;150:5529-5534.

Thomas et al., "Nitric Oxide Inhibits Indoleamine 2,3-Dioxygenase Activity in Interferon-γ Primed Mononuclear Phagocytes," *J. Biol. Chem.*, 1994;269:14457-14464.

Thomas et al., "Dendritic Cells: Origin and Differentiation," *Stem Cells* 1996;14:196-206.

Thomas et al., "Antioxidants Inhibit Indoleamine 2,3-Dioxygenase in IFN-γ-Activated Human Macrophages: Posttranslational Regulation by Pyrrolidine Dithiocarbamate[1]," *J. Immunol.*, 2001;166:6332-6340.

Trinchieri et al., "Immunoregulation by interleukin-12," *J. Leukocyte Biol.* 1996;59:505-511.

Unanue et al., "The Basis for the Immunoregulatory Role of Macrophages and Other Accessory Cells," *Science* 1987;236:551-557.

Uyttenhove et al., "Evidence for a tumoral immune resistance mechanism based on tryptophan degradation by indoleamine 2,3-dioxygenase", *Nature Medicine* 2003;9(10):1269-1274. Epub Sep. 21, 2003.

van Elsas et al., "Combination Immunotherapy of B16 Melanoma Using Anti-Cytotoxic T Luymphocyte-associated Antigen 4 (CTLA-4) and Granulocyte/Macrophage Colony-Stimulating Factor (GM-CSF)-producing Vaccines Induces Rejection of Subcutaneous and Metastic Tumors Accompanied by Autoimmune Depigmentation," J. Exp. Med. 1999;190(3):355-366.

Venkateshan, "Immunocytochemical localization of the endogenous neuroexcitotoxin quinolinate in human peripheral blood monocytes/macrophages and the effect of human T-cell lymphotropic virus type I infection," *Proc Natl Acad Sci USA*, 1996;93:1636-1641.

Vicari et al., "Reversal of Tumor-induced Dendritic Cell Paralysis by CpG Immunostimulatory Oligonucleotide and Anti-Interleukin 10 Receptor Antibody," *J. Exp. Med.*, 2002;196:541-548.

Vogelsang, "Quinolinic Acid in Patients with Systemic Lupus Erythematosus and Neuropsychiatric Manifestations," *J Rheumatol.*, 1996;23:850-855.

Wick et al., "Antigenic Cancer Cells Grow Progressively in Immune Hosts without Evidence for T Cell Exhaustion or Systemic Anergy," *J. Exp. Med.*, 1997;186:229-238.

Yang et al., "Cutting Edge: Immature Dendritic Cells Generated from Monocytes in the Presence of TFG-β1 Express Functional C-C Chemokine Receptor 6[1]," *J. Immunol.*, 1999;163:1737-1741.

Yang et al., "Cancer-associated immunodeficiency and dendritic cell abnormalities mediated by the prostaglandin EP2 receptor," *J. Clin. Invest.*, 2003;111:727-735.

Yu et al., "Molecular mechanisms underlying IFN-γ-mediated tumor growth inhibition induced during tumor immunotherapy with rIL-12," *Intl Immunol.*, 1996;8:855-865.

Yu et al., "Combination of γ-Irradiation and Dendritic Cell Administration Induces a Potent Antitumor Response in Tumor-Bearing Mice: Approach to Treatment of Advanced Stage Cancer," *Int. J. Cancer*, 2001;94:825-833.

Yu et al., "Cancer vaccines: progress reveals new complexities," *Journ. of Clinical Investigation* 2002;110:289-294.

Habara-Ohkubo et al., (1993) "Establishment of an Antioxoplasma State by Stable Expression of Mouse Indoleamine 2,3-Dioxygenase," *Infection and Immunity*, vol. 61 (5), 1810-1813.

Kaufman et al. (1995) "Xenotransplantation," *Annu. Rev. Immnol.*, vol. 13:339-367.

Takikawa et al., (1990) "IFN-γ Is the Inducer of Indoleamine 2,3-Dioxygenase in Allografted Tumor Cells Undergoing Rejection," *J. Immunol.*, vol. 145 (4), 1246-1250.

Munn et al., Basic Aspects of Tumor Immunology "Dendritic cells (DCs) expressing indoleamine 2,3 dioxygenase (IDO) in malignancy," Basic Aspects of Tumor Immunology. Abstract No. 346, Keystone Symposium, 2003 Abstract Book, p. 107, Keystone Resort, Keystone, Colorado, Feb. 17-23, 2003.

Hou, et al., "Inhibition of indoleamine 2,3-dioxygenase in dendritic cells by stereoisomers of 1-methyl-tryptophan correlates with anti-tumor responses," Cancer Res. Jan. 15, 2007;67(2):792-801.

Agrawal et al., "Oligodeoxynucleoside phosphoroamidates and phosphorothioates as inhibitors of human immunodeficiency virus", *Proc. Natl. Acad. Sci. USA*, 85:7079-7083 (1988).

Albina et al., "Nitric Oxide Production is Required for Murine Resident Peritoneal Macrophages to Suppress Mitogen-Stimulated T Cell Proliferation", *J. Immunol.*, 147(1):144-148 (1991).

"A Regulatory Trio," *Molecular Biology*, 317:873, Aug. 17, 2007.

Askew et al., "Molecular Recognition with Convergent Functional Groups. 6. Synthetic and Structural Studies with a Model Receptor for Nucleic Acid Components", *J. Am. Chem. Soc.*, 111:1082-1090 (1989).

Attwood et al., "The Role of Tryptophan Depletion in T Cell Suppression by Macrophages", *Immunology*, 92(1):7, Abstract only (1997).

Bartlett et al. "Introduction of Immunomodulatory genes into isolated pancreatic islets via biolistic particle bombardment." *Transplant Proc.* Mar:30(2):452.(1998).

Baynes et al., "Lactoferrin and the Inflammatory Response", *Adv. Exp. Med. Biol.*, 357:133-141 (1994).

Begg et al., "Delayed Hematopoietic Development in Osteopetrotic (op/op) Mice", *J. Exp. Med.*, 177:237-242 (1993).

Belongia et al., "An Investigation of the Cause of the Eosinophilia-Myalgia Syndrome Associated with Tryptophan Use", *The New England Journal of Medicine*, 323(6):357-365 (1990).

Berney et al., "Transplantation of islets of Langerhans: new developments." *Swiss Med Wkly*. 132:671-680. 2002.

Beutelspacher et al., "Function of indoleamine 2,3-dioxygenase in corneal allograft rejection and prolongation of allograft survival by over-expression," *Eur. J. Immunol.* 36:690-700. 2006.

Bliznakov, "Serotonin and its precursors as modulators of the immunological responsiveness in mice", *Journal of Medicine*, 11:81-105 (1980).

Blume et al., "Triple Helix Formation by Purine-rich Oligonucleotides Targeted to the Human Dihydrofolate Reductase Promoter", *Nucl. Acids Res.*, 20:1777-1784 (1992).

Bock et al., eds., "Polyfunctional Cytokines: IL-6 and LIF", *Ciba Foundation Symposium 167*, Title page and Table of Contents (1992).

Bock et al., eds., "Interactions Among Cell Signalling Systems", *Ciba Foundation Symposium 164*, Title page and Table of Contents (1992).

Bogdan, "The Multiplex Function of Nitric Oxide in (Auto)immunity", *J. Exp. Med.*, 187(9):1361-1365 (1998).

Bonney et al., "Much IDO about pregnancy", *Nature Medicine*, 4(10):1128-1129 (1998).

Brás et al., "Nitric Oxide Regulates Clonal Expansion and Activation-Induced Cell Death Triggered by Staphylococcal Enterotoxin B", *Infection and Immunity*, 65(10):4030-4037 (1997).

Burke et al., "The role of indoleamine 2,3-dioxygenase in the anti-tumor activity of human interferon-gamma in vivo", *Int. J. Cancer*, 60(1):115-122 (1995).

Cady et al., "1-Methyl-DL-tryptophan, β-(3-Benzofuranyl)-DL-alanine (the Oxygen Analog of Tryptophan), and β-[3-Benzo(b)thienyl]-DL-alanine (the Sulfur Analog of Tryptophan) Are Competitive Inhibitors for Indoleamine 2,3-Dioxygenase", *Arch. Biochem. Biophys.*, 291(2):326-333 (1991).

Capecchi, Ed., "Molecular Genetics of Early Drosophila and Mouse Development", *Current Communications in Molecular Biology. Cold Spring Harbor Laboratory Press*, Title page and Table of Contents (1989).

Casciari et al., "Glucose Diffusivity in Multicellular Tumor Spheroids", *Cancer Research*, 48:3905-3909 (1988).

Cecchini et al., "Role of colony stimulating factor-1 in the establishment and regulation of tissue macrophage during postnatal development of the mouse", *Development*, 120:1357-1372 (1994).

Chapman et al., "Pharmacologically active Benzol[b]thiophen Derivatives. Part VIII. Benzo[b]thiophen analogues of Tryptophan and α-Methyltryptophan, and Some of their 5-Substituted Derivatives", *J. Chem. Soc. (C)*, 14:1855-1858 (1969).

Chen et al., Eradication of Murine Bladder Carcinoma by Intratumor Injection of Bicistronic Adenoviral Vector Carrying cDNAs for the IL-12 Heterodimer and Its Inhibition by the IL-12 p40 Subunit Homodimer, *The Journal of Immunology*, 159:351-359 (1997).

Cheng et al., "Relationship Between the Inhibition Constant ($K_1$) and the Concentration of Inhibitor Which Causes 50 Per Cent Inhibition ($I_{50}$) of an Enzymatic Reaction", *Biochemical Pharmacology*, 22:3099-3108 (1973).

Cicala et al., "No-naproxen modulates inflammation, nociception and downregulates T cell response in rat Freund's adjuvant arthritis", *British Journal of Pharmacology*, 130(6):1399-1405 (2000).

Cooney et al., "Site-Specific Oligonucleotides Binding Represses Transcription of the Human c-myc Gene in Vitro", *Science*, 241:456-459 (1988).

Crooke, "Progress Toward Oligonucleotide Therapeutics: Pharmacodynamic Properties", *FASEB J.*, 7:533-539 (1993).

Dalton et al., "Multiple Defects of Immune Cell Function in Mice with Disrupted Interferon-γ Genes", *Science*, 259:1739-1742 (1993).

Degauque et al., "Dominant Tolerance to Kidney Allografts Induced by Anti-Donor MHC Class II Antibodies: Cooperation between T and Non-T CD 103+ Cells," *Journ. Of Immunology*. pp. 3915-3922. (2006).

Dong et al., "Activation of CFTR chloride current by nitric", *EMBO J.*, 14(12):2700-2707 (1995). Abstract only (1 pg.).

Duval-Valentin et al., "Specific Inhibition of Transcription by Triple Helix-Forming Oligonucleotides", *Proc. Natl. Acad. Sci. USA*, 89:504-508 (1992).

Efron et al., "Nitric oxide generation from L-arginine is required for optimal human peripheral blood lymphocyte DNA synthesis", *Surgery*, 110:327-334 (1991).

Ellington et al., "In vitro selection of RNA molecules that bind specific ligands," *Nature*, Aug. 30;346(6287):812-22. (1990).

Ellington et al., "Selection in vitro of single-stranded DNA molecules that fold into specific ligand-binding structures", *Nature*, 355(6363):850-852 (1992).

Fleckner et al., "Human interferon γ potently induces the synthesis of a 55-kDa protein (γ2) highly homologous to rabbit peptide chain release factor and bovine tryptophanyl-tRNA synthetase", *Proc. Natl. Acad. Sci. USA*, 88(24):11520-11524 (1991).

Fleckner et al., "Differential Regulation of the Human, Interferon Inducible Tryptophanyl-tRNA Synthetase by Various Cytokines in Cell Lines", *Cytokine*, 7(1):70-77 (1995).

Giannoukakis et al., "Targeting Autoimmune Diabetes with Gene Therapy." *Diabetes*, vol. 48, pp. 2107-2121 (1999).

Giannoukakis et al., "Prevention of beta cell dysfunction and apoptosis activation in human islets by adenoviral gene transfer of the insulin-like growth factor I." *Gene Ther.* Dec;7(23):2015-22 (2002).

Giannoukakis et al., "Infection of intact human islets by a lentiviral vector." *Gene Ther.* Sep;6(9):1545-51 (1999).

Giannoukakis et al., "Adenoviral Gene Transfer of the Interleukin-1 Receptor Antagonist Protein to Human Islets Prevents IL-1β-Induced β-Cell Impairment and Activation of Islet Cell Apoptosis in Vitro." *Diabetes*, vol. 48, Sep. 1999, pp. 17301736.

Gmünder et al., "Macrophages Regulate Intracellular Glutathione Levels of Lymphocytes. Evidence for an Immunoregulatory Role of Cysteine", *Cell. Immunol.*, 129:32-46 (1990).

Grigoriev et al., "A Triple Helix-forming Oligonucleotide-Intercalator Conjugate Acts as Transcriptional Repressor via Inhibition of NF KB Binding to Interleukin-2 Receptor α-Regulatory Sequence", *J. Biol. Chem.*, 267:3389-3395 (1992).

Haspot et al., "Anti-CD28 Antibody-Induced Kidney Allograft Tolerance Related to Tryptophan Degradation and TCR- Class II- B7+ Regulatory Cells," *Amer. Journ. Of Transplantation*, 5:2339-2348. (2005).

Hayaishi, "Utilization of Superoxide Anion by Indoleamine Oxygenase-Catalyzed Tryptophan and Indoleamine Oxidation", *Adv. Exp. Med. Biol.*, 398:285-289 (1996).

Heesen et al., "β$_2$-Adrenoceptor Density of Human Lymphocytes After Nitroprusside-Induced Hypotension", *Anesth Analg*, 81:1250-1254 (1995).

Hogan et al., "Manipulating the Mouse Embryo—A Laboratory Manual", *Cold Spring Harbor Laboratory*, 1 pg. publication (1986).

Holt et al., "An Oligomer Complementary to c-myc mRNA Inhibits Proliferation of HL-60 Promyelocytic Cells and Induces Differentiation", *Mol. Cell. Biol.*, 8:963-973 (1988).

Hou et al., "Inhibition of Indoleamine 2,3-Dioxygenase in Dendritic Cells by Stereoisomers of 1-Methyl-Tryptophan Correlates Antitumor Responses," *Cancer Res.*, 67:(2):792-801 (2007).

Ibrahim et al., "The injured cell: the role of the dendritic cell system as a sentinel receptor pathway", *Immunology Today*, 16(4):181-186 (1995).

Itakura et al., "Synthesis and use of Synthetic Oligonucleotides", *Ann. Rev. Biochem.*, 53:323-356 (1984).

Iwata et al., "Thiol-Mediated Redox Regulation of Lymphocyte Proliferation. Possible Involvement of Adult T Cell Leukemia-Derived Factor and Glutathione in Transferrin Receptor Expression", *J. Immunol.*, 152:5633-5642 (1994).

Janeway, Jr., "The immune system evolved to discriminate infectious nonself from noninfectious self", *Immunology Today*, 13(1):11-16 (1992).

Janeway, Jr. et al., *ImmunoBiology, The Immune System in Health and Disease*, Current Biology Limited, London, U.K., 12:30-12:34 (1994).

Jorgensen et al., "Gene therapy in osteoarticular diseases: where are we?", *Immunology Today*, 19(9):387-391 (1998).

Kadoya et al., "Gene structure of human indoleamine 2,3-dioxygenase," *Bio. and Biophysical Research Comm.* vol. 189, No. 1 pp. 530-536 (1992).

Kakuda et al., "Na(+)-independent transport (uniport) of amino acids and glucose in mammalian cells", *J. Exp. Biol.*, 196:93-108 (1994).

Kamath et al., "Amino Acid-Restricted Diets in the Treatment of Mammary Adenocarcinoma in Mice", *J. Nutr.*, 118(9):1137-1142 (1988).

Kamijo et al., "Mice That Lack the Interferon-β Receptor Have Profoundly Altered Responses to Infection with Bacillus Calmette-Guérin and Subsequent Challenge with Lipopolysaccharide", *J. Exp. Med.*, 178:1435-1440 (1993).

Kapturczak et al. "Transduction of human and mouse pancreatic islet cells using a bicistronic recombinant adeno-associated viral vector." *Mol Ther*. Feb;5(2):154-60 (2002).

Kenyon et al. "Islet transplantation; present and future perspectives." *Diabetes Metab Rev.* Dec;14(4)303-313 (1998).

Kisselev, "Mammalian tryptophanyl-tRNA synthetases", *Biochimie*, 75:1027-1039 (1993).

Kolb et al., "Nitric oxide in autoimmune disease: cytotoxic or regulatory mediator?", *Immunology Today*, 19(12): 556-561 (1998).

Li et al., "Expression of indoleamine 2,3-dioxygenase in dermal fibroblasts functions as a local immunosuppressive factor," *J. Invest. Dermatol*. 122(4):953-964 (2004).

Logan et al., "Potential Use of Genetically Modified Pigs as Organ Donors for Transplantation into Humans," *Clinical and Exper. Pharm. and Physiology*, 26:1020-1025 (1999).

MacMicking et al., "Nitric Oxide and Macrophage Function", *Annu. Rev. Immunol.*, 15:323-350 (1997).

Maher et al., "Inhibition of DNA binding proteins by oligonucleotide-directed triple helix formation", *Science*, 245:725-730 (1989).

Mayeno et al., "Characterization of "Peak," a Novel Amino Acid Associated with Eosinophilia-Myalgia Syndrome", *Science*, 250:1707-1708 (1990).

McGivan et al., "Regulatory and molecular aspects of mammalian amino acid transport", *Biochem J.*, 299(Part 2):321-334 (1994).

McKinlay et al., "Rational Design of Antiviral Agents", *Annu. Rev. Pharmacol. Toxicol.*, 29:111-122 (1989).

Mellor et al., "HLA-G transgenic mice", *Journal of Reproductive Immunology*, 43:253-261 (1999).

Mellor et al., "Immunology at the Maternal-Fetal Interface: Lessons for T Cell Tolerance and Suppression", *Annu. Rev. Immunol*, 18:367-391 (2000).

Mellor et al., "Cutting edge: CpG Oligonucleotides Induces Spenic CD19+ Dendritic Cells to Acquire Potent Indoleamine 2,3-Dioxygenase-Dependent T Cell Regulatory Functions via IFN Type 1 Signaling," *Journ. Of Immun*. pp. 5601-5605 (2005).

Merrifield, "Solid Phase Peptide Synthesis. I. The Synthesis of a Tetrapeptide", *J. Am. Chem. Soc.*, 85:2149-2154 (1963).

Meyer et al., "Trptophan metabolism in chronic inflammatory lung disease", *J. Lab. Clin. Med.*, 126(6):530-540 (1995).

Mills, "Molecular Basic of "Suppressor" Macrophages—Arginine Metabolism via the Nitric Oxide Synthetase Pathway", *J. Immunol.*, 146(8):2719-2723 (1991).

Moore et al., "Enhanced Response of Macrophages to CSF-1 in Autoimmune Mice", *J. Immunol*, 157:433-440 (1996).

Morgan et al., "Scleroderma and autoimmune thrombocytopenia associated with ingestion of L-tryptophan", *British Journal fo Dermatology*, 128:581-583 (1993).

Muller et al., "Inhibition of indoleamine 2,3-dioxygenase, an immunoregulatory target of the cancer suppression gene Bin1, potentiates cancer chemotherapy," Nature Medicine, 11:3:312-319. (2005).

Muller et al., "Marrying Immunotherapy with Chemotherapy: Why Say IDO?," Cancer Res., 65:(18):8065-8068. (2005).

Mulligan, "The Basic Science of Gene Therapy", *Science*, 260:926-932 (1993).

Munn et al., "Antibody-Dependent Antitumor Cytotoxicity by Human Monocytes Cultured with Recombinant Macrophage Colony-Stimulating Factor", *J. Exp. Med.*, 170:511-526 (1989).

Munn, David H., "Inhibition of T Cells by Tryptophan Degradation," Grant Abstract, Grant No. 1R21A144759-01 [online]. National Institutes of General Medical Sciences, National Institutes of Health, project dates Sep. 30, 1998-Sep. 29, 2000 [retrieved on Feb. 15, 2001]. Retrieved from the Internet: URL: http.commons.cit.nih.gov/crisp_historical/crisp_lib.getdoc?textkey=2802812 &p_grant_num=1R21AI44759-01&p_query=&ticket=63957 &p_audit_session_id=363938&p_keywords=>, 2 pages.

Munn, "Indoleamine 2,3-dioxygenase, tumor-induced tolerance and counter-regulation," *Curr. Opin. Immunol*. Apr;18(2):220-225. Epub Feb. 7, 2006. (2006).

Narang et al., "[61] Chemical Synthesis of Deoxyoligonucleotides by the Modified Triester Method", *Methods in Enzymology*, 65:610-620 (1980).

Offensperger et al., "In Vivo inhibition of duck hepatitis B virus replication and gene expression b phosphorothioate modified antisence oligodeoxynucleotides", *EMBO J.*, 12(3):1257-1262 (1993).

Orson et al., "Oligonucleotide inhibition of IL2Rα mRMA transcription by promoter region collinear riplex formation in lmphocytes", *Nucl. Acids Res.*, 19:3435-3441 (1991).

Ottaviani et al., "The invertebrate phagocytic immunocyte: clues to a common evolution of immune and neuroendocrine systems", *Immunol. Today*, 18(4):169-174 (1997).

Ozaki et al., "Induction of indoleamine 2,3-dioxygenase: A mechanism of the antitumor activity of interferon γ", *Proc. Natl. Acad. Sci. USA*, 85:1242-1246 (1988).

Perry et al., "The Use of 3D Modelling Databases for Identifying Structure Activity Relationships", *QSAR: Quantitative Structure-Activity Relationships in Drug Design, Proceedings of the 7$^{th}$ European Symposium on QSAR held in Interlaken, Switzerland*, Sep. 5-9, 1988, Alan R. Liss, Inc.- New York, pp. 189-193 (1989).

Peterson et al., "Evaluation of Functionalized Tryptophan Derivatives and Related Compounds as Competitive Inhibitors of Indoleamine 2,3-Dioxygenase", *Med. Chem. Res.*, 3:531-544 (1994).

Postel et al., Evidence that a triplex-forming oligodeoxyibonucleotide binds to the c-myc promoter in heLa cells, thereby reducing c-myc mRNA levels, *Proc. Natl. Acad. Sci. USA*, 88:8227-8231 (1991).

Potter et al., "Enhancer-dependent expression of human κ immunoglobulin genes introduced into mouse pre-B lymphocytes by electroporation", *Proc. Natl. Acad. Sci. USA*, 81:7161-7165 (1984).

Potula et al., Inhibition of indoleamine 2,3-dioxygenase (IDO) enhances elimination of virus-infected macrophages in an animal model of HIV-1 encephalitis, *Immunobiology, Blood*, Oct. 1, 2005, 106(7):233822390.

Prasad et al., "Relationship between Thyroid Hormone Transport and Neutral Amino Acid Transport in JAR Human Choriocarcinoma Cells", *Endocrinology*, 134(2):574-581 (1994).

Raynovich, "Late-Stage Cancer Vaccines Set to Launch with Five Major Players, Therapeutic Vaccines Could Transform Medical Care," *GEN Biobusiness Wall Street Biobeat*. Mar. 1, 2007. genengnews.com. *Gen.Eng. & Biotech. News*.

Renault et al., "Base Transitions Are the Most Frequent Genetic Changes at P53 in Gastric Cancer", *Cancer Research*, 53:2614-2617 (1993).

"Rheumatoid Arthritis," *Genetic Eng. & Biotech. News*, Mar. 1, 2007. Genengnews.com . (72) Translational Medicine.

Ripka, "Computers picture the perfect drug", *New Scientist*, 54-57 (1988).

Rosoff et al., "4,4'-Diisothiocyanatostilbene-2,2'-disulfonic Acid Inhibits CD3-T Cell Antigen Receptor-stimulated $Ca^{2+}$ Influx in Human T Lymphocytes", *J. Biol. Chem.*, 263(36):19535-19540 (1998).

Rouvinen et al., "Computer-Aided Drug Design", *Acta Pharmaceutica Fennica*, 97:159-166 (1988).

Rubin et al., Interferon Induces Tryptophanyl-tRAN Sythetase Expression in Human Fibroblasts, *The Journal of Biological Chemistry*, 266(36):24245-24248 (1991).

Serreze et al., Defects in the Differentiation and Function of Antigen Presenting Cells in NOD/Lt Mice, *J. Immunol.*, 150(6):2534-2543 (1993).

Sambrook et al., Molecular Cloning: A Laboratory Manual, Second Edition, Books 1-3, Cold Spring Harbor Laboratory Press, Cold Spring Harbor, New York, Title page and Table of Contents only, 29 pages (1989).

Sanchez del Pino et al., "Neutral Amino Acid Transport Characterization of Isolated Luminal and Abluminal Membranes of the Blood-Brain Barrier", *The Journal of Biological Chemistry*, 270(25):14913-14918 (1995).

Sarin et al., "Inhibition of acquired immunodeficiency syndrome virus by oligodeoxynucleoside methylphosphonates", *Proc. Natl. Acad. Sci. USA*, 85:7448-7451 (1988).

Schaller et al., "Identification of the Disulfide Bonds of the Human Complement Component C9 and Comparison with the Other Terminal Compoennts of the Membrane Attack Complex", *MPSA Short Communications*, pp. 472-473 (1996).

Schröder et al., "Suppression of the Modulatory Effects of the Antileukemic and Anti-Human Immunodeficiency Virus Compound Avarol on Gene Expression by Tryptophan", *Cancer Research*, 49(8):2069-2076 (1989).

Serreze et al., Defects in the Differentiation and Function of Antigen Presenting Cells in NOD/Lt Mice, *J. Immunol.*, 150(6):2534-2543 (1993).

Seymour et al., "Identification and Characterization of a Novel, High-Affinity Tryptophan-Selective Transport System in Human Macrophages", *Blood*, 90(10):448a, Abstract only (1997).

Sharma et al., "Plasmacytoid dendritic cells from mouse tumor-draining lymph nodes directly activate mature Tregs via indoleamine 2,3-dioxygenase," First Published online on Aug. 16, 2007. *Journ. Of Clinical Investigation, Research Article*. pp. 1-13.

Shaw et al., "Modified deoxyoligonucleotides stable to exonuclease degradation in serum", *Nucleic Acids Res.*, 19(4):747-750 (1991).

Sidransky et al., "Effect of Tryptophan on Hepatoma and Host Liver of Rats. Influence After Treatment with Hypertonic Sodium Chloride and Carbon Tetrachloride", *Exp. Mol. Pathol.*, 35(1):124-136 (1981).

Sigalla et al. "Adenovirus-mediated gene transfer into isolated mouse adult pancreatic islets: normal beta-cell function despite induction of an anti-adenovirus immune response." *Hum Gene Ther* Sep. 1, 1997;8(13) 1625-1634.

Sono et al., "Indoleamine 2,3-Dioxygenase. Equilibrium Studies of the Tryptophan Binding to the Ferric, Ferrous, and Co-Bound Enzymes", *J. Biol. Chem.*, 255(4):1339-1345 (1980).

Sponass et al., "Induction of tolerance to self MHC class I molecules expressed under the control of milk protein or β-globin gene promoters," *Intl. Immun.*, vol. 6, No. 2, pp. 277-287 (1994).

Steckel et al., "Indoleamine 2,3-Dioxygenase expression in patients with acute graft-;versus-host disease after allogeneic stem cell transplantation and in pregnant women: association with the induction of allogeneic immune tolerance?," *Scandinavian Journ. Of Immun.*, 57, pp. 185-191 (2003).

Sternberg et al., "Development of a Scleroderma-Like Illness During Therapy with L5-Hydroxytryptophan and Carbidopa", *N. Engl. J. Med.*, 303(14):782-787 (1980).

Suzuki, "Abalone Myoglobins Evolved from Indoleamine Dioxygenase: The cDNA-Derived Amino Acid Sequence of Myoglobin from *Nordotis madaka*", *Journal of Protein Chemistry*, 14(1):9-13 (1994).

Suzuki et al., "Convergent evolution. The gene structure of Sulculus 41 kDa myoglobin is homologous with that of human indoleamine dioxygenase," *Biochem. Biophys. Acta*, 1308:41-48 (1996).

Swanson et al., "CD11c+ Cells Modulate Pulmonary Immune Responses by Production of Indoleamine 2,3-Dioxygenase," *Am. Journ. Of Respiratory Cell and Molecular Biology*, vol. 30, pp. 311-318 (2004).

Szostak, "In vitro genetics", *TIBS*, 17(3):89-93 (1992).

Takikawa et al., "Induction of Indoleamine 2,3-Dioxygenase in Tumor Cells Implanted Into Allogeneic Mouse: Interferon-γ is the Inducer", *Kynurenine and Serotonin Pathways*, pp. 437-444, Plenum Press: New York (1991).

Terness et al., "Inhibition of allogeneic T cell proliferation by Indoleamine 2,3-Dioxygenase-expressing dendritic cells: mediation of suppression by tryptophan metabolites," *J. Exp. Med.* vol. 196, No. 4, pp. 447-457 (2002).

Thomson et al., "Are dendritic cells the key to liver transplant tolerance?", *Immunology Today*, 6 pgs. (1999).

Toore et al., "Immunological Aspects of Nitric Oxide in HIV-1 Infection", *Medical Hypotheses*, 47:405-407 (1996).

Weber, et al. "Adenoviral transfection of isolated pancreatic islets: a study of programmed cell death (apoptosis) and islet function." *J Surg Res*. Apr;69(1):23-32 (1997).

Weiss et al., "Linkage of cell-mediated immunity to iron metabolism", *Immunology Today*, 16(10):495-500 (1995).

Werner et al., Human Macrophages Degrade Tryptophan Upon Induction by Interferon-Gamma, *Life Sciences*, 41(3):273-280 (1987).

Wickstrom et al., "Human promyelocytic leukemia HL-60 cell proliferation and *c-myc* protein expression are inhibited by an antisense pentadecadeoxynucleotide targeted against *c-myc* mRNA", *Proc. Natl. Acad. Sci. USA*, 85:1028-1032 (1988).

Willenborg et al., IFN-γ Plays a Critical Down-Regulatory Role in the Induction and Effector Phase of Myelin Oligodendrocyte Glycoprotein-Induced Autoimmune Encephalomyelitis, *J. Immunol*, 157:3223-3227 (1996).

Young et al., "Triple helix formation inhibits transcription elongation in vitro", *Proc. Natl. Acad. Sci. USA*, 88:10023-10026 (1991).

Zamecnik et al., "Inhibition of Rouse sarcoma virus replication and cell transformation by a specific oligodeoxynucleotide", *Proc. Natl. Acad. Sci. USA*, 75:280-284 (1978).

Zamecnik et al., Inhibition of replication and expression of human T-cell lymphotropic virus type III in cultured cells by exogenous systhenic oligonucleotides complementary to viral RNA, *Proc. Natl. Acad. Sci. USA*, 83:4143-4146 (1986).

Zhou et al., "Expanded cohorts of maternal $CD8^+$ T-cells specific for paternal MHC class I accumulate during pregnancy", *J. Reprod. Immunol.*, 40:47-62 (1998).

Zhou et al., "Evidence for a Close Link between the Thyroid Hormone Transport System and the Aromatic Amino Acid Transport System T in Erythrocytes", *J. Biol. Chem.*, 265(28):17000-17004 (1990).

Zhu et al., "Systemic Gene Expression After Intravenous DNA Delivery into Adult Mice", *Science*, 261:209-211 (1993).

Zimmer et al., "Production of chimaeric mice containing embryonic stem (ES) cells carrying a homoeobox Hox 1.1 allele mutated by homologous recombination", *Nature*, 338:150-153 (1989).

"Chemotherapy Before Breast Surgery is Valuable." Cancerwise, The University of Texas MD Anderson Cancer Center, Featured Article. Retrieved from the Internet on Feb. 25, 2008. Retrieved from http://www.cancerwise.org/jul._2005/display.cfm?id=8FD89A2-41F1-4B7C-844D5550459E1368&method=displayFull&color=green . 4 pages.

"New Treatments" Seattle Cancer Care Alliance, Breast Cancer Program. Retrieved from the Internet on Feb. 25, 2008. Retrieved from http://www.seattlecca.org/patientsandfamilies/adultCare/clinicalProgs/breastCancer/newTreatments/NeoajuvantChemotherapy.htm . 1 page.

Chemotherapy Information/Chemotherapy Terms. Retrieved from the Internet on Feb. 25, 2008. Retrieved from http://www.chemocare.com/whatis/important_Chemotherapy_terms.asp . 2 pages.

Hou et al., "The immunosuppressive effects of 10 mg/kg cyclophosphamide in Wistar rats," 2007. *Environ. Toxicology and Pharmacology*, 24:30-36.

On-Line Article. 2008. MedicineNet.com. Information on Generic Name: Cyclophosphamide, Brand Name: Cytoxan. Retrieved from the Internet on Apr. 9, 2008. Retrieved from http://www.medicinenet.com/script/main/art.asp?articlekey=12343&pf=3&page=1. 2 pages.

Moyo et al., "High-dose cyclophospharnde for refractory autoimmune hemolytic anemia," 2002, Blood. 100(2):704-706.

Nygaard et al., "Blood and spleen lymphocytes as targets for immunotoxic effects in the rat- a comparison," 2002. *Toxicology*, 174:153-161.

Ochalek, "Divergence between delayed-type hypersensitivity (DTH) to polyoma tumor-associated antigen and antitumor efficacy in polyoma-bearing recipients of therapeutic non-cytolytic, DTH-mediating lymphocyctes," 1993. *Immunol. Lett.* 38(2):97-102.

On-Line Article. "Taxotere®/Cytoxam® Superior to Standard Adriamycin®/Cytoxan as Adjuvant Therapy in Breast," *CancerConsultants.com*. Retrieved from the internet on Feb. 29, 2008. Retrieved from http://professional.cancerconsultants.com/print.aspx?id=35701 2 pages.

Reiner et al., "Pulse Cyclophosphamide Therapy for Refractory Autoimmune Thrombocytopenic Purpura," 1995. *Blood*, 85(2):351-358.

Armstrong et al., "Direct liquid chromatographic separation of racemates with an alpha-cyclodextrin bonded phase," Nov. 1, 1987 *Anal. Chem.* 59(21):2594-2596.

Armstrong et al., "Mechanism of capillary electrophoresis enantioseparations using a combination of an achiral crown ether plus cyclodextrins," Jan. 9, 1998 *J. Chromatography A* 793(1):115-134.

Chen et al., "Simultaneous separation of sixteen positional and optical isomers of the tryptophan family by ligand-exchange micellar electrokinetic chromatography," Apr. 1999 *Chromatographia* 49(7/8):436-443.

Chen et al., "Interaction between 18-crown-6-tetracarboxylic acid and positional substituents of enantiomers and simultaneous separation of positional enantiomers of methyl-DL-tryptophans by capillary electrophoresis," Jul. 2001 *Electrophoresis* 22(11):2136-2142.

Irie et al., "Synthesis of 6-substituted indolactams by microbial conversion," May 29, 1995 *Tetrahedron* 51(22):6255-6266.

Kucharczyk et al., "Tetrapeptide tachykinin antagonists: synthesis and modulation of the physicochemical and pharmacological properties of a new series of partially cyclic analogs," May 28, 1993 *J. Med. Chem.* 36(11):1654-1661.

Kuhn et al., "Adsorption chromatography on cellulose. IV. Separation of D- and L-methyl-tryptophan on cellulose with aqueous solvents," May 19, 1989 *J. Chromatography* 469:253-260.

Lederer, "Adsorption chromatography on cellulose VII. Chiral separations on cellulose with aqueous solvents," Jun. 26, 1992 *J. Chromatography* 604(1):55-62.

Lederer et al., "Adsorption chromatography on cellulose XIV. Some results using aqueous solutions of soluble cyclodextrin polymers as eluents," Feb. 9, 1996 *J. Chromatography A* 723(2):405-409.

Lepri et al., "Reversed phase planar chromatography of enantiomeric tryptophans with bovine serum albumin in the mobile phase," Jul./Aug. 1992 *J. Planar Chromatography* 5:234-238.

Nardi et al., "Use of cyclodextrins in capillary zone electrophoresis for the separation of optical isomers: Resolution of racemic tryptophan derivatives," 1992 *Chirality* 4(1):56-61. Epub Sep. 21, 2004.

Zhang and Cook, "Pictet-Spengler reactions in aprotic media. $N_b$-benzyl promoted retention of optical activity in the synthesis of an indolo substituted azabicyclo[3.3.1]nonane, a key template for the synthesis of macroline alkaloids," 1988 *Heterocycles* 27(12):2795-2802.

Zhang et al., "Stereospecificity in the Pictet-Spengler reaction. Enantiospecific synthesis of (6S, 10S)-(—)-5-methyl-9-oxo-12-benzyl-6,7,8,9,10,11-hexahydro-6, 10-imino-5*H*-cyclooct[*b*]indole, a template for preparation of macroline/sarpagine alkaloids," 1992 *Heterocycles* 34(3):517-547.

Ball et al., "Characterization of an indoleamine 2,3-dioxygenase-like protein found in humans and mice," 2007 *Gene* 396:203-213.

Habara-Ohkubo et al., "Cloning and expression of a cDNA encoding mouse indoleamine 2,3-dioxygenase," *Gene* 105(2):221-227 (1991).

Metz et al., "Novel Trypotophan Catabolic Enzyme IDO2 is the Preferred Biochemical Target of the Antitumor Indoleamine 2,3-Dioxygenase Inhibitory Compound D-1-Methyl-Tryptophan," *Cancer Res*. 2007;67:(15):7082-7087.

Miki et al., "Indoleamine 2,3-Dioxygenase Blockade Prevents Spontaneous Liver Allograft Tolerogenicity in the Mouse," Meeting Abstract #714 presented at the ⁵1 Joint Annual Meeting of the American Society of Transplantation held in Chicago, IL: May 13-17, 2000. Published in *Transplantation®*, Apr. 27, 2000; 69(8):S297.

Munn, David H., "Regulation of Macrophage Apoptosis," Grant Abstract, Grant No. 1K08HL03395-01 [online]. National Institutes of General Medical Sciences, National Institutes of Health, project dates Jul. 1, 1995-Jun. 30, 1998 [retrieved on Feb. 15, 2001]. Retrieved from the Internet: <http.commons.cit.nih.gov/crisp_historical/crisp_lib.getdoc?textkey=221164 &p_grant_num=1K08HL03395-01 &p_query=&ticket=63957 &p_audit_session_id=363938&p_keywords=>, 2 pages.

Munn, David H., "Macrophage Immunoregulation Via Tryptophan," Grant Abstract, Grant No. 5R01HL60137-03 [online]. National Institutes of General Medical Sciences, National Institutes of Health, project dates Jan. 1, 1999-Dec. 31, 2002 [retrieved on Feb.15, 2001]. Retrieved from the Internet: <http.commons.cit.nih.gov/crisp_lib.getdoc?textkey=634361&p_query=&ticket=1890054 &p_audit_session_id=3588259&p_keywords=>, 2 pages.

Munn et al., "Indoleamine 2,3-dioxygenase and tumor-induced tolerance," 2007 *Journ. of Clinical Investigation*. 117(5):1147-1154.

Sarkhosh et al., "Immune cell proliferation is suppressed by the interferon-gamma-induced indoleamine 2,3-dioxygenase expression of fibroblasts populated in collagen gel (FPCG)," *J. Cell Biochem*, 2003; 90(1):206-217.

Takikawa et al., "Mechanism of Interferon-γ Action. Characterization of Indoleamine 2,3-Dioxygenase in Cultured Human Cells Induced by Interferon-γ and Evaluation of the Enzyme-Mediated Tryptophan Degradation in its Anticellular Activity," *The Journal of Biological Chemistry*, 263(4):2041-2048 (1988).

* cited by examiner

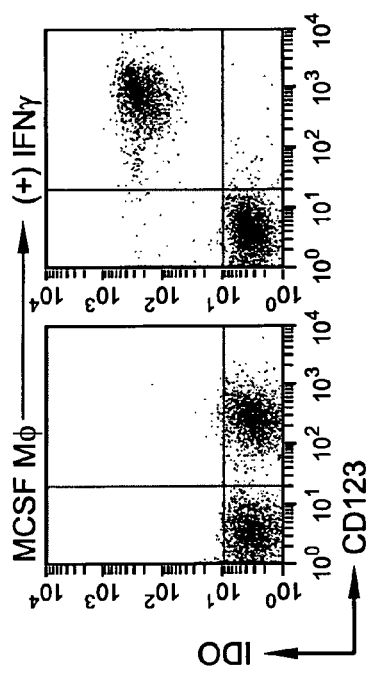
Fig. 2A
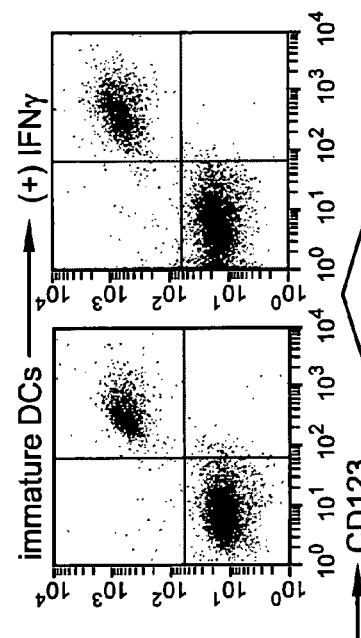
Fig. 2B
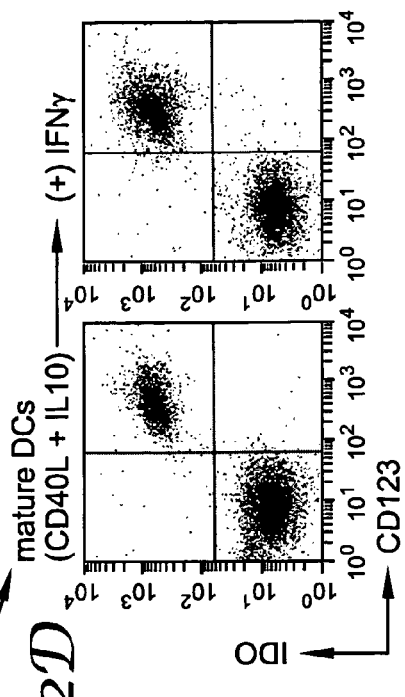
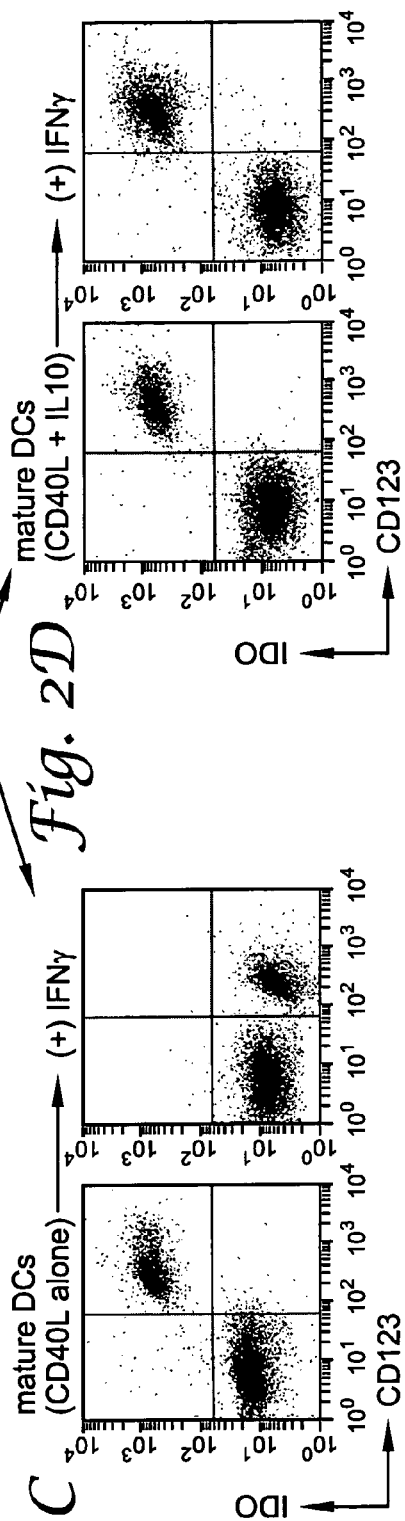
Fig. 2D
Fig. 2C

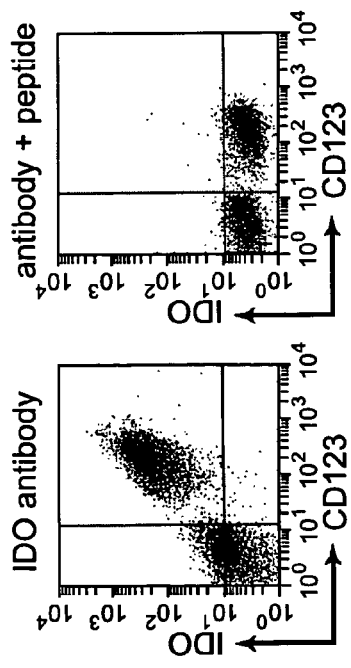

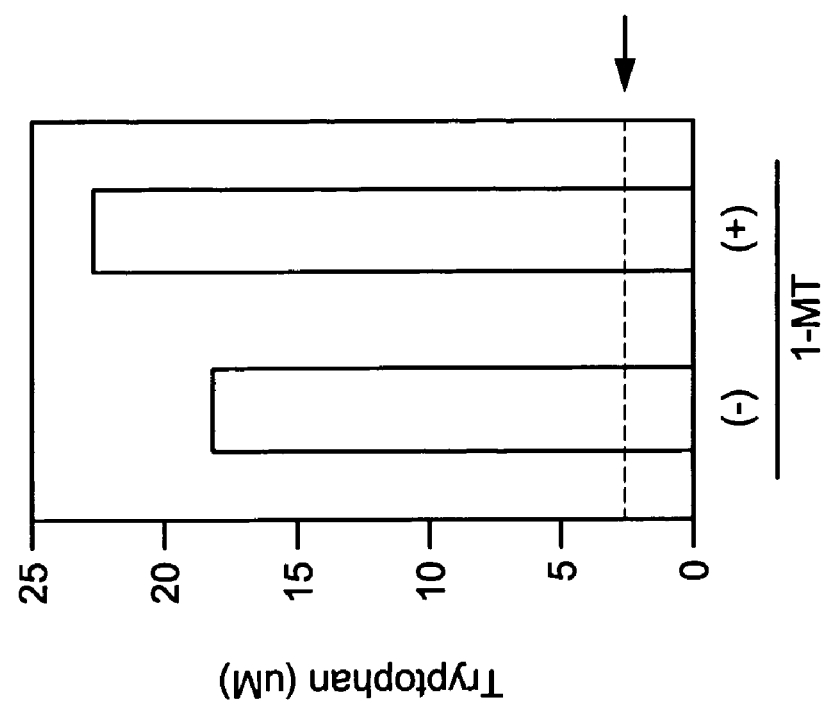
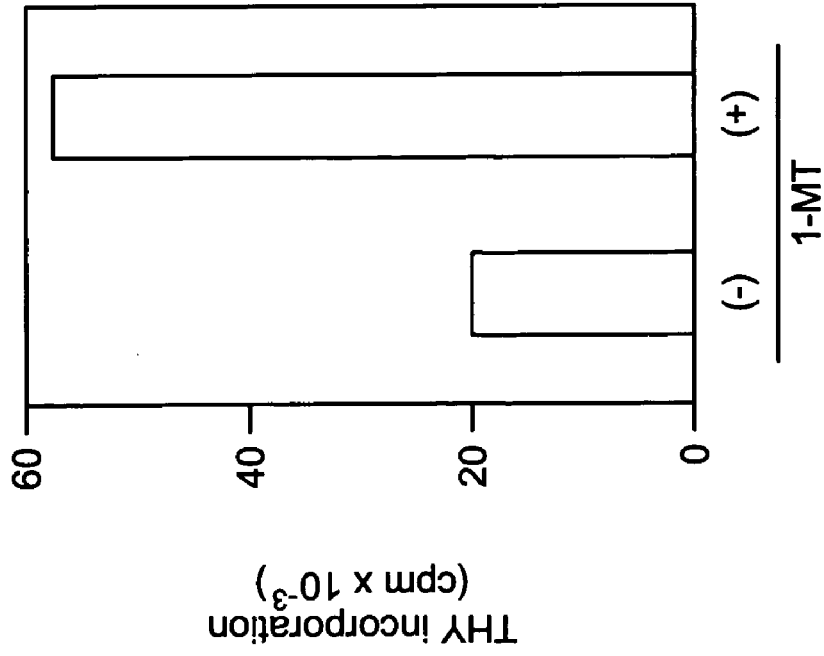
Fig. 4B
Fig. 4A

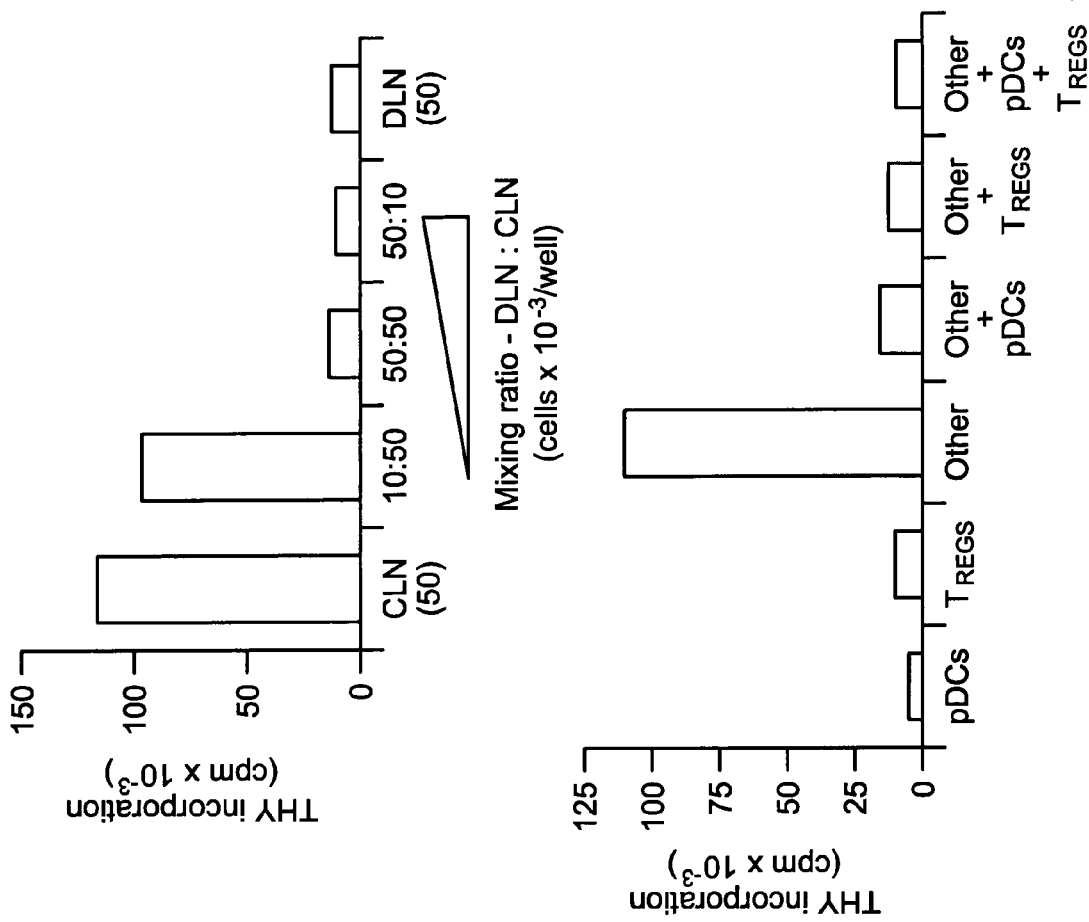
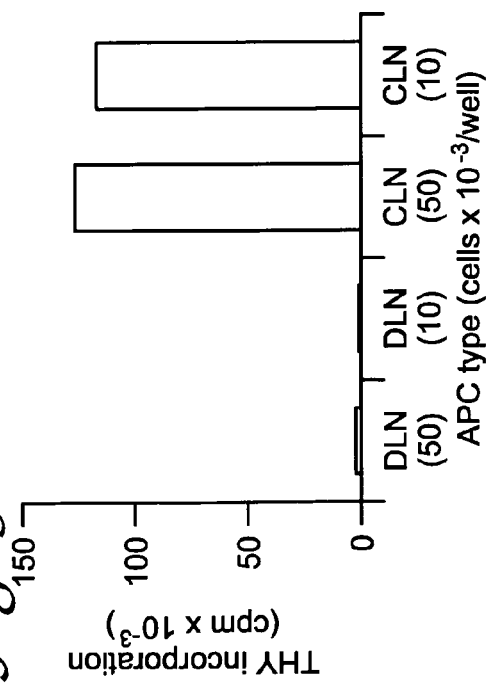
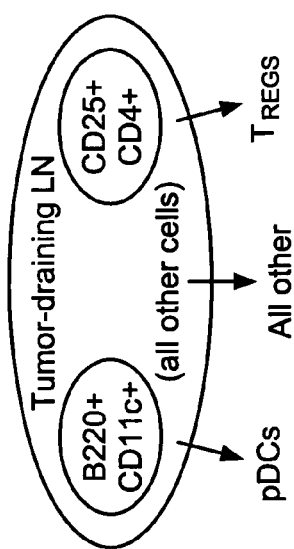
Fig. 5A
Fig. 5B

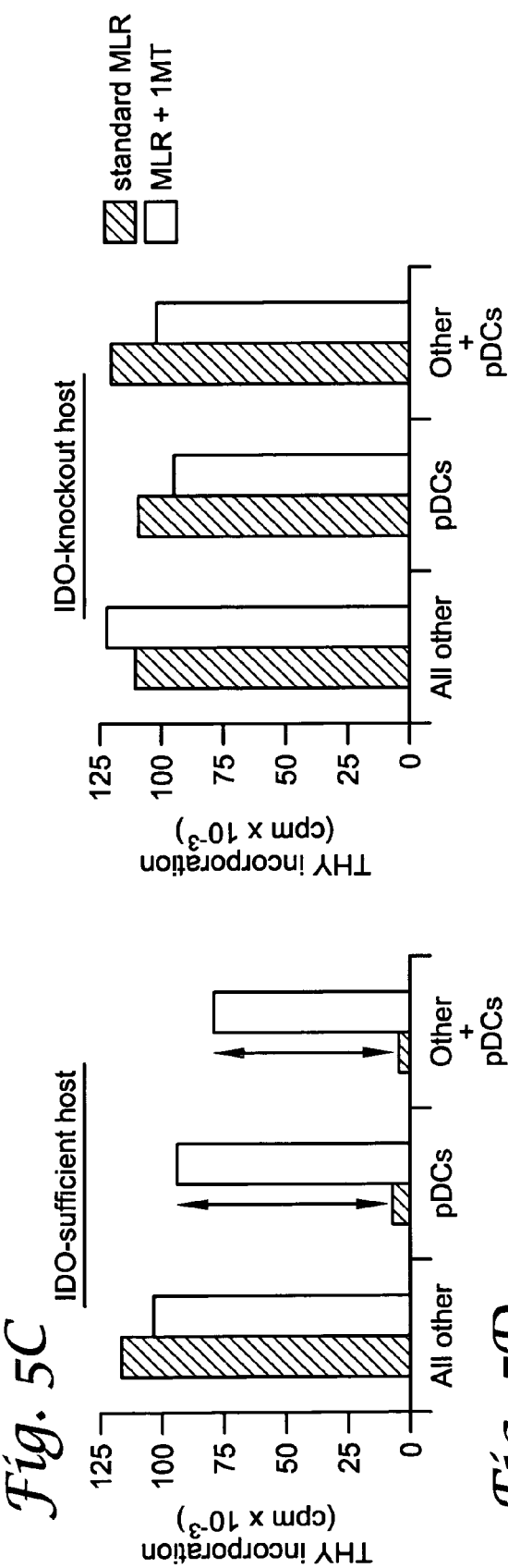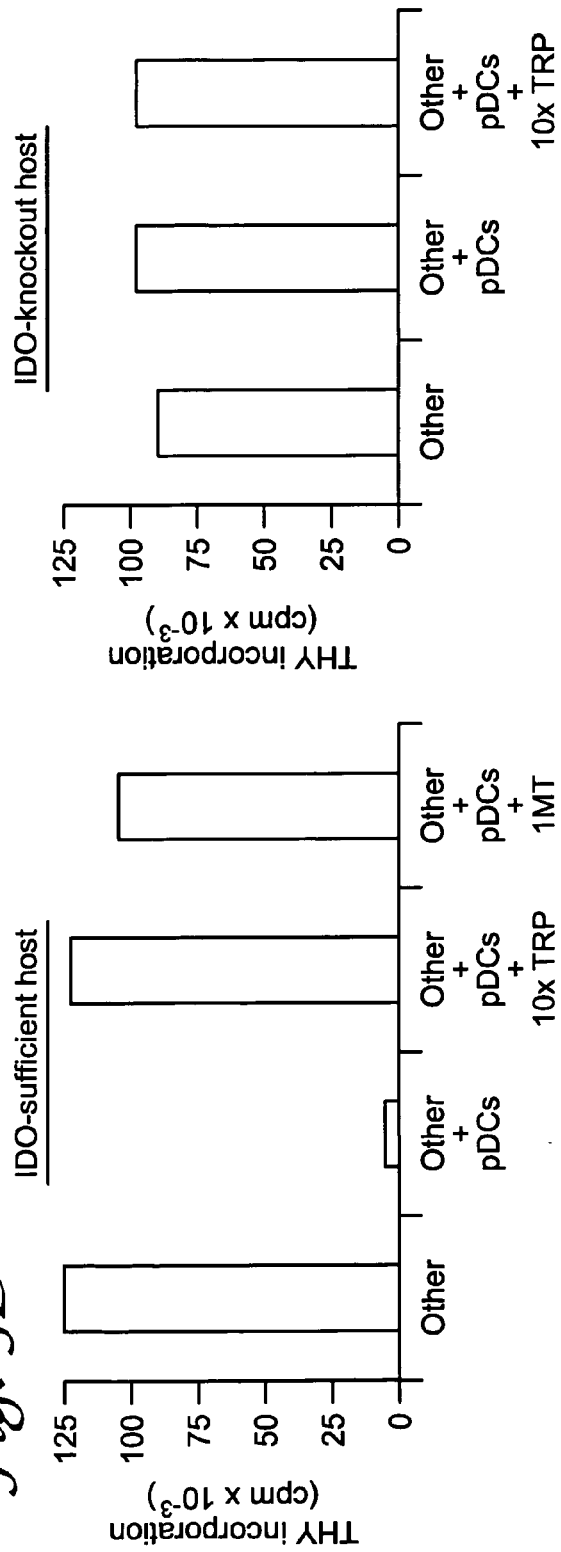

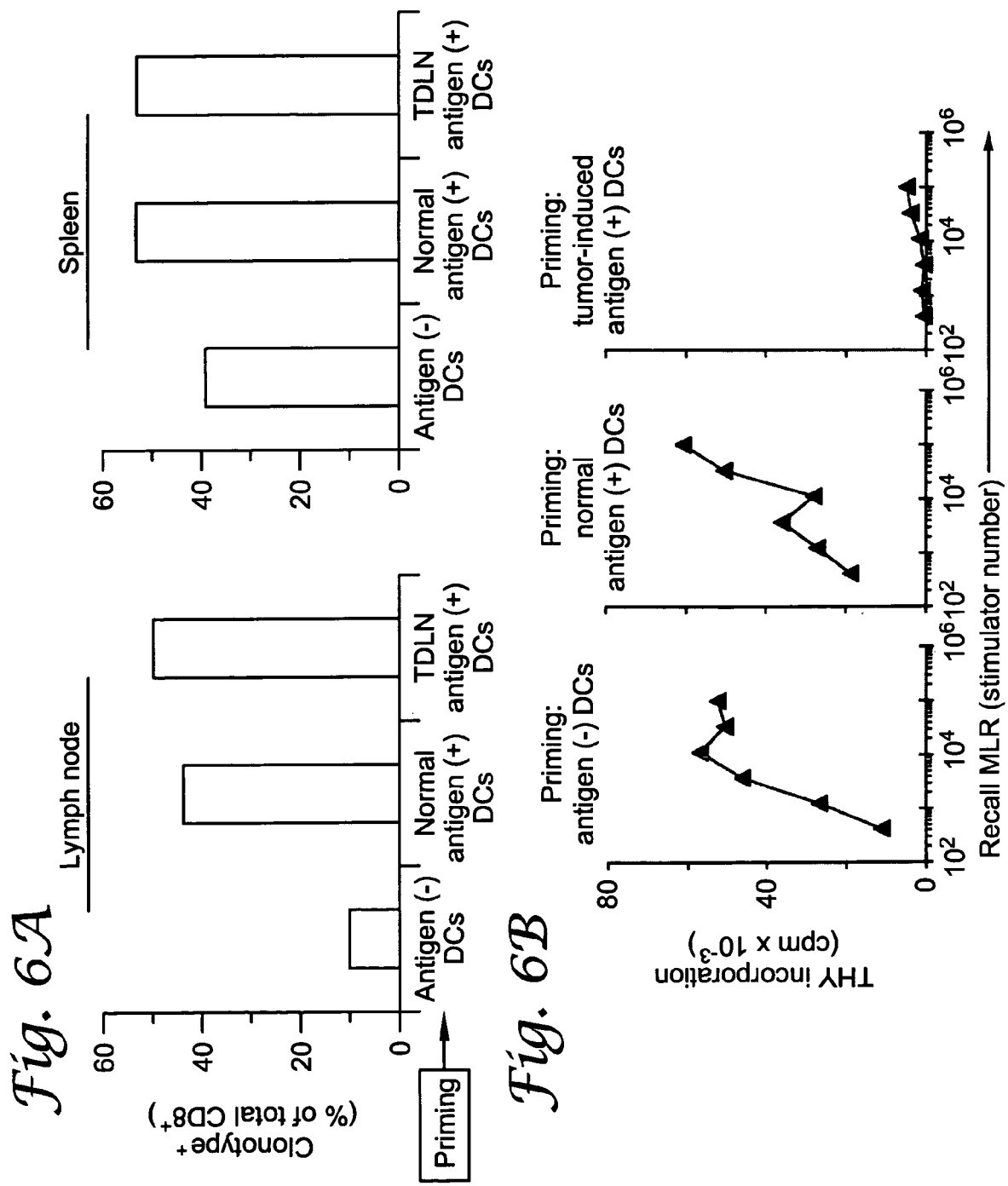

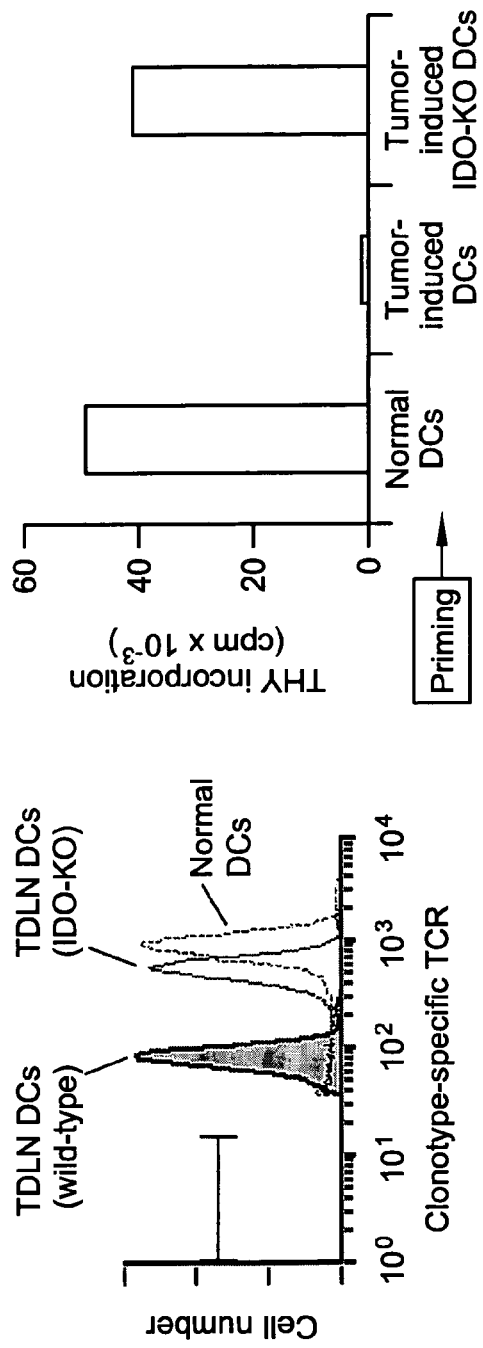
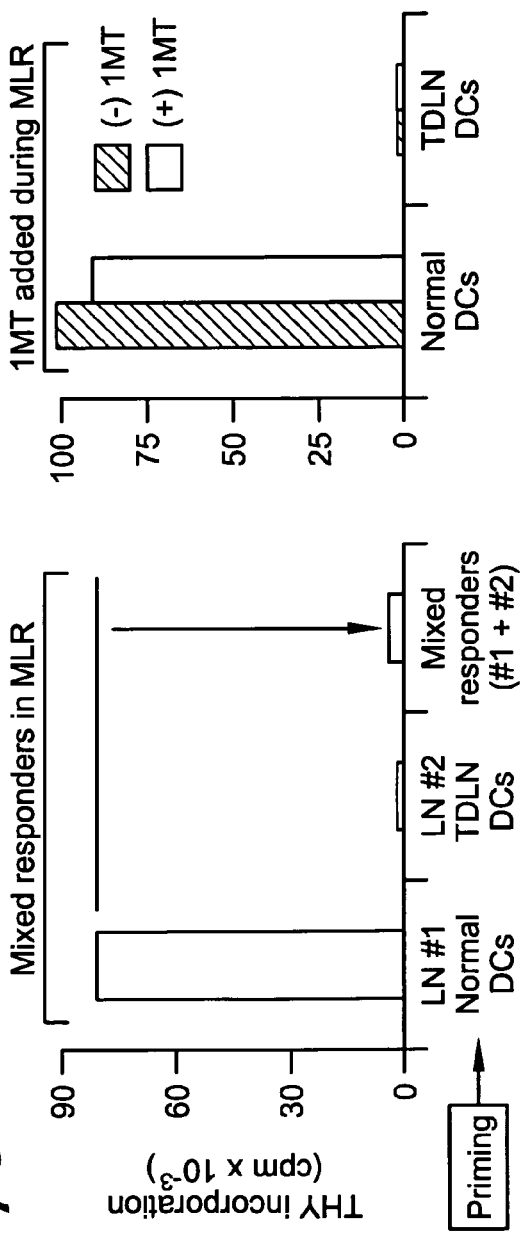
Fig. 7B
Fig. 7C

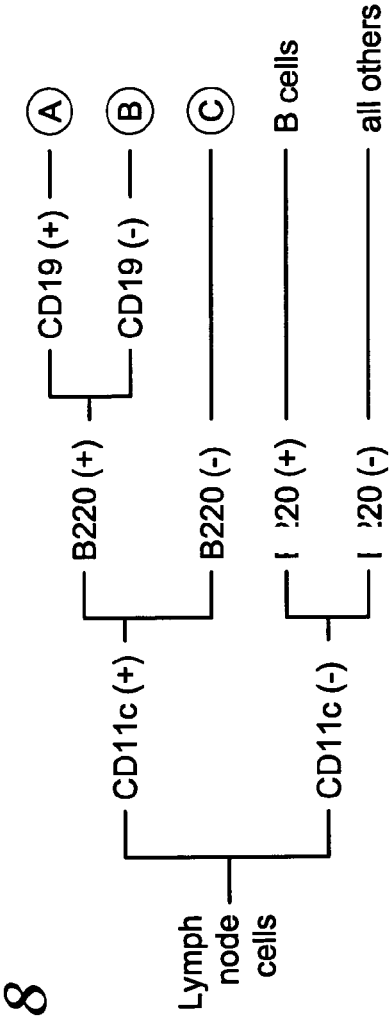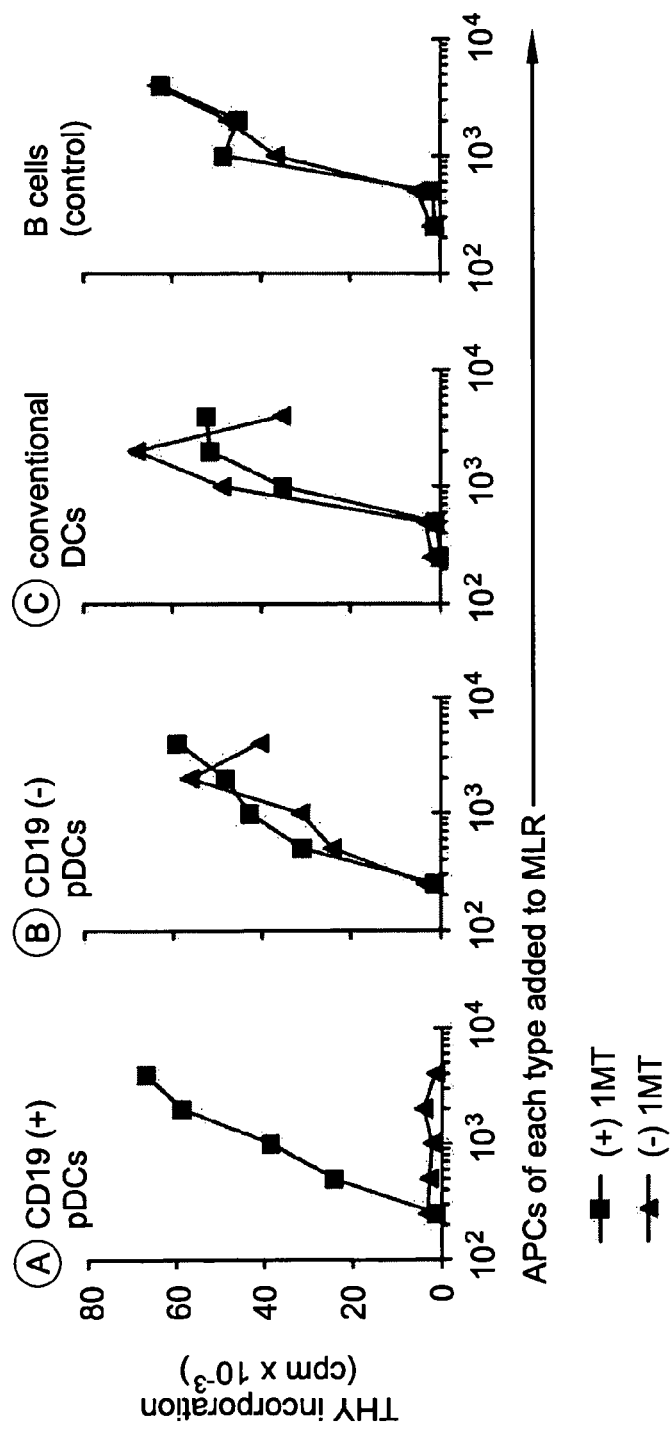
Fig. 8

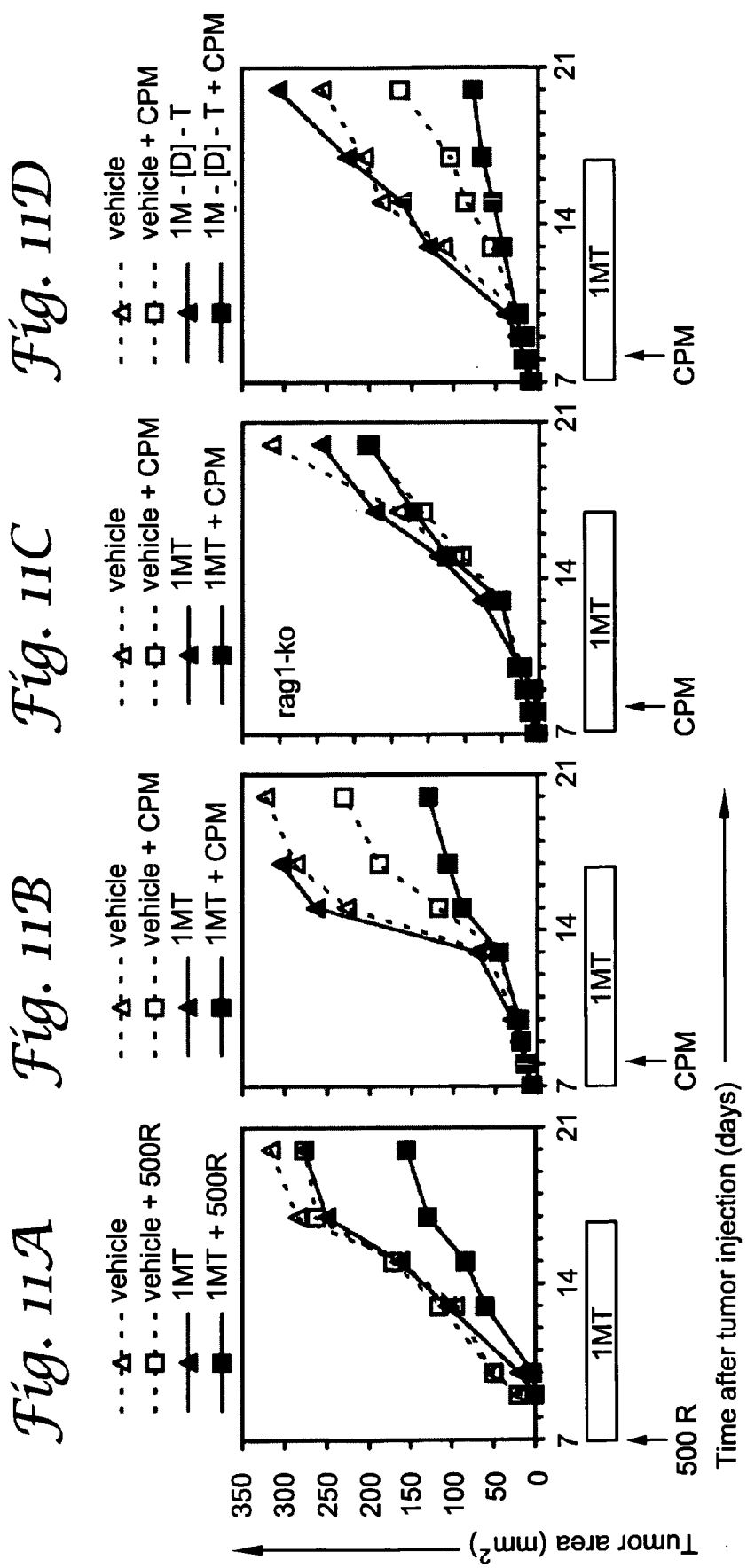

```
                            SEQUENCE LISTING

<160> NUMBER OF SEQ ID NOS: 7

<210> SEQ ID NO 1
<211> LENGTH: 18
<212> TYPE: PRT
<213> ORGANISM: Homo sapiens

<400> SEQUENCE: 1

Leu Ile Glu Ser Gly Gln Leu Arg Glu Arg Val Glu Lys Leu Asn Met
1               5                   10                  15

Leu Cys

<210> SEQ ID NO 2
<211> LENGTH: 19
<212> TYPE: DNA
<213> ORGANISM: artificial sequence
<220> FEATURE:
<223> OTHER INFORMATION: synthetic oligonucleotide primers
```

-continued

```
<400> SEQUENCE: 2
gatgacgcag ataatgttt                                                    19

<210> SEQ ID NO 3
<211> LENGTH: 19
<212> TYPE: DNA
<213> ORGANISM: artificial sequence
<220> FEATURE:
<223> OTHER INFORMATION: synthetic oligonucleotide primers

<400> SEQUENCE: 3
tctcctttat gtcacgaac                                                    19

<210> SEQ ID NO 4
<211> LENGTH: 20
<212> TYPE: DNA
<213> ORGANISM: artificial sequence
<220> FEATURE:
<223> OTHER INFORMATION: synthetic oligonucleotide primers

<400> SEQUENCE: 4
ggcacctatt attgtctccg                                                   20

<210> SEQ ID NO 5
<211> LENGTH: 18
<212> TYPE: DNA
<213> ORGANISM: artificial sequence
<220> FEATURE:
<223> OTHER INFORMATION: synthetic oligonucleotide primers

<400> SEQUENCE: 5
gggtcagtca ttcgcttc                                                     18

<210> SEQ ID NO 6
<211> LENGTH: 21
<212> TYPE: DNA
<213> ORGANISM: artificial sequence
<220> FEATURE:
<223> OTHER INFORMATION: synthetic oligonucleotide primers

<400> SEQUENCE: 6
gcatagtgtc tacaggctcc g                                                 21

<210> SEQ ID NO 7
<211> LENGTH: 18
<212> TYPE: DNA
<213> ORGANISM: artificial sequence
<220> FEATURE:
<223> OTHER INFORMATION: synthetic oligonucleotide primers

<400> SEQUENCE: 7
gatgggttcc gtggtggt                                                     18
```

USE OF INHIBITORS OF INDOLEAMINE-2,3-DIOXYGENASE IN COMBINATION WITH OTHER THERAPEUTIC MODALITIES

This application claims the benefit of U.S. Provisional Application Ser. No. 60/459,489, filed Apr. 1, 2003, and U.S. Provisional Application Ser. No. 60/538,647, filed Jan. 22, 2004. Both of these provisional applications are incorporated herein by reference in their entireties.

GOVERNMENT FUNDING

The present invention was made with government support under Grant Nos. K08 HL03395, 1R01CA103320, and 1R01CA096651, awarded by the National Institutes of Health. The Government has certain rights in this invention.

BACKGROUND

The adaptive immune system must tailor the T cell repertoire so as not to respond to self-antigens. The classical model (reviewed by Nossal in *Cell* 1994; 76:229-239) holds that autoreactive T cell clones are deleted in the thymus via a process of negative selection in which encounter with antigen at the immature thymocyte stage triggers apoptosis, resulting in clonal deletion. Although the thymus undoubtedly provides a major site of negative selection, there are difficulties with this model. First, it would seem unlikely that every developing T cell could be exposed to every self-antigen during its relatively brief transit through the thymus. Second, autoreactive T cells are empirically found in the peripheral blood of normal, healthy hosts (Steinman, *Cell* 1995; 80:7-10). This suggests the existence of additional means of tailoring the T cell repertoire after the T cells have left the thymus, a process designated as peripheral tolerance.

The immune system of a tumor-bearing host often fails to respond protectively against tumor antigens. Functionally, the host is tolerant toward the tumor (Smyth et al., *Nat. Immunol.*, 2001; 2:293). This is not due to a peculiarity of tumor antigens, because even highly immunogenic viral proteins become tolerizing when introduced on tumor cells (Staveley-O'Carroll et al., *Proc. Natl. Acad. Sci. USA*, 1998; 95:1178). Tumor-induced tolerance is actively created and is maintained in an ongoing fashion (Sotomayor et al., *Blood*, 2001; 98:1070; and Cuenca et al., *Cancer Res.*, 2003; 63:9007). Thus, tumors represent a striking and biologically significant example of acquired peripheral tolerance (Pardoll, *Ann. Rev. Immunol.*, 2003; 21:807). The molecular mechanisms by which this tolerance arises are currently unclear. This tolerance allows tumors to escape the host's normal immune surveillance and imposes a fundamental barrier to successful clinical immunotherapy.

SUMMARY OF THE INVENTION

The present invention includes a method of treating a subject with a cancer or an infection, the method including administering to the subject an inhibitor of indoleamine-2,3-dioxygenase in an amount effective to reverse indoleamine-2,3-dioxygenase-mediated immunosuppression, and administering at least one additional therapeutic agent wherein the administration of the inhibitor of indoleamine-2,3-dioxygenase and the at least one additional therapeutic agent demonstrate therapeutic synergy. In some embodiments of the method, the indoleamine-2,3-dioxygenase-mediated immunosuppression is meditated by an antigen-presenting cell (APC).

In some embodiments of the method of the present invention, at least one additional therapeutic agent is an antineoplastic chemotherapy agent, including, for example, cyclophosphamide, methotrexate, fluorouracil, doxorubicin, vincristine, ifosfamide, cisplatin, gemcytabine, busulfan, ara-C, or combinations thereof.

In some embodiments of the method of the present invention, the additional therapeutic agent is radiation therapy, including, for example, localized radiation therapy delivered to the tumor and total body irradiation.

In some embodiments of the method of the present invention, the inhibitor of indoleamine-2,3-dioxygenase may be 1-methyl-tryptophan, β-(3-benzofuranyl)-alanine, β-(3-benzo(b)thienyl)-alanine, or 6-nitro-D-tryptophan. In some embodiments, the inhibitor of indoleamine-2,3-dioxygenase is a D isomer of an inhibitor of indoleamine-2,3-dioxygenase, including, for example, the D isomer of 1-methyl-tryptophan, the D isomer of β-(3-benzofuranyl)-alanine, the D isomer of β-(3-benzo(b)thienyl)-alanine, or the D isomer of 6-nitro-D-tryptophan.

In some embodiments of the method of the present invention, the cancer is melanoma, colon cancer, pancreatic cancer, breast cancer, prostate cancer, lung cancer, leukemia, brain tumors, lymphoma, sarcoma, ovarian cancer, or Kaposi's sarcoma.

In some embodiments of the method of the present invention, the method further includes bone marrow transplantation or peripheral blood stem cell transplantation.

In some embodiments of the method of the present invention, the infection may be a viral infection, infection with an intracellular parasite, or an infection with an intracellular bacteria. In some embodiments, the viral infection is human immunodeficiency virus or cytomegalovirus. In some embodiments, the intracellular parasite may be *Leishmania donovani, Leishmania tropica, Leishmania major, Leishmania aethiopica, Leishmania mexicana, Plasmodium falciparum, Plasmodium vivax, Plasmodium ovale*, or *Plasmodium malariae*. In some embodiments, the intracellular bacteria may be *Mycobacterium leprae, Mycobacterium tuberculosis, Listeria monocytogenes*, or *Toxplasma gondii*.

In some embodiments of the method of the present invention, the additional therapeutic agent is a vaccine. In some embodiments the vaccine may be an anti-viral vaccine, including, for example, a vaccine is against HIV. In some embodiments the vaccine is against tuberculosis or malaria. In some embodiments the vaccine is a tumor vaccine, including, for example, a melanoma vaccine. In some embodiments the tumor vaccine includes genetically modified tumor cells or a genetically modified cell line, including genetically modified tumor cells or genetically modified cell line that have been transfected to express granulocyte-macrophage stimulating factor (GM-CSF). In some embodiments the vaccine includes one or more immunogenic peptides. In some embodiments the vaccine includes dendritic cells.

In some embodiments of the method of the present invention, the additional therapeutic agent is a cytokine, including, for example granulocyte-macrophage colony stimulating factor (GM-CSF) or flt3-ligand.

The present invention also includes a method of augmenting the rejection of tumor cells in a subject, the method including administering an inhibitor of indoleamine-2,3-dioxygenase and administering at least one antineoplastic chemotherapeutic agent, wherein the rejection of tumor cells obtained by administering both the inhibitor of indoleamine-2,3-dioxygenase and the antineoplastic chemotherapeutic agent is greater than that obtained by administering either the inhibitor of indoleamine-2,3-dioxygenase or the antineoplastic chemotherapeutic agent alone.

The present invention also includes a method of treating cancer, the method including administering an inhibitor of indoleamine-2,3-dioxygenase and administering at least one antineoplastic chemotherapeutic agent, wherein cancer survival rate observed by administering both the inhibitor of indoleamine-2,3-dioxygenase and the antineoplastic chemotherapeutic agent is greater than the cancer survival rate observed by administering either the inhibitor of indoleamine-2,3-dioxygenase or the antineoplastic chemotherapeutic agent alone.

The present invention also includes a method of reducing tumor size or slowing tumor growth, the method including administering an inhibitor of indoleamine-2,3-dioxygenase and administering at least one antineoplastic chemotherapeutic agent, wherein the tumor size or tumor growth observed with the administration of both the inhibitor of indoleamine-2,3-dioxygenase and the antineoplastic chemotherapeutic agent is less than the tumor size or tumor growth observed with the administration of either the inhibitor of indoleamine-2,3-dioxygenase or the antineoplastic chemotherapeutic agent alone.

The present invention also includes a method of augmenting rejection of tumor cells in a subject, the method including administering an inhibitor of indoleamine-2,3-dioxygenase and administering radiation therapy, wherein the rejection of tumor cells wherein the rejection of tumor cells obtained by administering both the inhibitor of indoleamine-2,3-dioxygenase and the radiation therapy is greater than that obtained by administering either the inhibitor of indoleamine-2,3-dioxygenase or the radiation therapy alone.

The present invention also includes a method of treating cancer, the method including administering an inhibitor of indoleamine-2,3-dioxygenase and administering radiation therapy, wherein the cancer survival rate observed by administering both the inhibitor of indoleamine-2,3-dioxygenase and radiation therapy is greater than the cancer survival rate observed by administering either the inhibitor of indoleamine-2,3-dioxygenase or radiation therapy alone.

The present invention also includes a method of reducing tumor size or tumor growth, the method including administering an inhibitor of indoleamine-2,3-dioxygenase and administering radiation therapy, wherein the tumor size or tumor growth observed with the administration of both the inhibitor of indoleamine-2,3-dioxygenase and radiation therapy is less than the tumor size or tumor growth observed with the administration of either the inhibitor of indoleamine-2 3-dioxygenase or radiation therapy alone.

The present invention also includes a method of treating an infection, the method including administering an inhibitor of indoleamine-2,3-dioxygenase and administering at least one additional therapeutic agent, wherein a symptom of infection observed after administering both the inhibitor of indoleamine-2,3-dioxygenase and the additional therapeutic agent is improved over the same symptom of infection observed after administering either the inhibitor of indoleamine-2,3-dioxygenase or the additional therapeutic agent alone. IN some embodiments, the additional therapeutic agent is an antiviral agent, an antibiotic, an antimicrobial agent, a cytokine, or a vaccine. In some embodiments, the a symptom of infection observed may be reduction in viral load, increase in $CD4^+$ T cell count, decrease in opportunistic infections, increased survival time, eradication of chronic infection, or a combination thereof.

The present invention also includes a method of treating a subject receiving a bone marrow transplant or peripheral blood stem cell transplant by administering an inhibitor of indoleamine-2,3-dioxygenase. In some embodiments of the method, the inhibitor of indoleamine-2,3-dioxygenase is administered in an amount effective to increase the delayed type hypersensitivity reaction to tumor antigen, delay the time to relapse of post-transplant malignancy, increase relapse free survival time post-transplant, and/or increase long-term post-transplant survival. In some embodiments of the method the inhibitor of indoleamine-2,3-dioxygenase is administered prior to full hematopoetic reconstitution.

Definitions

As used herein, the term "subject" represents an organism, including, for example, an animal. An animal includes, but is not limited to, a human, a non-human primate, a horse, a pig, a goat, a cow, a rodent, such as, but not limited to, a rat or a mouse, or a domestic pet, such as, but not limited to, a dog or a cat.

As used herein "in vitro" is in cell culture, "ex vivo" is a cell that has been removed from the body of a subject, and "in vivo" is within the body of a subject.

As used herein, "treatment" or "treating" include both therapeutic and prophylactic treatments.

Unless otherwise specified, "a," "an," "the," and "at least one" are used interchangeably and mean one or more than one.

BRIEF DESCRIPTION OF THE FIGURES

In FIG. 1A human monocytes were analyzed without culture (fresh, n=12); cultured for 7 days in MCSF with IFN-γ added for the final 18 hours (Mφ+IFNγ, n=8); or cultured in granulocyte-macrophage CSF+IL-4 (DCs) in BCS medium (n=34) or SFM (n=24). Upper row represents IDO versus CD123; lower row represents CCR6 versus CD123 on the same triple-stained cells. Negative control for IDO staining was the primary antibody preadsorbed with the immunizing peptide. FIG. 1B represents immunophenotype of nonadherent ($IDO^+$) dendritic cells (DCs)(dark lines) versus adherent cells (light lines) from SFM cultures, matured with tumor necrosis factor-α/IL-1β/IL-6/prostaglandin $E_2$. FIG. 1C represents morphology of adherent (left) and nonadherent (right) cells (cytocentrifuge preparations, Wright's stain; scale bar, 10 μm). FIG. 1D represents immunophenotype of MCSF-derived Mφs, gated separately on the CD123 (dark lines) and CD123NEG (light lines) populations.

FIGS. 2A-2I. Effect of DC maturation on IDO expression. In FIG. 2A monocyte-derived Mφs were analyzed with (left) or without (right) IFN-γ added for the final 18 hours. FIG. 2B represents DCs (BCS system), with or without IFN-γ for 18 hours. FIG. 2C represents DCs matured with antibody to CD40 on days 5 to 7, with or without IFN-γ for 18 hours. FIG. 2D represents DCs matured with antibody to CD40 on days 5 to 7, with or without IFN-γ for 18 hours, and with 11-10 added during the maturation step. FIG. 2E presents functional enzymatic activity. Depletion of tryptophan from the culture medium (expressed as a percentage of the starting tryptophan concentration in fresh medium, 25 μM) by DCs with or without IFN-γ for 18 hours. Immature DCs (iDC), CD40-matured DCs (mDC), and CD40-matured DCs in the presence of IL-10 (mDC/IL10) were generated, with or without IFN-γ activation, as in FIGS. 2B-2D. In FIG. 2F allogeneic MLRs using enriched $IDO^+$DCs (nonadherent cells, SFM system, without added IFN-γ). DCs were either immature or matured with antibody to CD40. APC/T cell ratio was 1:20. White bars, without 1 MT; black bars, with 1 MT. FIG. 2G presents MLR with a titration of enriched IDO+ DCs (nonadherent cells, SFM system, no IFN-γ) matured with cytokine-containing supernatant from activated monocytes. Similar results were observed when DCs were matured with the cytokine regimen used in FIG. 1B. Responder T cell number, $5\times10^5$ (highest APC/T cell ratio was 1:10) without 1 MT (triangles), and with 1 MT (squares). FIG. 2H represents immunomagnetic sorting of CD 123+ DCs from a mixed DC preparation (BCS system, tumor necrosis factor-α (TNF-α) matured, no IFN-γ). Unfractionated (pre-sort), sorted CD 123+ cells (greater than 80% purity), and CD123-depleted cells. APC/T cell ratio was 1:10. White bars, with 1 MT (DL-racemic mixture); black bars, without 1 MT. FIG. 2I represents adherent cells (less than 10% IDO+) from SFM cultures, matured with TNFα/IL1β/IL6/prostaglandin $E_2$, used as stimulators in allogeneic MLRs. White squares are without 1 MT, black squares are with 1 MT. For comparison, nonadherent (IDO+) cells from the same culture are shown without 1 MT (triangles). Representative of six experiments.

FIGS. 3A-3E. Validation of polyclonal anti-IDO antibody. FIG. 3A presents THP1 cell lysates, analyzed by western blot for IDO (12% SDS-PAGE gel, reducing conditions, blotted to PVDF membrane, blocked with 10% dry milk in 0.25% Tween-20 Tris-buffered saline). In lane 1, anti-IDO primary antibody (10 ng/ml) was detected with anti-rabbit peroxidase secondary antibody (1:2000, Santa Cruz Biotechnology) and visualized by chemiluminescence (ECL, Amersham). Lane 2, as in lane 1, but with 1 ug/ml immunizing peptide added to the primary antibody before use. FIG. 3B presents MCSF-derived Mϕs IFNγ×18 hours, analyzed by western blot as in FIG. 3A. FIG. 3C represents immunoprecipitation from THP1 cell lysates. Cells were lysed with buffer (150 mM NaCl, 0.5% NP-40, 1 mM dithiothreitol, 2 mM EDTA, 50 mM Tris pH 7.5, plus inhibitors of proteases and phosphatases) and lysates incubated with anti-IDO antibody (1 ug, lane 1), or antibody plus immunizing peptide (lane 2). Immune-complexes were precipitated with protein G-agarose (Life Technologies), resolved by SDS-PAGE under reducing conditions, and analyzed by silver stain. A single specific 45 kD band (arrow) was resolved just below the heavy chain band of the immunoprecipitating antibody, IgGH). FIG. 3D presents 2D-gel electrophoresis followed by western blotting with anti-IDO antibody revealed a single major immunoreactive species in resting Mϕs (left panel). Following activation with IFNγ for 18 hours (right panel) two additional species (arrows) were detected by the anti-IDO antibody. MCSF-derived Mϕs were lysed with 8M urea and 4% CHAPS in Tris buffer, and 50 ug of protein subjected to first-dimension isoelectric focusing (Protean IEF system, BioRad) using pH 3-10 ampholyte strips. Second-dimension reducing SDS-PAGE was performed (Mini-Protean system. BioRad) and gels were transferred to PVDF membrane and analyzed by western blot using anti-IDO antibody, as in FIG. 3A. FIG. 3E presents flow-cytometric analysis of MCSF-derived Mϕs activated with IFNγ for 18 hours. Cells stained with anti-IDO antibody are shown on the left, while the same cells stained with antibody pre-adsorbed with the immunizing peptide are shown on the right.

FIGS. 4A-4B. Simultaneous analysis of T cell proliferation by thymidine incorporation and tryptophan concentration in the medium from the same allogeneic MLR culture. FIG. 4A presents an analysis of T cell proliferation by thymidine incorporation from the allogeneic MLR culture (day 3 of activation). FIG. 4B presents an analysis of tryptophan concentration in the medium by HPLC from the allogeneic MLR culture (day 3 of activation). Stimulators were IDO+ (nonadherent) DCs from SFM cultures. The ratio of DCs to T cells was low (1:500) in order to approximate the density of APCs expected in normal lymphoid tissue. Under these condition there is little depletion of tryptophan from the medium (starting tryptophan concentration in RPMI medium of 25 uM), and the concentration of tryptophan remains well above the level required to support T cell proliferation, indicated by the arrow in FIG. 4B. Nevertheless, there was still a significant component of IDO-mediated suppression, shown by the 3-fold enhancement of proliferation seen when 1 MT was added (FIG. 4A).

FIGS. 5A-5D. Suppression of T cell responses by tumor-draining LN cells. FIG. 5A shows dominant suppressor cells in TDLNs. Cells from tumor-draining LN (DLN) and contralateral LNs (CLN) were harvested from mice with B78H1.GMCSF tumors on day 14 and used as stimulators in MLRs (the number of stimulator cells is shown in parentheses). Responder cells ($5\times10^4$ BM3 T cells) were the same in all groups. The left panel shows the absence of response when DLN cells were used as stimulators. The right panel shows mixing experiments, revealing that the absence of response to the DLN cells was due to a dominant suppressor activity present in these cells. In all experiments, response to CLN stimulators was quantitatively comparable to control stimulators (normal LN cells from non-tumor-bearing mice). FIG. 5B shows suppressive pDCs and Tregs in tumor-draining LNs. TDLN cells were sorted by 4-color flow cytometry into CD11c+B220+ pDCs (1-2%) and CD4+CD25+ Tregs (2-3%), plus a third population of all other cells (95-97%). Each fraction was used as stimulator cells in parallel MLRs, using the number of cells that would have been present in $5\times10^4$ of the original TDLN population. All MLRs received $5\times10^4$ BM3 responders. FIG. 5C shows suppression by pDCs is mediated by IDO. TDLN cells were sorted into pDCs, Tregs, and the non-suppressive "all other" cells, as in the previous panel (Tregs were discarded). Each population was used as stimulators for BM3 responders, in duplicate MLRs with and without the IDO inhibitor 1 MT. The left panel shows TDLN cells from a normal (IDO-sufficient) host show dominant suppression by pDCs that is reversed by 1 MT (arrows). The right panel shows tumor-draining LN cells from IDO-knockout host, showing no suppression, and no effect of 1 MT. FIG. 5D shows excess L-tryptophan (250 uM, 10×) abrogates suppression by pDCs in a fashion comparable to 1 MT. Experimental design, as in previous panel. There was no effect of 10× L-tryptophan when TDLN cells were derived from IDO-knockout mice.

FIGS. 6A-6C. Adoptive transfer of DCs from TDLNs creates profound local immunosuppression in naive hosts. FIG. 6A shows antigen-driven recruitment of BM3 T cells into the LNs draining the site of adoptive transfer. CD11c+DCs were purified from TDLNs (C57BL/6 hosts) and injected subcutaneously into naive CBA mice. Recipient mice had previously received $4\times10^7$ naive BM3 splenocytes injected intravenously ("CBA+BM3" mice). Control CBA+BM3 recipients received normal CD11c+ DCs prepared from LNs of C57BL/6 mice without tumors ("Normal antigen(+)"), or from LNs of syngeneic CBA mice ("Antigen(−)"). After 10 days, the LNs draining the site of the DC injection were harvested and stained for clonotype-specific BM3 TCR expression (left panel). Spleens from each animal were similarly stained (right panel). The number of clonotype-positive CD8+ cells, expressed as a percentage of total CD8+ T cells, are shown for each of the 3 different DC priming groups. Each bar represents 4 pooled nodes. The absolute number of LN and spleen cells was not significantly different between the 3 groups. FIG. 6B shows unresponsiveness of T cells primed with DCs from TDLNs. Recipient CBA+BM3 mice were primed with the 3 different types of DCs described in FIG. 6A. After 10 days, LN cells draining the site of DC injection were harvested and used as responder cells in recall MLRs. A fixed number of the primed responder cells from each group ($1\times10^5$) were tested against a titration of stimulator cells (irradiated normal C57BL/6 splenocytes), as shown. In FIG. 6C recipient CBA+BM3 mice were primed with DCs from TDLNs, or with DCs from normal C57BL/6 LNs. During the 10 day priming exposure, half of the recipient mice received 1-methyl-D-tryptophan (5 mg/day) via implantable pellets; the group not labeled as receiving 1 MT received vehicle pellets alone. After 10 days, responder T cells were harvested from LNs draining the site of each DC injection, and tested for responsiveness in recall MLRs against a titration of irradiated C57BL/6 splenocytes. All recipients were pre-loaded with identical aliquots of BM3, and all recall MLRs were performed in parallel with identical stimulators, so that comparison would be meaningful between groups.

FIGS. 7A-7C. Response to antigen introduced on IDO+ DCs. FIG. 7A shows systemic awareness of antigen introduced on TDLN DCs is revealed by TCR down regulation in spleen. The upper panel represents in vitro stimulation of BM3 T cells by cells from TDLN caused down-regulation of TCR on BM3 T cells (detected by clonotype-specific antibody, gated on CD8+ cells). TCR down regulation was not induced by normal C57BL/6 LN stimulators. The lower panels represent adoptive transfer of CD11c$^+$ DCs was performed as in FIG. 6A. After 10 days, LNs and spleen were harvested from recipient CBA+BM3 mice stained for BM3 clonotype-specific TCR expression. The level of TCR expression is shown, gated on the clonotype-positive CD8$^+$ BM3 cells in LN and spleen. Each histogram represents 4 pooled samples. FIG. 7B demonstrates TCR down regulation is dependent on functional IDO in the transferred DCs. B78H1× GM-CSF tumors were grown in IDO-knockout mice (C57BL/6 background). DCs were sorted from TDLNs and used to prime recipient CBA+BM3 mice; control recipients received TDLN DCs from wild-type C57BL/6 hosts, or normal C57BL/6 DCs. In the left panel, TCR expression on CD8+ BM3 T cells (measured as in FIG. 7A) showed little down regulation in the absence of IDO. Representative data from recipient LNs are shown; comparable results were obtained with T cells from spleen. In other experiments, administration of 1 MT at the time of adoptive transfer also significantly reduced TCR down regulation by TDLN DCs. The right panel confirms that IDO-deficient TDLN DCs also did not suppress BM3 responses in recall MLRs. FIG. 7C represents creation of secondary, IDO-independent immunosuppression following adoptive transfer. CBA+BM3 recipients were primed with DCs from normal LNs (group #1), or with DCs from TDLNs (group #2), both from C57BL/6 mice. After 10 days, the recipient LNs draining the site of adoptive transfer were tested in recall MLRs. In the left panel, mixing experiments showed that the lack of reactivity in T cells from mice receiving TDLN DCs was dominant, indicating active suppression. In the right panel, T cell proliferation was not restored by 1 MT added to the MLR assays, suggesting that recipients had developed secondary, IDO-independent mechanisms of immunosuppression.

FIG. 8. IDO-mediated suppressor activity segregates with the CD19$^+$ subset of pDCs. Cells from TDLNs were sorted into five populations based on expression of CD11c, B220, and CD19, as shown in the schematic at top. The three CD11c$^+$ DC fractions (labeled "A," "B," and "C") were used as stimulators in MLRs. Control MLRs were stimulated by B cells from the same LN. Each MLR contained $2\times10^5$ BM3 responder cells, plus a titration of each type of stimulator cell (responders were in excess, stimulators were limiting). Parallel titrations were performed with and without 1 MT, to demonstrate the IDO-mediated component of suppression. Only the CD19$^+$ pDCs (fraction A) mediated significant suppression.

In FIG. 9A, TDLNs were stained by 4-color flow cytometry for CD11c versus CD19 versus the various markers shown. The total CD11c$^+$ DC population was gated into CD19$^+$ and CD19$^{NEG}$ subsets, and the expression of each marker shown for the two populations. The isotype-matched negative control for each marker (gated on CD11c$^+$ cells) is shown as the horizontal bar. Each histogram is representative of 4-12 experiments with each marker. In FIG. 9B, cells from TDLNs were sorted into 5 fractions, as shown in FIG. 8. RNA from each fraction was analyzed by real-time quantitative RT-PCR. RNA was added based on pre-determined equivalent amounts of gamma-actin message. Gels show the expected molecular weight band for CD19, pax5, and γ-actin after 27 cycles of amplification. The numbers below each band give the relative amount of message, quantitated against a standard curve of spleen RNA, normalized to the sorted B cell fraction (arbitrarily set equal to 100%). FIG. 6C represents expression of maturation markers on CD 19$^+$ versus CD 19$^{NEG}$ subsets of DCs from TDLNs, gated as in FIG. 9A. Maturation markers in the CD19$^{NEG}$ population varied from experiment to experiment (an immature example is shown for comparison), but the CD19$^+$ population was always mature. FIG. 9D represents expression of cell-surface markers CD123 (IL3R-a) and CCR6 on the CD19$^+$ and CD19$^{NEG}$ DC subsets. Cells were analyzed from TDLNs and from contralateral LNs of the same animals, as shown.

FIGS. 11A-11D. Administration of 1 -MT enhances immune-mediated host anti-tumor effect when administered with radiation or cyclophosphamide. Mice were injected subcutaneously (SQ) with $4\times10^4$ B16F10 cells. In FIG. 11A 1 MT (20 mg/day of a DL racemic mixture) was administered SQ by continuous-release copolymer pellets, with or without 500 cGy of total-body γ-irradiation. Control mice received vehicle pellets without drug. In FIG. 11B 1 MT was administered with cyclophosphamide (CPM)(150 mg/kg, one dose). FIG. 11C represents 1 MT and cyclophosphamide in rag1-knockout hosts. FIG. 11D represents the more potent pure D-isomer of 1 MT, given 5 mg/day, with cyclophosphamide.

DETAILED DESCRIPTION OF PREFERRED EMBODIMENTS

Figure 1A:
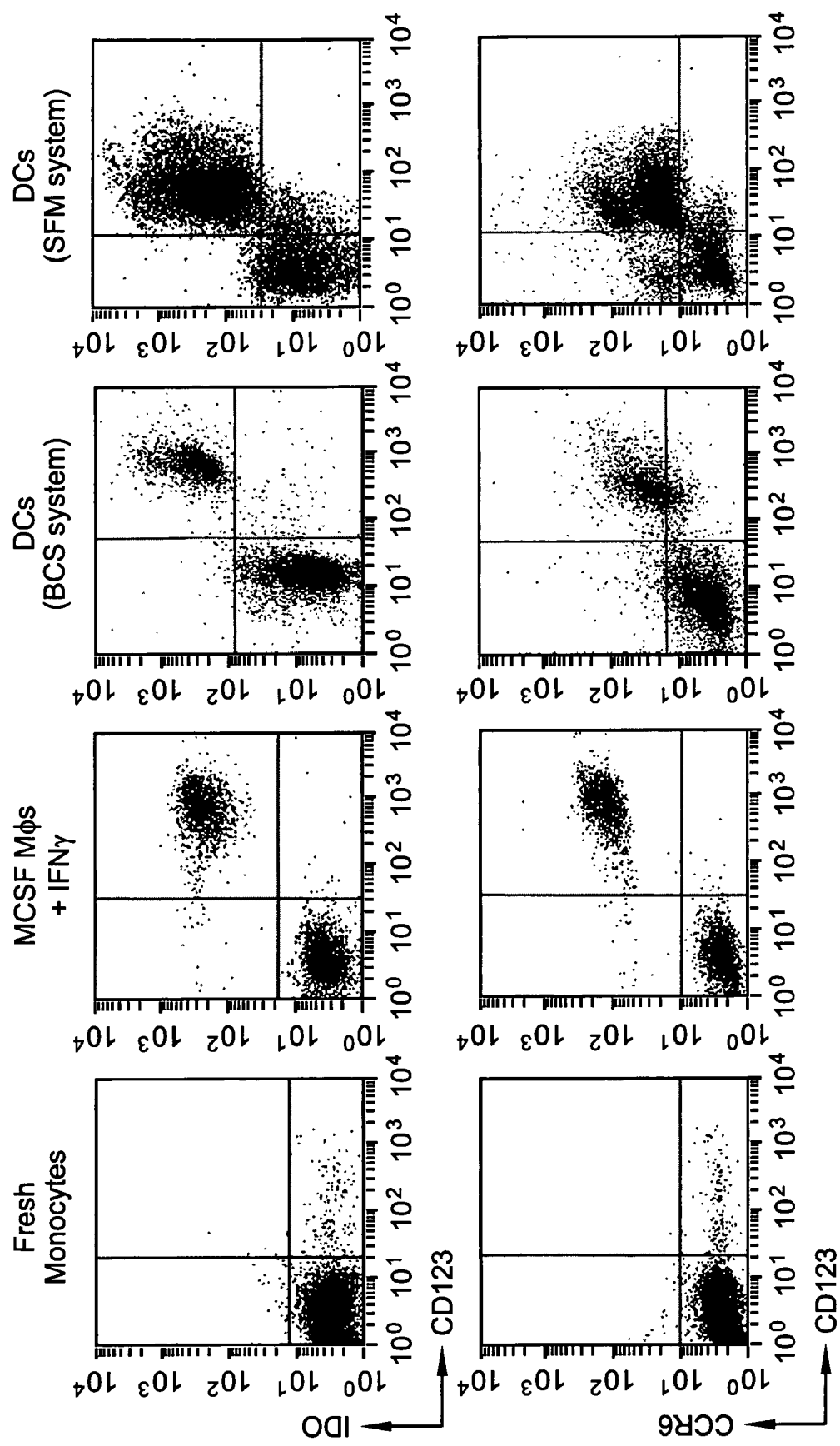
FIGS. 1A-1D. Expression of indoleamine 2,3-dioxygenase (IDO) by antigen-presenting cells (APC).

A newly recognized molecular mechanism contributing to peripheral immune tolerance is the immunoregulatory enzyme indoleamine 2,3-dioxygenase (IDO). Cells expressing the tryptophan-catabolizing enzyme IDO are capable of inhibiting T cell proliferation in vitro and reducing T cell immune responses in vivo (U.S. Pat. Nos. 6,451,840 and 6,482,416; Munn et al., *Science* 1998; 281:1191; Munn et al., *J. Exp. Med.* 1999; 189:1363; Hwu et al., *J. Immunol.* 2000; 164:3596; Mellor et al., *J. Immunol.* 2002; 168:3771; Grohmann et al., *J. Immunol.* 2001; 167:708; Grohmann et al., *J. Immunol.* 2001; 166:277; and Alexander et al., *Diabetes* 2002; 51:356).

IDO degrades the essential amino acid tryptophan (for reviews see Taylor et al., *FASEB Journal* 1991; 5:2516-2522; Lee et al., *Laboratory Investigation*, 2003; 83:1457-1466; and Grohmann et al., *Trends in Immunology* 2003; 24:242-248). Expression of IDO by human monocyte-derived macrophages (Munn et al., *J. Exp. Med.* 1999; 189:1363-1372), human dendritic cells (Munn et al., *Science* 2002; 297:1867-1870 and Hwu et al., *J. Immunol.* 2000; 164:3596-3599), and mouse dendritic cells (Mellor et al., *J. Immunol.* 2003; 171: 1652-1655) allows these different antigen-presenting cells (APCs) to inhibit T cell proliferation in vitro. In vivo, IDO participates in maintaining maternal tolerance toward the antigenically foreign fetus during pregnancy (Munn et al., *Science* 1998; 281:1191-1193).

IDO has also been implicated in maintaining tolerance to self antigens (Grohmann et al., *J. Exp. Med.* 2003; 198:153-160), in suppressing T cell responses to MHC-mismatched organ transplants (Miki et al., *Transplantation Proceedings* 2001; 33:129-130), and in the tolerance-inducing activity of recombinant CTLA4-Ig (Grohmann et al., *Nature Immunology* 2002; 3:985-1109). In these three systems, the immunosuppressive effect of IDO can be blocked by the in vivo administration of an IDO inhibitor, such as 1-methyl-tryptophan (also referred to herein as 1-MT or 1 MT).

The transfection of IDO into mouse tumor cell lines confers the ability to suppress T cell responses both in vitro and in vivo (Mellor et al., *J. Immunol.* 2002; 168:3771-3776). In a Lewis Lung carcinoma (LLC) model, administration of 1-MT significantly delayed tumor outgrowth (Friberg et al., *International Journal of Cancer* 2002; 101:151-155). The mouse mastocytoma tumor cell line forms lethal tumors in naive hosts, but is normally rejected by pre-immunized hosts. However, transfection of P815 with IDO prevents its rejection by pre-immunized hosts (Uyttenhove et al., *Nature Medicine* 2003; 9:1269-1274). This effect was entirely dependent on the presence of an intact immune system and was substantially reversed, that is, tumor growth inhibited, by the concomitant administration of 1-MT.

The selective recruitment of IDO$^+$ APCs in the tumor-draining (sentinel) lymph nodes of patients with melanoma (Munn et al., *Science* 2002; 297:1867-1870 and Lee et al., *Laboratory Investigation* 2003; 83:1457-1466) indicates that tumors take advantage of the immunosuppressive effect of IDO by recruiting a population of IDO-expressing host APCs to present tumor antigens. Similar changes have been seen in breast carcinoma and other tumor-associated lymph nodes. In mouse tumor models the IDO-expressing APCs in tumor-draining lymph nodes are phenotypically similar to a subset of dendritic cells recently shown to mediate profound IDO-dependent immunosuppressive in vivo (Mellor et al., *Journal of Immunology* 2003; 171:1652-1655). IDO-expressing APCs in tumor-draining lymph nodes thus constitute a potent tolerogenic mechanism.

The present invention is based on the observation that the administration of an inhibitor of indoleamine-2,3-dioxygenase to a subject suffering from a tumor or infection in combination with administration of an additional therapeutic agent, results in an improved efficacy of therapeutic outcome when compared to the therapeutic outcome observed with the administration of the inhibitor of indoleamine-2,3-dioxygenase alone or the administration of the additional therapeutic agent alone. While not intending to be limited to any single mechanism, the improved efficacy of therapeutic outcome observed may be due to a removal, reversal, or reduction of the immunosuppressive effect of indoleamine-2,3-dioxygenase by the administration an inhibitor of indoleamine-2,3-dioxygenase.

In some embodiments of the present invention, the improved efficacy of therapeutic outcome observed with the administration of an inhibitor of indoleamine-2,3-dioxygenase in combination with an additional therapeutic agent may be demonstrated by determination of the therapeutic synergy. As used herein, a combination manifests "therapeutic synergy" if it is therapeutically superior to one or other of the constituents used at its optimum dose (Corbett et al., *Cancer Treatment Reports*, 66, 1187 (1982). In some embodiments of the present invention, the efficacy of a combination may be characterized by adding the actions of each constituent.

The administration of both an inhibitor of indoleamine-2,3-dioxygenase and at least one additional therapeutic agent can result in an augmentation of the rejection of cells in a subject, wherein the rejection of cells obtained by administering both the inhibitor of indoleamine-2,3-dioxygenase and the additional therapeutic agent is greater than that obtained by administering either the inhibitor of indoleamine-2,3-dioxygenase or the additional therapeutic agent alone. As used herein the augmented rejection of cells includes an increased level of immune system mediated rejection of the cells. As used herein, "cell" can include tumor cells and cells infected with an intracellular pathogen.

Likewise, the administration of both an inhibitor of indoleamine-2,3-dioxygenase and at least one additional therapeutic agent can result in an increased cancer survival rate, a reduced or slowed tumor growth, the reduction in relapse to neoplasm, as in leukemia, a reduction in tumor progression, or a reduction in tumor metastasis, in comparison to that observed with the administration of either the inhibitor of indoleamine-2,3-dioxygenase or the additional therapeutic agent alone. As used herein, "increased cancer survival rate," "reduced tumor growth," "slowed tumor growth," "reduced relapse to neoplasm," "reduced tumor progression," or "reduced tumor metastasis" are as determined by established clinical standards.

The determination of immunosuppression mediated by an antigen presenting cell expressing indoleamine-2,3-dioxygenase (IDO) includes the various methods as described in the examples herein. T cell activation by an antigen-presenting cell and the stimulation of an immune response are as measured by standard methods well known in the immunological arts.

The enzyme indoleamine-2,3-dioxygenase (IDO) is well characterized (see, for example, Taylor et al., *FASEB Journal* 1991; 5:2516-2522; Lee et al., *Laboratory Investigation*, 2003; 83:1457-1466; and Grohmann et al., *Trends in Immunology* 2003; 24:242-248). Compounds that serve as substrates or inhibitors of the IDO enzyme are also well known. For example, Southan et al., (*Med Chem Res.*, 1996; 343-352) utilized an in vitro assay system to identify tryptophan analogues that serve as either substrates or inhibitors of human IDO.

IDO inhibitors of the present invention include, but are not limited to, 1-methyl-tryptophan, β-(3 benzofuranyl)-alanine, β-[3-benzo(b)thienyl]-alanine, 6-nitro-tryptophan, and derivatives thereof. Inhibitors of the IDO enzyme are readily commercially available, for example, from Sigma-Aldrich Chemicals, St. Louis, Mo. An inhibitor of indoleamine-2,3-dioxygenase may be a L isomer of an inhibitor of indoleamine-2,3-dioxygenase, a D isomer of an inhibitor of indoleamine-2,3-dioxygenase, or a racemic mixture of an inhibitor of indoleamine-2,3-dioxygenase. In some embodiments, a preferred IDO inhibitor is 1-methyl-tryptophan, also referred to herein 1 MT.

In accordance with the present invention, an IDO inhibitor is administered to a subject in combination with the administration of one or more previously known treatment modalities. As used herein, the term "additional therapeutic agent" represents one or more agents administered in the previously known treatment modality. An additional therapeutic agent is not an inhibitor of IDO. For example, inhibitors of IDO may be administered to a patient in combination with one or more other modes of cancer treatment. Such additional therapeutic agents include, but are not limited to, chemotherapy, radiation therapy, hormone therapy, surgical resection, treatment with an immunostimulatory cytokine, administration of an anti-tumor vaccine, antibody based therapies, whole body irradiation, bone marrow transplantation, and peripheral blood stem cell transplantation. The chemotherapeutic agents used include, but are not limited to, cyclophosphamide, methotrexate, fluorouracil, doxorubicin, vincristine, ifosfamide, cisplatin, gemcytabine, busulfan (also known as 1,4-butanediol dimethanesulfonate or BU), ara-C (also known as 1-beta-D-arabinofuranosylcytosine or cytarabine), adriamycin, mitomycin, cytoxan, methotrexate, and combinations thereof. The cytokines used include, but are not limited to, IL-Iα, IL-1β, IL-2, IL-3, IL-4, IL-6, IL-8, IL-9, IL-10, IL-12, IL-18, IL-19, IL-20, IFN-α, IFN-β, IFN-γ, tumor necrosis factor (TNF), transforming growth factor-β(TGF-β), granulocyte colony stimulating factor (G-CSF), macrophage colony stimulating factor (M-CSF), granulocyte-macrophage colony stimulating factor (GM-CSF))(U.S. Pat. Nos. 5,478,556, 5,837,231, and 5,861,159), or Flt-3 ligand (Shurin et al., *Cell Immunol.* 1997; 179:174-184).

An IDO inhibitor may also be administered to a patient in combination with other modes of treatment for an infection. Such additional therapeutic agents may include, but are not limited to antiviral agents, antibiotics, antimicrobial agents, cytokines, and vaccines. The cytokines used include, but are not limited to, IL-1α, IL-1β, IL-2, IL-3, IL-4, IL-6, IL-8, IL-9, IL-10, IL-12, IL-18, IL-19, IL-20, IFN-α, IFN-β, IFN-γ, tumor necrosis factor (TNF), transforming growth factor-β (TGF-β), granulocyte colony stimulating factor (G-CSF), macrophage colony stimulating factor (M-CSF), granulocyte-macrophage colony stimulating factor (GM-CSF)(U.S. Pat. Nos. 5,478,556, 5,837,231, and 5,861,159), or Flt-3 ligand (Shurin et al., *Cell Immunol.* 1997; 179:174-184).

An IDO inhibitor may be administered to a patient receiving a vaccine. Such a vaccine may be an anti-viral vaccine, such as, for example, a vaccine against HIV, or a vaccine against tuberculosis or malaria. The vaccine may be a tumor vaccine, including, for example, a melanoma, prostate cancer, colorectal carcinoma, or multiple myeloma vaccine. Dendritic cells (DC) have the ability to stimulate primary T cell antitumor immune responses. Thus, a tumor vaccine may include dendritic cells. Dendritic cell vaccines may be prepared, for example, by pulsing autologous DCs derived from the subject with synthetic antigens, tumor lysates or tumor RNA, or idiotype antibodies, or transfection of DCs with tumor DNA, or by creating tumor cell/DC fusions (Ridgway, *Cancer Invest.* 2003; 21(6):873-86). The vaccine may include one or more immunogenic peptides, for example, immunogenic HIV peptides, immunogenic tumor peptides, or immunogenic human cytomegalovirus peptides (such as those described in U.S. Pat. No. 6,251,399). The vaccine may include genetically modified tumor cells, including genetically modified tumor cells to express granulocyte-macrophage stimulating factor (GM-CSF) (Dranoff, *Immunol Rev.* 2002; 188:147-54).

The administration of the IDO inhibitor may take place before, during, or after the administration of the other mode of therapy.

Inhibitors of IDO may be formulated as a composition. The compositions of the present invention may be formulated in a variety of forms adapted to the chosen route of administration. The formulations may be conveniently presented in unit dosage form and may be prepared by methods well known in the art of pharmacy. Formulations of the present invention include, for example, pharmaceutical compositions including an IDO inhibitor and a pharmaceutically acceptable carrier. The phrase "pharmaceutically-acceptable" refers to molecular entities and compositions that do not produce an allergic or similar untoward reaction when administered to a human. The preparation of such compositions is well understood in the art. The formulations of this invention may include one or more accessory ingredients including diluents, buffers, binders, disintegrants, surface active agents, thickeners, lubricants, preservatives (including antioxidants), and the like.

Formulations of an IDO inhibitor may further include one or more additional therapeutic agents. An additional therapeutic agent may be an antineoplastic chemotherapy agent, including, but not limited to, cyclophosphamide, methotrexate, fluorouracil, doxorubicin, vincristine, ifosfamide, cisplatin, gemcytabine, busulfan (also known as 1,4-butanediol dimethanesulfonate or BU), ara-C (also known as 1-beta-D-arabinofuranosylcytosine or cytarabine), adriamycin, mitomycin, cytoxan, methotrexate, or a combination thereof. Additional therapeutic agents include cytokines, including, but not limited to, macrophage colony stimulating factor, interferon gamma, granulocyte-macrophage stimulating factor (GM-CSF), flt-3, an antibiotic, antimicrobial agents, antiviral agents, including, but not limited to, AZT, ddI or ddC, and combinations thereof.

The tumors to be treated by the present invention include, but are not limited to, melanoma, colon cancer, pancreatic cancer, breast cancer, prostate cancer, lung cancer, leukemia, lymphoma, sarcoma, ovarian cancer, Kaposi's sarcoma, Hodgkin's Disease, Non-Hodgkin's Lymphoma, multiple myeloma, neuroblastoma, rhabdomyosarcoma, primary thrombocytosis, primary macroglobulinemia, small-cell lung tumors, primary brain tumors, stomach cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. As used herein, "tumor" refers to all types of cancers, neoplasms, or malignant tumors found in mammals.

The efficacy of treatment of a tumor may be assessed by any of various parameters well known in the art. This includes, but is not limited to, determinations of a reduction in tumor size, determinations of the inhibition of the growth, spread, invasiveness, vascularization, angiogenesis, and/or metastasis of a tumor, determinations of the inhibition of the growth, spread, invasiveness and/or vascularization of any metastatic lesions, and/or determinations of an increased delayed type hypersensitivity reaction to tumor antigen. The efficacy of treatment may also be assessed by the determination of a delay in relapse or a delay in tumor progression in the subject or by a determination of survival rate of the subject, for example, an increased survival rate at one or five years post treatment. As used herein, a relapse is the return of a tumor or neoplasm after its apparent cessation, for example, such as the return of a leukemia.

Certain pathological conditions, such as parasitic infections, AIDS (caused by the human immunodeficiency virus (HIV) and latent cytomegaloviral (CMV) infections, are extremely difficult to treat since the macrophages act as reservoirs for the infectious agent. Even though the cells are infected with by a foreign pathogen, they are not recognized as foreign. The methods of the present invention may be used to treat such pathological conditions including, but not limited to, viral infections, infection with an intracellular parasite, and infection with an intracellular bacteria. Viral infections treated include, but are not limited to, infections with the human immunodeficiency virus (HIV) or cytomegalovirus (CMV). Intracellular bacterial infections treated include, but are not limited to infections with *Mycobacterium leprae, Mycobacterium tuberculosis, Listeria monocytogenes*, and *Toxplasma gondii*. Intracellular parasitic infections treated include, but are not limited to, *Leishmania donovani, Leishmania tropica, Leishmania major, Leishmania aethiopica, Leishmania mexicana, Plasmodium falciparum, Plasmodium vivax, Plasmodium ovale*, and *Plasmodium malariae*.

The efficacy of treatment of an infection may be assessed by any of various parameters well known in the art. This includes, but is not limited to, a decrease in viral load, an increase in $CD4^+$ T cell count, a decrease in opportunistic infections, eradication of chronic infection, and/or increased survival time.

An inhibitor of IDO may be administered to a subject following bone marrow transplantation or a peripheral blood stem cell transplantation. The efficacy of such an administration may be assessed by any of a variety of parameters well known in the art. This includes, for example, determinations of an increase in the delayed type hypersensitivity reaction to tumor antigen, determinations of a delay in the time to relapse of the post-transplant malignancy, determinations of an increase in relapse free survival time, and/or determinations of an increase in post-transplant survival. The IDO inhibitor may be administered to the subject prior to full hematopoetic reconstitution or prior to recovery from lymphopenia.

The inhibitors of the present invention can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical, or injection into or around the tumor.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intraperitoneal, and intratumoral administration. In this connection, sterile aqueous media that can be employed will be known to those of skill in the art in light of the present disclosure (see for example, "Remington's Pharmaceutical Sciences" 15th Edition). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA.

For enteral administration, the inhibitor will typically be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants. Such implant may be implanted within the tumor.

Therapeutically effective concentrations and amounts may be determined for each application herein empirically by testing the compounds in known in vitro and in vivo systems, such as those described herein; dosages for humans or other animals may then be extrapolated therefrom.

An IDO inhibitor may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

The present invention is illustrated by the following examples. It is to be understood that the particular examples, materials, amounts, and procedures are to be interpreted broadly in accordance with the scope and spirit of the invention as set forth herein.

EXAMPLES

Example 1

Potential Regulatory Function of Human Dendritic Cells Expressing Indoleamine 2,3-Dioxygenase This example describes a subset of human APCs that express indoleamine 2,3-dioxygenase (IDO) and inhibit T cell proliferation in vitro. IDO-positive APCs constituted a discrete subset identified by coexpression of the cell-surface markers CD123 and CCR6. In the dendritic cell (DC) lineage, IDO-mediated suppressor activity was present in fully mature as well as immature $CD123^+$ DCs. $IDO^+$ DCs could also be readily detected in vivo, indicating that these cells represent a regulatory subset of APCs in humans.

Using an IDO-specific antibody (FIG. 3), it was shown by flow cytometry that fresh human monocytes expressed low to undetectable levels of the IDO protein (FIG. 1A). Monocyte-derived macrophages (Mφs) up-regulated IDO upon activation with interferon-γ (IFN-γ)(Munn et al., *J. Exp. Med.*, 1999; 189:1363). Expression of IDO in these cells was confined to a particular subset of cells coexpressing CD123 (the interleukin-3 (IL-3) receptor α chain] and the chemokine receptor CCR6 (FIG. 1A). Similarly, monocyte-derived DCs (Sallusto and Lanzavecchia, *J. Exp. Med.*, 1994; 179:1109) expressed IDO, which was also confined to a $CD123^+$, $CCR6^+$ subset.

Figure 1B:
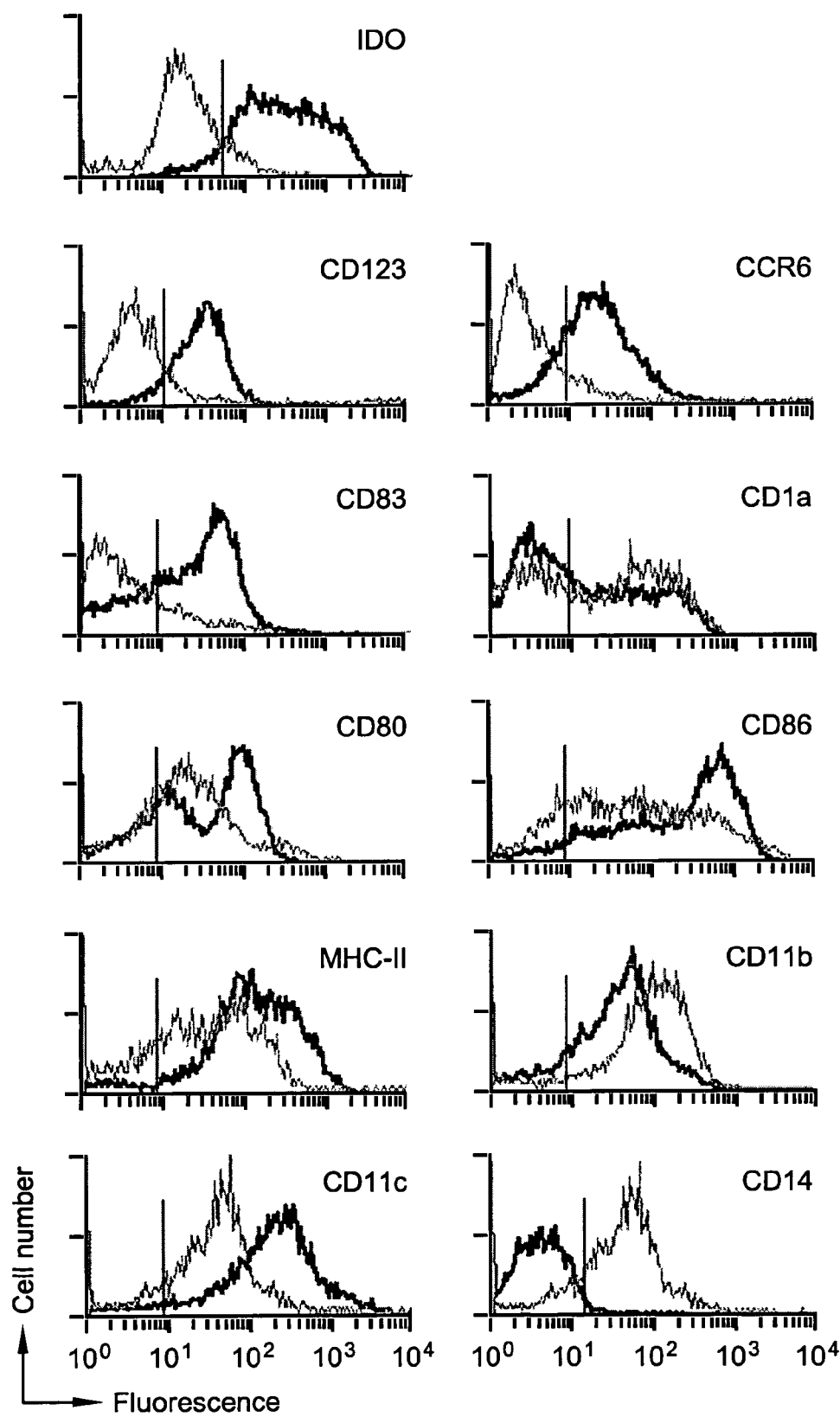
Figure 1C:
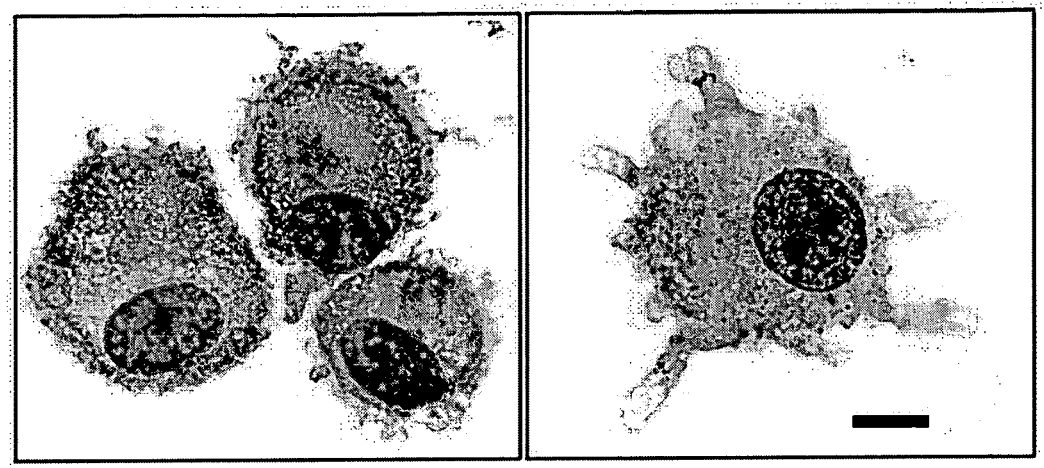
Figure 1D:
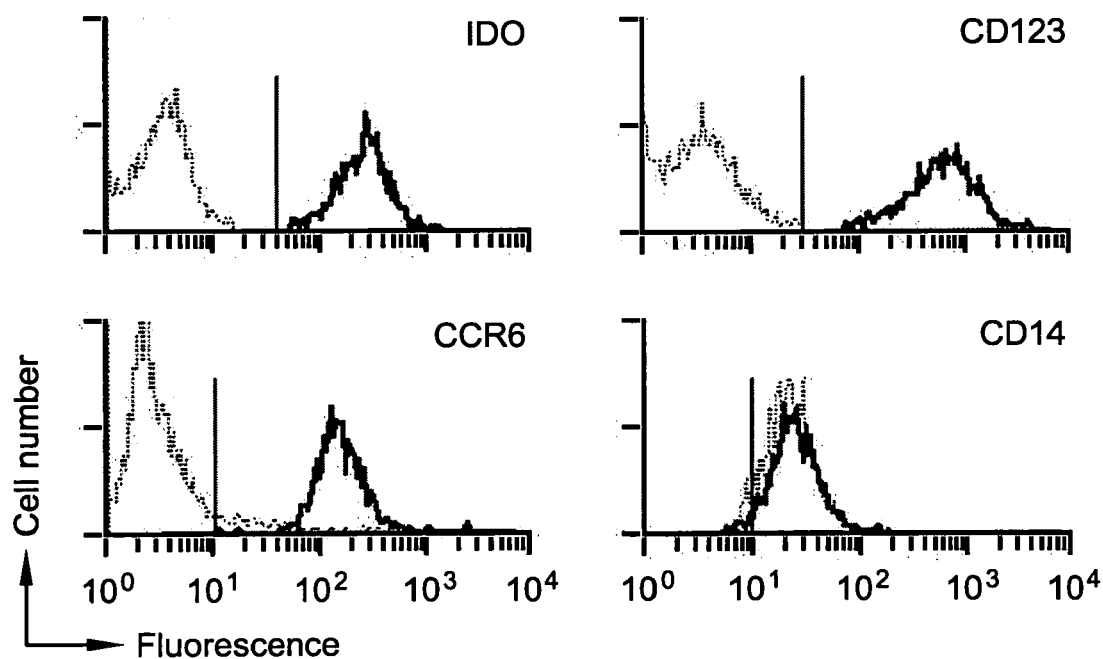

Because serum factors are known to influence DC maturation (Romani et al., *J. Immunol. Methods*, 1996; 196:137), DCs were derived in both bovine calf serum (BCS)-based medium and serum-free medium (SFM). Both systems yielded $IDO^+$ DCs with the same phenotype, but greater than 90% of the $IDO^{NEG}$ cells in SFM were tightly adherent. This allowed facile enrichment of the nonadherent $IDO^+$ population to greater than 90% purity. The $IDO^+$ cells expressed cell-surface markers $CD14^{NEG}$, $CD83^+$, $CD80^+$, $CD86^{HI}$, and $HLA-DR^{HI}$ (FIG. 1B), morphology consistent with mature DCs (FIG. 1C). Adherent cells lacked CD83 and displayed residual levels of CD14, consistent with an immature or transitional phenotype. Although $IDO^+$ cells in DC cultures expressed DC-specific lineage markers, and the $IDO^+$ Mφs expressed Mφ-lineage markers (FIG. 1D), in both types of cells the $IDO^+$ subset could be specifically identified by expression of CD123 and CCR6.

Figure 2E:
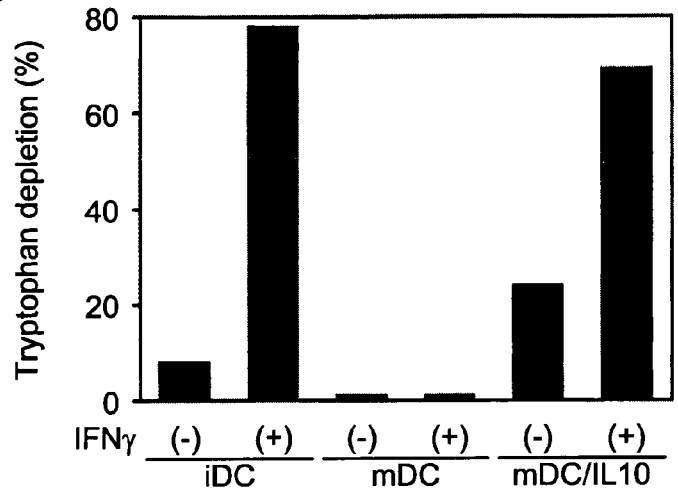

As shown previously (Munn et al., *J. Exp. Med.*, 1999; 189:1363), resting macrophage colony-stimulating factor (MCSF)-derived Mφs did not express high concentrations of IDO until they received a triggering signal such as IFN-γ (FIG. 2A). In contrast, IDO could be detected constitutively in $CD123^+$ DCs (FIG. 2B). However, activation with IFN-γ was still required for expression of functional enzymatic activity FIG. 2E), which suggests that the IDO protein could exist in both enzymatically active and inactive states. Post-translational regulation of enzymatic activity (constitutive expression of enzyme protein but with additional signals being required for functional activity) is a feature of many regulatory enzymes. Expression of IDO protein without enzymatic activity has been described in murine DCs (Fallarino et al., *Int Immunol.*, 2002; 14:65). However, the mechanism by which IDO might exist in distinct functional states remains to be determined. Because the maturational status of DCs may affect a number of functional attributes of these cells, it was determined whether maturation affected IDO expression by $CD123^+$ DCs. Although maturation itself had no effect on the constitutive (basal) expression of IDO protein, subsequent activation of mature DCs with IFN-γ resulted in complete down-regulation of IDO. This was a consistent observation in 16 experiments with 10 different donors and was confirmed by flow cytometry (FIG. 2C), enzymatic activity (FIG. 2E), and mRNA.

Interleukin 10 (IL-10) is a regulatory cytokine that has been associated with the development of tolerogenic DCs (Steinbrink et al., *J. Immunol.*, 1997; 159:4772). The presence of IL-10 during maturation prevented IFN-γ-induced down-regulation of IDO, resulting in sustained expression of functional IDO even in mature, IFN-γ-activated DCs (FIGS. 2D and 2E). Similar results were observed when transforming growth factor-β was present during maturation. Taken together, these data raised the possibility that expression of IDO by mature DCs might be determined by the prevailing regulatory influences during maturation.

Figure 2F:
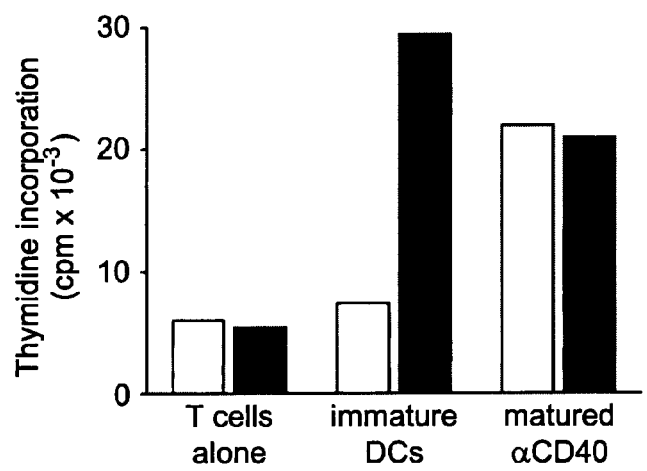
Figure 2G:
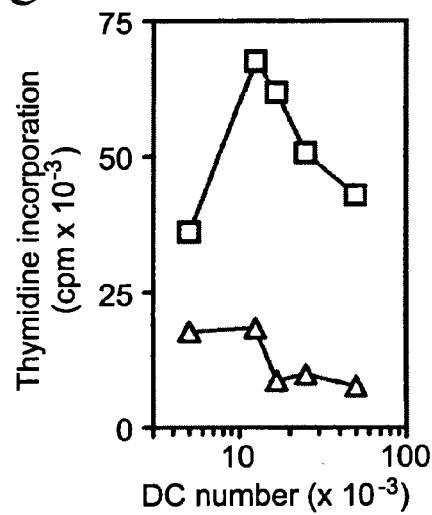

DCs were next tested for their ability to stimulate T cells in allogeneic mixed-leukocyte reactions (MLRs). In FIGS. 2B-2E, recombinant IFN-γ was added to simulate signals from activating T cells (Munn et al., *J. Exp. Med*, 1999 189: 1363), but for MLRs the DCs received no exogenous IFN-γ. Immature DCs, selected and enriched to >90% purity for IDO expression (FIG. 1B), stimulated very little T cell proliferation (FIG. 2F). However, in most donors proliferation could be significantly enhanced by addition of 1-methyl-D-tryptophan (1 MT), a competitive inhibitor of IDO. After maturation, enriched $IDO^+$ DCs displayed one of two patterns: in 4 of 45 experiments the mature DCs lost their IDO-mediated inhibitory activity (FIG. 2F), whereas in 41 of 45 experiments they maintained potent inhibitory activity despite maturation, which was reversed by the addition of 1 MT (FIG. 2G). Continued expression of IDO by mature DCs in the latter experiments was confirmed by flow cytometry on MLR cultures and by measurement of tryptophan and kynurenine in supernatants. The two different patterns observed in MLR were suggestive of the different patterns observed when mature DCs were tested in isolation (FIGS. 2C and 2D).

Figure 2H:
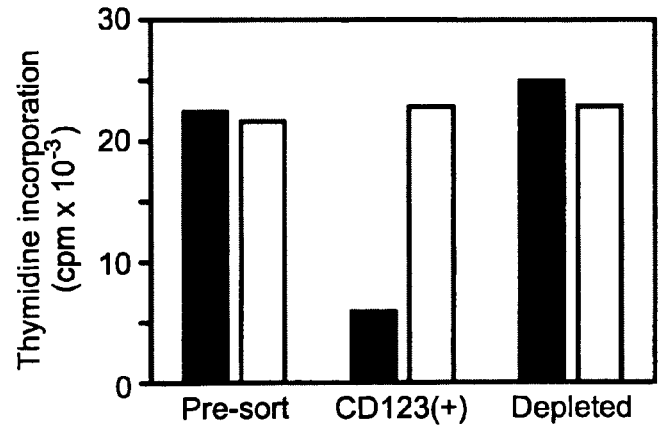
Figure 2I:
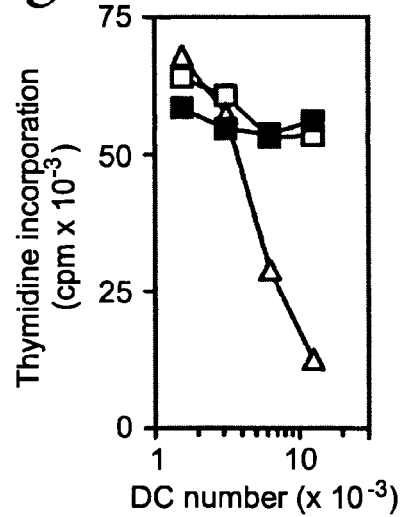

The experiments in FIG. 2G were performed with highly enriched $IDO^+$ DCs from SFM cultures. In contrast, BCS medium yielded a mixture of nonadherent $IDO^+$ and $IDO^{NEG}$ cells, with $IDO^{NEG}$ cells typically in the majority. Under these conditions, T cell activation predominated, and 1 MT had little detectable effect (FIG. 2H). However, when the $IDO^+$ DCs were enriched from such mixtures by sorting for CD123 expression, they displayed inhibitory activity comparable to the $IDO^+$ DCs from SFM (FIG. 2H). To verify the specificity of 1 MT as an inhibitor of IDO, 1 MT was added to MLRs containing APCs that did not express inhibitory amounts of IDO (adherent cells from SFM cultures, less than 10% IDO). Under these conditions, T cell proliferation was not inhibited, and 1 MT had no effect on T cell proliferation (FIG. 2I).

The staining of tissue from fifteen non-inflamed tonsils removed in routine tonsillectomy showed scattered IDO+ cells in germinal center and T cell regions, indicating that in vivo, few $IDO^+$ cells are detected in normal lymphoid tissue. However, human tonsils displaying features of chronic inflammation often possessed intense focal infiltrates of $IDO^+$ cells, which were morphologically distinct from $Ham56^+$ macrophages (Orenstein and Wahl, *Ultrastruct. Pathol.*, 1999; 23:79) or $S100^+$ interdigitating DCs (Cochran et al., *Mod. Pathol.*, 2001; 14:604). Some $IDO^+$ cells coexpressed CD83, a marker of mature DCs, and some expressed CD123 and CCR6 (FIG. 3B). However, not all $CD83^+$ (or $CD123^+$ or $CCR6^+$) cells expressed IDO, and no single marker identified all $IDO^+$ cells, which suggests that IDO may be expressed by more than one population in vivo. Analyses of regional and sentinel (first draining) lymph nodes taken from patients with malignant melanoma revealed that 25 of 66 patients had one or more nodes with abnormal accumulation of $IDO^+$ cells.

For these studies, lymph nodes were analyzed from 26 patients with malignant melanoma at the Medical College of Georgia; 13 of 26 patients were found to have at least one node (often more than one) with markedly abnormal accumulation of $IDO^+$ cells (3+ or 4+ on a 4+ scale, independently graded by 3 pathologists). The $IDO^+$ cells were morphologically monocytic or plasmacytoid in appearance, and were found infiltrating extensively throughout the lymphoid regions, typically concentrating in the interfollicular and T cell zones. Accumulations were observed around blood vessels, at the margins of medullary sinuses, and the interface between lymphoid tissue and tumor metastases. Recruitment of $IDO^+$ dendritic cells to specific regional lymph nodes was also seen in smaller series of patients with carcinoma of the breast, lung, colon and pancreas (comprising all of the other histologies examined).

In a separate study, sentinel lymph nodes were obtained from patients with malignant melanoma. Each node was documented to be the initial tumor-draining lymph node by in vivo lymphoscintigraphy, and all were negative for metastatic tumor by conventional pathologic studies. Twelve of these 40 sentinel nodes were found to have abnormal accumulation of $IDO^+$ cells (grades 1+ to 4+). In many of these patients, accumulation of $IDO^+$ cells in the sentinel node occurred before overt metastasis. Similar accumulation of $IDO^+$ cells was found in nodes from patients with breast, colon, lung, and pancreatic cancers.

In this example, a subset of human monocyte-derived DCs that use IDO to inhibit T cell proliferation in vitro is described. In both DC and M lineages, $IDO^+$ cells could be characterized by coexpression of CD123 and CCR6 (despite the expression of otherwise distinct lineage-specific markers), which suggests that the $IDO^+$ population may represent a discrete subset of professional APCs. $IDO^+$ DCs expressed major histocompatibility complex class II and costimulatory molecules and were effective stimulators of T cell proliferation when IDO was blocked by 1 MT, which suggests that these cells could act as competent APCs. This may reflect a regulatory subset of APCs specialized to cause antigen-specific depletion (Munn et al., *J. Immunol.* 1996; 156:523) or otherwise negatively regulate the responding population of T cells. In light of the finding that large numbers of such cells are present in a proportion of tumor-draining lymph nodes, it appears that IDO$^+$ APCs may participate in the state of apparent immunologic unresponsiveness displayed by many cancer patients toward tumor-associated antigens. However, the extent to which IDO-expressing APCs might influence immunologic unresponsiveness in vivo remains to be determined.

Polyclonal Antibody Preparation and Validation

The peptide LIESGQLRERVEKLNMLC (SEQ ID NO:1) was prepared based on the GenBank sequence of human IDO (GenBank Accession Number M34455; Dai and Gupta, *Biochem. Biophys. Res. Commun.*, 1990; 168:1-8) and conjugated to keyhole limpet cyanogen. Rabbits were immunized with conjugated peptide in complete Freund's adjuvant and boosted three times in incomplete Freund's adjuvant (all antibody preparation and affinity purification steps were performed by QCB/BioSource International). This peptide gave the best results out of several sequences screened for their ability to detect IDO in formalin-fixed paraffin-embedded tissue and flow cytometry. Using THP1 monocytic leukemia cell lysates, the antibody detected a single band of the expected 45 kD molecular mass (Dai and Gupta, *Biochem. Biophys. Res. Commun.*, 1990; 168:1-8) by western blot (FIG. 3A). Immunoreactivity in western blot was blocked by pre-adsorption of the antibody with an excess of the immunizing peptide (FIG. 3A). The 45 kD band was inducible by IFNγ in human monocyte-derived Mφs (FIG. 3B), consistent with previous western blot studies by others (Thomas et al., *J. Immunol.*, 2001; 166:6332; and Grant et al., *J. Virol.*, 2000; 74:4110). Immunoprecipitation of THP1 cell lysates yielded a single 45 kD protein band on silver stain, which was not precipitated in the presence of the immunizing peptide (FIG. 3C). The antibody detected an IFNγ-inducible antigen by flow cytometry in monocyte-derived macrophages, and this signal was reduced by greater than 95% by pre-adsorption of the antibody with the immunizing peptide (FIG. 3D). By immunohistochemistry on formalin-fixed, paraffin-embedded specimens of human placenta, the antibody detected an antigen specifically localized to syncytiotrophoblast (FIG. 3E). Syncytiotrophoblast was used for validation because it is an unambiguous cell type that has been previously shown to express IDO by immunohistochemistry (Kamimura et al., *Acta. Med Okayama*, 1991; 45:135), which has been independently confirmed using enzymatic-activity assays on highly purified placental cell fractions (Kudo and Boyd, *Biochem. Biophys. Acta*, 2000; 1500:119). Reactivity in immunohistochemistry was fully blocked by pre-adsorption of the antibody with the immunizing peptide (FIG. 3E).

Distinction of IDO$^+$ Cells from CD123$^+$ Plasmacytoid DCs

CD123 is also found on "plasmacytoid" DCs or pre-DC2 cells. However, the CD123 expression observed on the IDO$^+$ subset of monocyte-derived DCs was at the lower level described on myeloid DCs (Cella et al., *Nat. Med.*, 1999; 5:919), not the 10- to 100-fold higher levels that we observed on plasmacytoid DCs. The IDO$^+$ cells also expressed myeloid markers (CD11b, CD11c) and did not express the pre-DC2 marker BDCA2 (Dzionek et al., *J. Immunol.*, 2000; 165: 6037). Plasmacytoid dendritic cells (CD123$^+$ CD11c$^{NEG}$ cells) showed no detectable expression of IDO (fresh or following activation with IFNγ). The CD123$^+$ IDO$^+$ subset of monocyte-derived DCs and Mφs co-expressed CCR6. While CD123 was expressed constitutively, CCR6 was inducible, and was expressed under the same conditions in which IDO protein was induced. Thus, in MCSF-derived Mφs CCR6 required induction by IFNγ, whereas in DCs CCR6 was constitutively expressed on CD123$^+$ DCs.

Monocyte Isolation and Culture

Human monocytes (typically greater than 95% purity) were isolated by leukocytapheresis and counterflow elutriation as described (Munn et al., *J. Exp. Med.*, 1999; 189:1363), then cryopreserved in replicate aliquots. Monocyte-derived Mφs were cultured in RPMI-1640 medium supplemented with 10% bovine calf serum (Hyclone)("BCS system") and received MCSF (200 units/ml, gift of Genetics Institute) on day 0 (Munn et al., *J. Exp. Med.*, 1999; 189:1363). Monocyte-derived DCs were cultured in 100 mm petri dishes in either BCS medium (Sallusto and Lanzavecchia, *J. Exp. Med.*, 1994; 179:1109) or in serum-free medium X-vivo 15, Bio-Whitaker, "SFM system")(Chen et al., *Blood*, 1998; 91:4652). SFM yielded a somewhat higher proportion of IDO$^+$ cells, but the phenotype and function of the cells was identical. DCs received GMCSF (50 ng/ml, R&D Systems)+ IL4 (50 ng/ml, R&D Systems) on days 0, 2 and 4. For experiments where CCR6 expression was of interest, cultures received a single dose of GMCSF+IL4 (100 ng/ml each) on day 0, which gave higher expression of CCR6 (Yang et al., *J. immunol.*, 1999; 163:1737). Non-adherent DCs were harvested by aspiration; adherent cells and MCSF-derived macrophages were harvested with 5 mM EDTA. For maturation studies, cells were treated for the final 48 hours with one of the following: 0.5 ug/ml activating anti-CD40 antibody (Mabtech); a cytokine cocktail comprising TNFα (1100 units/ml, Pharmingen), IL1β (1870 units/ml, Pharmingen), IL6 (1000 units/ml, Pharmingen) and PGE2 (1 ug/ml, Sigma) (Jonuleit et al., *Eur. J. Immunol.*, 1997; 27:3135)(12); or 50% v/v conditioned medium (X-vivo 15) from activated monocytes (allowed to adhere overnight to petri dishes coated with immobilized IgG (Cappel ICN)(Reddy et al. *Blood*, 1997; 90:3640). In some experiments, DCs also received IL10 (R&D Systems, 100 ng/ml) with the maturation stimuli. For activation studies, cells received 100 units/ml IFNγ (Genentech) during the final 18 hours of culture.

Flow Cytometry

All antibodies and reagents were from BD-Pharmingen unless specified. Fresh whole blood was stained using BD FACS Lysing Solution. For cultured cells, nonadherent cells were pooled with adherent cells (harvested with 5 mM EDTA in PBS for 10 minutes) prior to analysis, unless otherwise specified. Cells were triple-stained with anti-CD123-biotin (clone 7G3) followed by streptavidin-perCP, plus anti-CD11c-allophycocyanin (clone S-HCL-3) or anti-CCR6-fluorescein (clone 53103.111, R&D systems). CCR6 results were confirmed using a second antibody (11A9, BD-Pharmingen). After fixation and permeablization (Cytofix/Cytoperm), cells were stained with rabbit anti-IDO antibody followed by PE-labeled anti-rabbit secondary antibody (Jackson Immunoreasearch, cross-adsorbed against mouse, human and bovine IgG). For all experiments, the negative control for IDO staining was the anti-IDO antibody pre-adsorbed with a 50-fold molar excess of the immunizing peptide. Dendritic cells and Mφs were gated on forward and side scatter to exclude contaminating lymphocytes and debris. For phenotyping experiments, cells were stained without permeablization, using a multicolor panel of CD123 versus various markers (all from BD-Pharmingen).

Mixed-leukocyte Reactions

Dendritic cells were mixed with 5×10⁵ allogeneic lymphocytes (80-85% T cells, balance B cells and NK cells, less than 1% monocytes) in 250 ul of MLR culture medium (10% fetal calf serum in RPMI-1640). Replicate wells received 1-methyl-tryptophan (Aldrich) at a final concentration of 200 uM at the time of T cell addition, or buffer control. Unless otherwise specified, the D-isomer of 1 MT was used. After five days, proliferation was measured by four hour thymidine incorporation assay. "V"-bottom culture wells (Nunc) were used in MLR assays to maximize cell-cell contact. It was found that this geometry gave significantly greater sensitivity for measuring suppression, as compared to flat-bottom wells. However, V-bottom wells were not a prerequisite for detecting suppression (e.g., all of the experiments in both Munn et al., *J. Exp. Med.,* 1999; 189:1363; and Mellor et al., *J. Immunol.,* 2002; 168:3771 used flat-bottom wells). The V-bottom geometry itself was not suppressive, as shown by the brisk T cell proliferation observed when IDO was inhibited by 1 MT (FIG. 2G), or when IDO$^{NEG}$ APCs were used as stimulators (FIG. 2I). Tryptophan depletion in these cultures is shown in FIG. 4. The data represented in FIG. 4 indicate that inhibition of proliferation did not depend on artificially high concentrations of APCs or global depletion of tryptophan from the entire culture medium. However, these experiments were still consistent with a localized depletion of tryptophan (i.e., occurring within the immediate zone of contact between DCs and T cells), since addition of supra-physiologic levels of tryptophan to the culture medium (250 uM) completely reversed the DC-mediated inhibition of T cell proliferation, as has been previously described (Munn et al., *J. Exp. Med.,* 1999; 189:1363).

Immunohistochemistry

For paraffin blocks, sections were deparaffinized, treated for 8 minutes with proteinase K (Dako), and stained with rabbit anti-human IDO antibody (5 ug/ml in phosphate-buffered saline with 0.05% Tween-20 and 10% goat serum). Detection was via secondary antibody conjugated to alkaline phosphatase (LSAB2-rabbit kit, Dako) with Fast Red or nitro-blue tetrazolium chromogen. In all experiments, negative controls consisted of the anti-IDO antibody neutralized with a molar excess of the immunizing peptide. For two-color immunofluorescent staining, frozen sections of human tonsil were fixed for 10 minutes in 10% formalin, then primary antibodies were applied against IDO (0.05 ug/ml) and either CD83 (Immunotech), CD123 (Santa Cruz) or CCR6 (R&D Systems). IDO was detected with rabbit-specific secondary antibody conjugated to Alexa-488 (Molecular Probes); mouse antibodies were detected with species-specific secondary antibody conjugated to Alexa-568 (all secondary antibodies were cross-adsorbed for multiple labeling). Some CD4⁺ T cells showed low-level staining for IDO, consistent with previous reports (Currell et al., *J. Interferon Cylokine Res.,* 2001; 21:431). This T cell staining was minimal by the less-sensitive immunohistochemistry technique, and with immunofluorescence could be unambiguously distinguished from the high-level IDO expression seen in APCs through the use of two-color staining.

Use of Recombinant IFNγ

When DCs or Mφs were tested in isolation (i.e., without T cells, as in FIGS. 2A-2E) recombinant human IFNγ was added during the final 18 hours of culture), in order to simulate the activating signals that would normally be delivered by activating T cells to APCs during antigen-presentation (Munn et al., *J. Exp. Med.,* 1999; 189:1363). This allowed the identification of 3 stages at which IDO expression could be regulated in DCs; differentiation, maturation, and the final activation step (e.g., by IFNγ). Simulating this final step proved critical in elucidating the differential regulation of IDO in mature versus immature DCs (see FIGS. 2B-2D). In this system, IFNγ was found to be capable of both up-regulating and down-regulating IDO, depending the maturation status of the DCs. This dual role for IFNγ is consistent with the literature, which has shown roles for IFNγ both as a pro-inflammatory cytokine, and as a participant in tolerance and negative regulation (Konieczny et al., *J. Immunol.,* 1998; 160: 2059). When DCs were to be used in MLRs they were not exposed to IFNγ during culture, nor was recombinant IFNγ added to the MLRs. Thus, any activating signals influencing expression of IDO in MLRs would be derived physiologically, from the T cells themselves.

Two Patterns of IDO Expression in Mature DCs

FIG. 2C and FIG. 2D tested mature DCs in isolation, using IFNγ to simulate signals from T cells. While the cytokine milieu in actual MLRs is more complex than this simplified system, the pattern observed in FIG. 2F (loss of inhibitory activity for T cells when DCs were matured) was consistent with the pattern shown in FIG. 2C (down-regulation of IDO when mature DCs were activated with IFNγ). In contrast, the pattern shown in FIG. 2G (maintenance of inhibitory activity in MLR despite maturation) was consistent with FIG. 2D (expression of functional IDO in mature DCs). It is currently unknown what factors in the MLRs favored maintenance of IDO-mediated suppression in the large majority of experiments. One potentially significant variable could be the production of regulatory cytokines such as IL10 by the activated T cells. This issue will require further investigation to elucidate. However, the key observation arising from FIGS. 2D and 2G is that the CD123⁺ subset of DCs has the potential for IDO-meditated inhibition of T cells even when mature.

Donor-to-donor Variability

Inhibition of T cell proliferation by immature DCs was seen in 10/10 experiments using seven different donors. In seven of these ten experiments, T cell proliferation was significantly enhanced by 1 MT. With mature DCs, inhibition of T cell proliferation was observed in 12/13 experiments (six different donors) using sorted CD123⁺ DCs (BCS system) as shown in FIG. 2H. Also with mature DCs, inhibition was observed in 28/32 experiments (nine different donors) using non-adherent IDO-enriched cells (SFM system) as shown in FIG. 2G. In four experiments using mature DCs (four donors), the DCs showed loss of inhibition upon maturation, the pattern shown in FIG. 2F. However, when two of these four donors were tested in multiple experiments it was found that by using different conditions (different maturation regimen, different responder T cells), these donors could be induced to show inhibition after maturation. Thus, the majority of donors showed IDO-mediated inhibition by mature DCs, and this was subject to influence by the conditions prevailing during maturation and MLR.

Use and Limitations of 1 MT

In all experiments, the D-isomer of 1 MT was used unless otherwise specified, because it gave better reversal of suppression with less toxicity than the DL-racemic mixture used previously (Munn et al., *Science,* 1998; 281:1191). As previously published (Munn et al., *J. Exp. Med.,* 1999; 189:1363), 1 MT is not an efficient inhibitor of IDO (Km of approximately 30 uM). When the number of IDO⁺ DCs is large, a racemic mixture of 1 MT is only partially effective in reversing IDO-mediated inhibition of T cell proliferation. While this could in theory imply a second, unrelated mechanism of suppression that happened to co-segregate with IDO in our system, it more likely reflects the less-than-perfect efficiency of a racemic mixture of 1 MT as an inhibitor of IDO. The effectiveness of 1 MT was significantly enhanced if the DCs were matured (e.g., FIG. 2G), which may reflect a reduced potency of the IDO system in mature DCs (as suggested by FIG. 2C), and the greater inherent stimulatory capacity of mature DCs.

Expression of IDO Protein without Constitutive Activity

FIGS. 2B-2E suggest that IDO may exist in both enzymatically-active and inactive forms. This type of regulation, in which the functional enzymatic activity of a pre-formed pool of protein is turned on and off by post-translational events, is familiar in other enzyme systems. Examples include regulation of protein kinases by phosphorylation in kinase cascades, regulation of signal-transduction proteins by farnesylation, and others. The shift between active and inactive states is required for the proper biologic function of these enzymes. It is not yet known whether there exist post-translational modifications that regulate IDO activity. However, it is known that factors which affect the heme prosthetic group of IDO can markedly alter enzymatic activity (Thomas et al., *J. Biol. Chem.*, 1994; 269:14457; Thomas et al., *J. Immunol.*, 2001; 166:6332) without necessarily affecting protein levels (Thomas et al., *J. Immunol.*, 2001; 166:6332), so the possibility that IDO could exist in both active and inactive forms is not without precedent. Consistent with this, expression of immunoreactive IDO protein without functional enzymatic activity has recently been described in subsets of murine DCs (Fallarino et al., *Int. Immunol.*, 2002; 14:65). FIG. 3D shows data consistent with the possibility that activation of Mφs with IFNγ may induce post-translational modifications of IDO. This is suggested by the emergence of two additional protein species on 2D-gel electrophoresis after activation with IFNγ. These species react with the anti-IDO antibody on western blot (FIG. 3D) and migrate similarly to the major species in the SDS-PAGE dimension, but display shifted isoelectric points. Such shifts in pI may be caused by alternate splicing, or, more commonly, may reflect post-translational modifications such as phosphorylation or acylation.

Thus, it appears that a constitutive presence in immature DCs of immunoreactive IDO protein, but with functional enzymatic activity being induced only after IFNγ activation, reflects an additional layer of specific, biologically relevant regulation of IDO. In this regard, it should also be noted that, while flow cytometry failed to detect significant IDO in resting MCSF-derived Mφs (FIG. 2A), the more sensitive western blot analysis of detergent-solublized whole-cell lysates reveals a pool of constitutive IDO protein even in resting Mφs (FIGS. 3B and 3D), just as in immature DCs.

Example 2

A Small Population of Dendritic Cells in Tumor-Draining Lymph Nodes Mediates Dominant Immunosuppression via Indoleamine 2,3-dioxygenase The specific role of tolerogenic dendritic cells (DCs) in tumor immunology remains unclear. In part, this is because the specific molecular mechanisms by which DCs create tolerance are still poorly understood (Moser, *Immunity*, 2003; 19:5). The present example focuses on the immunoregulatory enzyme indoleamine 2,3-dioxygenase (IDO)(Taylor et al., *FASEB J.*, 1991; 5:2516). IDO is a tryptophan-degrading enzyme; its expression by cultured macrophages and DC allows them to inhibit T cell proliferation in vitro (Munn et al., *J. Exp. Med.*, 1999; 189:1363; Hwu et al., *J. Immunol.*, 2000; 164:3596; and Munn et al., *Science*, 2002; 297:1867). Transfection of recombinant IDO into tumor cell lines confers the ability to inhibit antigen-specific T cell responses in vitro (Mellor et al., *J. Immunol.*, 2002; 168:3771), and protects immunogenic tumor from rejection in vivo (Uyttenhove et al., *Nat. Med.*, 2003; 9:1269). Endogenous IDO has been implicated in maternal tolerance toward the allogeneic fetus (Munn et al., *Science*, 1998; 281:1191), tolerance to self antigens in NOD mice (Grohmann et al., *J. Exp. Med.*, 2003; 198:153), and as a downstream effector mechanism for the tolerance-inducing agent CTLA4-Ig (Grohmann et al., *Nat. Immunol.*, 2002; 3:985). Thus, IDO represents a potent endogenous immunoregulatory system that may be exploited by some tumors as a mechanism of immune evasion.

IDO can be expressed by a variety of human tumors and tumor cell lines (Uyttenhove et al., *Nat. Med.*, 2003; 9:1269; Logan et al., *Immunol.*, 2002; 105:478; and Friberg et al., *Int. J. Cancer*, 2002; 101:151). This observation, combined with evidence from IDO-transfected tumors (Uyttenhove et al., *Nat. Med.*, 2003; 9:1269), suggests that expression of IDO by malignant cells may contribute to local immunosuppression within tumors. As shown in Example 1, IDO is expressed by a population of host cells found in certain tumor-draining lymph nodes (TDLNs), indicating that these cells represent a population of immunosuppressive host DCs that are recruited by the tumor. In the present example, a murine tumor model was developed to isolate and characterize the IDO-expressing DCs from TDLNs was developed and used to study IDO-dependent T cell suppression.

The present example demonstrates that tumor-draining lymph nodes in mice contain a population of plasmacytoid dendritic cells (pDCs) that constitutively express immunosuppressive levels of the enzyme indoleamine 2,3-dioxygenase (IDO). These cells expressed multiple markers of mature pDCs, but also co-expressed CD19 and pax5, suggesting derivation from a lymphoid B-cell progenitor. $CD19^+$ pDCs comprised less than 0.5% of cells in tumor-draining lymph nodes (TDLN) but could potently and dominantly suppress $CD8^+$ T cell responses in vitro, in an IDO-dependent fashion. Adoptive transfer of DCs from tumor-draining lymph nodes created T cell unresponsiveness and dominant immunosuppression to a strong nominal antigen in naive, non-tumor-bearing hosts. These effects were abrogated by targeted disruption of the IDO gene in the transferred DCs, or by administration of the IDO inhibitor drug 1-methyl-tryptophan following adoptive transfer. These results indicate that IDO-expressing DCs create a local microenvironment in tumor-draining lymph nodes that suppresses host anti-tumor cytotoxic T cell responses.

Materials and Methods

Clinical studies. A series of samples from patients with malignant melanoma were randomly selected, based on the following inclusion criteria: radiographically mapped sentinel LN at the time of diagnosis; no metastases at presentation; and no further therapy given following initial surgical resection. Sentinel LN biopsies were stained for IDO by immunohistochemistry, expression was graded by three pathologists as described (Lee et al., *Lab. Invest.*, 2003; 83:1457), and a consensus score obtained. Patients were stratified into normal (grade 0) versus abnormal (grade 1+ or higher) expression, and compared by Kaplan-Meier survival analysis. Sentinel LN biopsies from patients with breast cancer were selected from the archives of the Medical College of Georgia. Studies with human subjects were approved by the appropriate Institutional Review Board.

Mouse tumor models. C57BL/6 mice (Jackson, Bar Harbor, Me.) were implanted with tumors in the anteriomedial thigh, using either $4\times10^4$ B16F 10 (ATCC, Bethesda, Md.) or $1\times10^6$ B78H1•GM-CSF. B78H1•GM-CSF cells recruit large numbers of APCs (Dranoff et al., Proc. Natl. Acad. Sci. USA, 1993; 90:3539) and were originally designed as a vaccine strategy. GMCSF-transfected tumors are immunogenic if lethally irradiated prior to injection (Borrello et al., Hum. Gene Ther., 1999; 10:1983), but live tumors grow progressively and create systemic tolerance to tumor antigens (Bronte et al., J. Immunol., 1999; 162:5728). Thus, B78H1•GM-CSF represented an excellent model for our studies, since it recruited many DCs but nevertheless provoke a protective immune response. Tumors were 10-12 days after implantation, well prior to the stage of large, metastatic tumors (day 21) in which the hosts began to show alteration in spleen and non-tumor-draining LNs. FACS analysis showed that the pDCs recruited by B78H1•GM-CSF tumors were phenotypically identical to those recruited by B16F10 tumors, but with the advantage that they could be recovered in quantities sufficient for functional analysis. Immunohistochemical studies of established B16F10 and B78H1•-GM-CSF tumors showed that neither expressed IDO in the tumor cells themselves. Studies, presented herein, using IDO-deficient hosts formally showed that the relevant IDO expression was in host-derived APCs, not the tumor cell lines themselves.

Immunohistochemistry. Immunohistochemistry was performed on human materials as described in Example 1, following proteinase K antigen retrieval of formalin-fixed, paraffin-embedded sections. Mouse tissues were fixed overnight in 10% formalin and paraffin embedded. Since the IDO epitope was not stable to prolonged storage in thin sections, staining was performed within 24 hours of sectioning. Staining was performed using a rabbit anti-mouse IDO polyclonal antibody (Mellor et al., J. Immunol., 2003; 1171:1652). Cytocentrifuge preparations were made from cell suspensions following fluorescence-activated cell sorting, fixed for 10 minutes in 10% formal in, and stained within 24 hours. Controls for human and mouse staining included the anti-IDO antibody neutralized with a molar excess of the immunizing peptide.

Flow cytometry and cell sorting. Single-cell suspensions of LNs were obtained by teasing and disaggregation through a 40 micron mesh. Spleen cells were obtained by ground-glass homogenization and hypotonic lysis of erythrocytes. Cells were stained by 4-color immunofluorescence, using CD11c versus B220 versus CD19 versus a panel of other markers. Fc binding was blocked using a commercial anti-CD 16/CD32 cocktail (BD Pharmingen, San Diego, Calif.). All acquisitions and sorts were performed using pulse-processing doublet discrimination. Antibodies against the following antigens were from BD-Pharmingen: CD11c (clone HL3), B220 (clone RA3-6B2), CD19 (clone 1D3), CD4 (clone H129.19), CD8α (clone 53.6.7), Ly6c (clone AL-21), CD45RA (clone H1100), MHC class II (anti-1-$A^b$, Clone 25-9-17), CD80 (clone 16-10A1), CD86 (clone GL1), H-$2K^b$(clone AF6-88.5), CD123 (clone 5B11), and CD135/FLT3 (clone A2F10.1). Anti-mouse CCR6 (clone 140706) was from R&D Systems (Minneapolis, Minn.). Anti-clonotypic antibody Ti98 against the BM3 TCR was biotinylated and used as described (Tarazona et al., Int. Immunol., 1996; 8:351). All antibodies were used with isotype-matched negative controls.

To adjust for differences in nonspecific binding between cell populations, each isotype control was gated on the specific population of interest. Analytical flow cytometry was also performed on a 4-color FACS-Caliber (Becton-Dickinson) with similar results.

T cell activation in MLR. BM3 responder T cells were prepared from spleen by nylon-wool enrichment. Stimulators (sorted DCs or unfractionated TDLN) were mixed with $1\times10^5$ BM3 responder cells in 200 ul IMDM at the ratios shown in each figure. After 3 days, proliferation was measured by 4-hour thymidine incorporation assay. Where indicated, replicate groups of wells received 200 uM 1-methyl-[D]-tryptophan (Sigma-Aldrich, St. Louis, Mo.) or 250 uM [L]-tryptophan (Sigma). To prepare a 100× 1 MT stock, a 20 mM solution was dissolved in 0.1 N NaOH and then adjusted to pH 7.4. All MLRs were performed in V-bottom culture wells (Nalge-Nunc, Rochester, N.Y.), as previously described in Example 1, because the close cell-cell contact gave the maximum sensitivity to IDO-mediated suppression.

In these studies, it was important that the stimulator DCs not be irradiated, because initial validation studies showed that irradiation significantly altered the viability and functional attributes of $IDO^+$ pDCs. MLRs were thus "two-way" reactions. However, the small number of sorted DCs used as stimulators contributed negligible proliferation compared to the large population of TCR-transgenic responder cells. Since the relevant readout was dominant suppression, the two-way MLR design presented no problem in interpretation.

Quantitative real-time PCR. Total RNA was extracted from sorted cells using Trizol (Gibco-BRL, Gaithersburg, Md.). RNA was reverse-transcribed and amplified using the Light-Cycler real-time PCR system (Roche, Pleasanton, Calif.) with the RNA SYBR Green kit (Roche). All groups were compared in the same run, and quantitated against a standard curve of spleen RNA. Primers for mouse γ-actin were as follows. Sense was GATGACGCAGATAATGTTT (SEQ ID NO:2) and antisense was TCTCCTTTATGTCACGAAC (SEQ ID NO:3), yielding a 290 basepair product. Primers for mouse CD19 were as follows. Sense was GGCACCTATTATTGTCTCCG (SEQ ID NO:4) and antisense was GGGTCAGTCATTCGCTTC (SEQ ID NO:5), yielding a 218 basepair product). The primers for mouse pax5 were as follows. Sense was GCATAGTGTCTACAGGCTCCG (SEQ ID NO:6) and antisense was GATGGGTTCCGTGGTGGT (SEQ ID NO:7), yielding a 299 basepair product. Conditions were optimized for each set of primers to give a linear standard curve over a 1000-fold range, with a correlation coefficient of r greater than 0.99. An aliquot of each experimental sample was pre-screened to determine γ-actin message, then each sample was loaded to amplify an equivalent amount of γ-actin. For gels, RT-PCR was performed for the pre-determined optimum number of cycles yielding amplification in the linear range, and products resolved by formaldehyde gel electrophoresis. All primers gave single bands of the expected molecular weight.

Adoptive transfer studies. Recipient CBA mice (Jackson) were prepared by intravenous injection of $4\times10^7$ BM3 splenocytes (termed CBA+BM3 mice). It has been previously shown that adoptively transferred BM3 T cells are stable in CBA hosts for over 100 days (Tarazona et al., Int. Immunol., 1996; 8:351). CD11c+ DCs were isolated from TDLNs, or from normal LNs of C57BL/6 and CBA mice, using a Cytomation MoFlo high-speed cell sorter. Two aliquots of $1\times10^5$ DCs were injected into each recipient, subcutaneously in each anteriomedial thigh (analogous to the position of the original tumor). After 10 to 12 days, recipient mice were euthanized and the inguinal LNs (draining the sites of injection) and spleen (a representative distant site) removed for analysis. In some experiments, mice received 1-methyl-[D]-tryptophan (compound designation NSC 721782, Drug Development Group, Division of Cancer Treatment and Diagnosis, National Cancer Institute, Rockville, Md.) by continuous subcutaneous infusion (5 mg/day) using implantable copolymer pellets as previously described (Munn et al., *Science*, 1998; 281:1191). Control mice received vehicle pellets alone.

IDO-Expressing Cells in Human TDLNs Predict a Poor Clinical Outcome

Screening studies of radiographically mapped tumor-draining (sentinel) lymph nodes from patients with breast carcinoma and malignant melanoma demonstrated that a subset of patients had abnormal accumulation of cells expressing IDO in sentinel nodes. Similar cells were also seen in regional LNs dissections from other solid tumors (colon, lung and pancreas, not shown). Melanoma was chosen for further analysis because of the availability of archived sentinel LNs with paired long-term clinical follow-up. In a retrospective study of 40 patients with malignant melanoma, the presence of an abnormal number of IDO$^+$ cells in the sentinel LN at the time of diagnosis was found to be a significantly adverse prognostic factor. None of these patients had detectable metastases at the time of the biopsy, so recruitment of IDO$^+$ cells occurred early in the course of the disease. In this example, a murine system to model these cells was developed and used to determine that the IDO-expressing cells in TDLNs represented a population of immunoregulatory APCs.

IDO-expressing Cells in Murine TDLNs

The presence of IDO$^+$ cells in TDLNs of mice with Lewis Lung Carcinoma has been previously reported (Friberg et al., *Int. J. Cancer*, 2002; 101:151). With the present example, IDO$^+$ cells were also found in TDLNs in the well-characterized B16F10 melanoma model. LNs were harvested 7-12 days after tumor implantation, well before any detectable metastases to the LNs. The accumulation of IDO$^+$ cells occurred only in LNs draining the tumors; few or none were present in contralateral (non-tumor-draining) LNs from the same animals. Morphologically, the IDO$^+$ cells were plasmacytoid mononuclear cells similar to those found in human nodes. However, the number of such cells recruited by B16F10 tumors was lower than observed in heavily-infiltrated human LNs. To increase the number of APCs in the draining LNs, a subline of B16 melanoma (clone B78H1) transfected with the cytokine GM-CSF (Huang et al., *Science*, 1994; 264:961) was also stained for IDO expression. GM-CSF markedly increases the number of APCs recruited into TDLNs (Dranoff et al., *Proc. Natl. Acad. Sci. USA*, 1993; 90:3539), and many primary human melanomas and other tumors constitutively express mRNA for GM-CSF (Mattei et al., *Int. J. Cancer*, 1994; 56:853; Smith et al., *Clin. Exp. Metastasis*, 1998; 16:655; Colasante et al., *Hum. Pathol.*, 1995; 26:866; and Bronte et al., *J. Immunol.*, 1999; 162: 5728). B78H1•GM-CSF tumors recruited large number of IDO-expressing cells, comparable to heavily infiltrated humans LNs. As in B16F10, IDO expression was localized to the draining node, and was not observed in contralateral nodes from the same mice, nor in systemic sites such as spleen. Subsequent experiments therefore used TDLNs from mice with B78H1•GM-CSF tumors TDLNs Contain a Population of Suppressive Plasmacytoid DCs Single-cell suspensions of TDLNs, or the paired contralateral LNs, were used as stimulator cells in mixed leukocyte reactions (MLRs). The responder cells in MLRs were TCR-transgenic CD8$^+$ T cells from BM3 mice, which recognize a nominal antigen (H-2K$^b$) constitutively expressed by all APCs from the C57BL/6 tumor-bearing hosts (Tarazona et al., *Int. Immunol.*, 1996; 8:351). Preliminary validation studies confirmed that expression of the target antigen was high and comparable in DCs from TDLNs and normal LNs. FIG. 5A shows that cells from TDLNs were poor stimulators of BM3 T cells, whereas cells from the contralateral (non-tumor-draining) LNs of the same animals were excellent stimulators (comparable to LN cells from non-tumor-bearing mice, not shown). Mixing experiments (FIG. 5A, right panel) revealed that the failure of responder cells to proliferate in response to TDLN cells was due to a dominant suppressor activity present in the TDLN cells.

Sorting experiments (FIG. 5B) revealed that a suppressor activity was present in a CD25$^+$CD4$^+$ fraction (2-3% of total cells) corresponding to the Treg population known to be present in mice with B16 tumors (Sutmuller et al., *J. Exp. Med.*, 2001; 194:823). Further sorting revealed that a second, equally potent suppressor activity was also present in the CD11c$^+$B220$^+$ fraction (1-2% of total cells) comprising plasmacytoid DCs (pDCs). When these two suppressor populations were removed, the remaining 95-97% of TDLN cells stimulated excellent proliferation (as expected, since this fraction included all DCs other than pDCs, plus all B cells). Mixing experiments showed that suppression by pDCs was dominant, and was also quite potent, since the 1-2% of pDCs was able to suppress responses stimulated by all of the other APCs.

Immunosuppression by pDCs is Mediated by IDO

To test whether T cell suppression by pDCs was mediated by IDO, MLRs were performed in the presence or absence of the IDO inhibitor 1-methyl-tryptophan (1 MT). FIG. 5C shows that 1 MT blocked the suppressive activity of pDCs, converting them into effective stimulators of T cell proliferation, and reversing their dominant suppression in mixing experiments. This was not due to any nonspecific activating effects of 1 MT on T cells, because the same T cells stimulated by the non-suppressive "all other" fraction showed no enhancement by 1 MT.

To further confirm that suppression by pDCs was mediated via IDO, tumors were implanted in mice with a targeted disruption of the IDO gene (IDO-knockout mice). The pDCs isolated from TDLNs in these mice showed no suppressor activity (FIG. 5C, right panel). Further confirming the specificity of 1 MT for IDO, 1 MT had no effect on MLRs stimulated by IDO-deficient pDCs.

Finally, the suppressive effect of pDCs was abrogated by adding supraphysiologic, ten fold increased (10×), levels of L-tryptophan to the MLR (FIG. 5D). This prevents IDO from depleting tryptophan, via simple substrate excess, rather than by enzyme inhibition as with 1 MT, and circumvents IDO-mediated suppression of T cells (Munn et al., *J. Exp. Med.*, 1999; 189:1363). Excess L-tryptophan abrogated suppressor activity in a fashion similar to 1 MT. Also as with 1 MT, there was no effect of 10× L-tryptophan when pDCs were derived from IDO-KO hosts (FIG. 5D, right panel).

Adoptive Transfer of DCs from TDLNs Creates Immunologic Unresponsiveness In Vivo Next, whether the DCs from TDLNs were sufficient to create immunologic unresponsiveness in vivo, independent of the original tumor, was addressed. CD11c$^+$ DCs were isolated from TDLNs and adoptively transferred to new hosts. For these experiments, all of the DCs from TDLNs were used, not just the pDCs, in order to accurately reflect the mixed population found in TDLNs, and to ask whether stimulation of suppression would predominate in vivo. Ten days after adoptive transfer, T cells in the recipient host were tested for responsiveness to a nominal antigen (H-2K$^b$) presented by the transferred DCs. Recipients were allogeneic (H-2K$^b$-negative) CBA mice that had been pre-loaded with a large cohort of H-2K$^b$-specific BM3 T cells.

FIG. 6A shows that adoptively transferred DCs induced selective accumulation of antigen-specific BM3 T cells in inguinal LNs of recipient mice. This accumulation was comparable whether DCs were derived from TDLNs or from normal C57BL/6 LNs (both of which expressed H-2K$^b$). In contrast, DCs from antigen-negative CBA mice caused no such accumulation. In all groups, the number of BM3 T cells in the spleens (a site where BM3 T cells passively accumulate after injection) was similar, indicating that the initial loading was comparable.

Inguinal LN cells from recipient mice were assayed for functional responsiveness using MLRs stimulated by irradiated C57BL/6 (H-2K$^b$-positive) splenocytes. FIG. 6B shows that T cells from mice receiving TDLN DCs displayed profound hyporesponsiveness to recall antigen stimulation, despite the presence of ample BM3 T cells (see, FIG. 6A). In contrast, T cells from control animals receiving normal C57BL/6 DCs (containing a comparable number of BM3 T cells) displayed a brisk MLR response. Mice receiving antigen-negative DCs also responded well in MLRs, confirming that the large cohort of pre-positioned transgenic BM3 cells allowed a vigorous ex vivo response without the need for any previous priming.

Figure 6C:
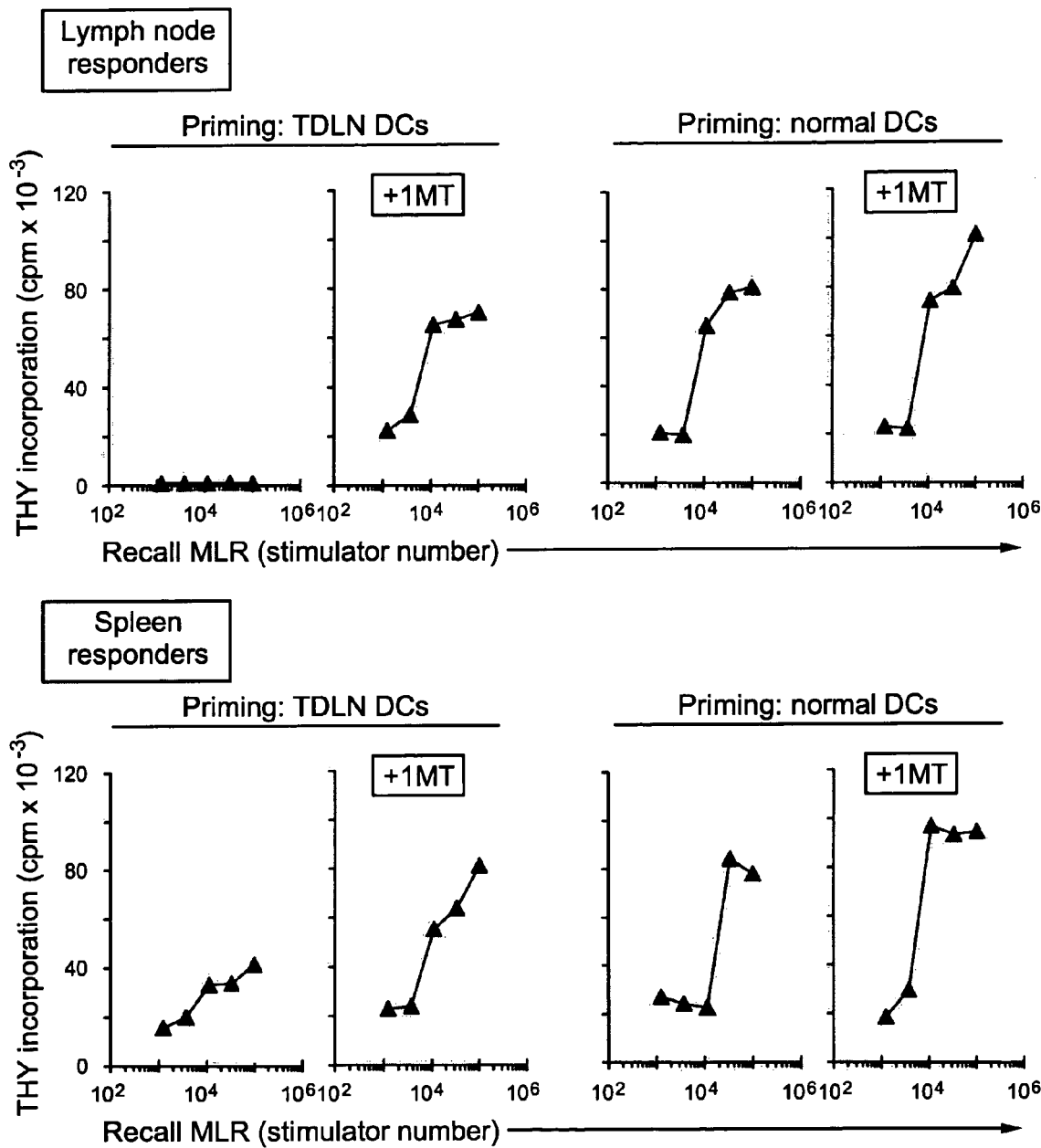

To test whether the state of acquired T cell unresponsiveness was created by IDO expression in the transferred TDLN DCs, recipient mice were treated with the IDO inhibitor 1 MT at the time of adoptive transfer (control mice received pellets without 1 MT). After 10 days, T cells were harvested and tested for responsiveness to antigen. Recall MLRs did not contain 1 MT. FIG. 6C shows that administration of 1 MT prevented the induction of T cell unresponsiveness in the recipients. The effect was specifically to block the acquisition of unresponsiveness, not simply to enhance T cell responses in general, since 1 MT had no enhancing effect on mice receiving normal DCs (right-hand panels). In all experiments, flow cytometry confirmed that LNs from all groups contained comparable numbers of BM3 T cells, similar to FIG. 6A.

In the same experiments, the systemic response of T cells isolated from spleens were also tested (FIG. 6C, lower panels). T cells from this remote site showed a modest reduction in response compared to controls, which was prevented by 1 MT treatment, but T cells in the spleen retained significantly more responsiveness that T cells from draining LNs. Thus, unresponsiveness was most profound in the LNs directly draining the site of injection.

T cells in Spleen Become Aware of Antigen Introduced on IDO$^+$ DCs

Figure 7A:
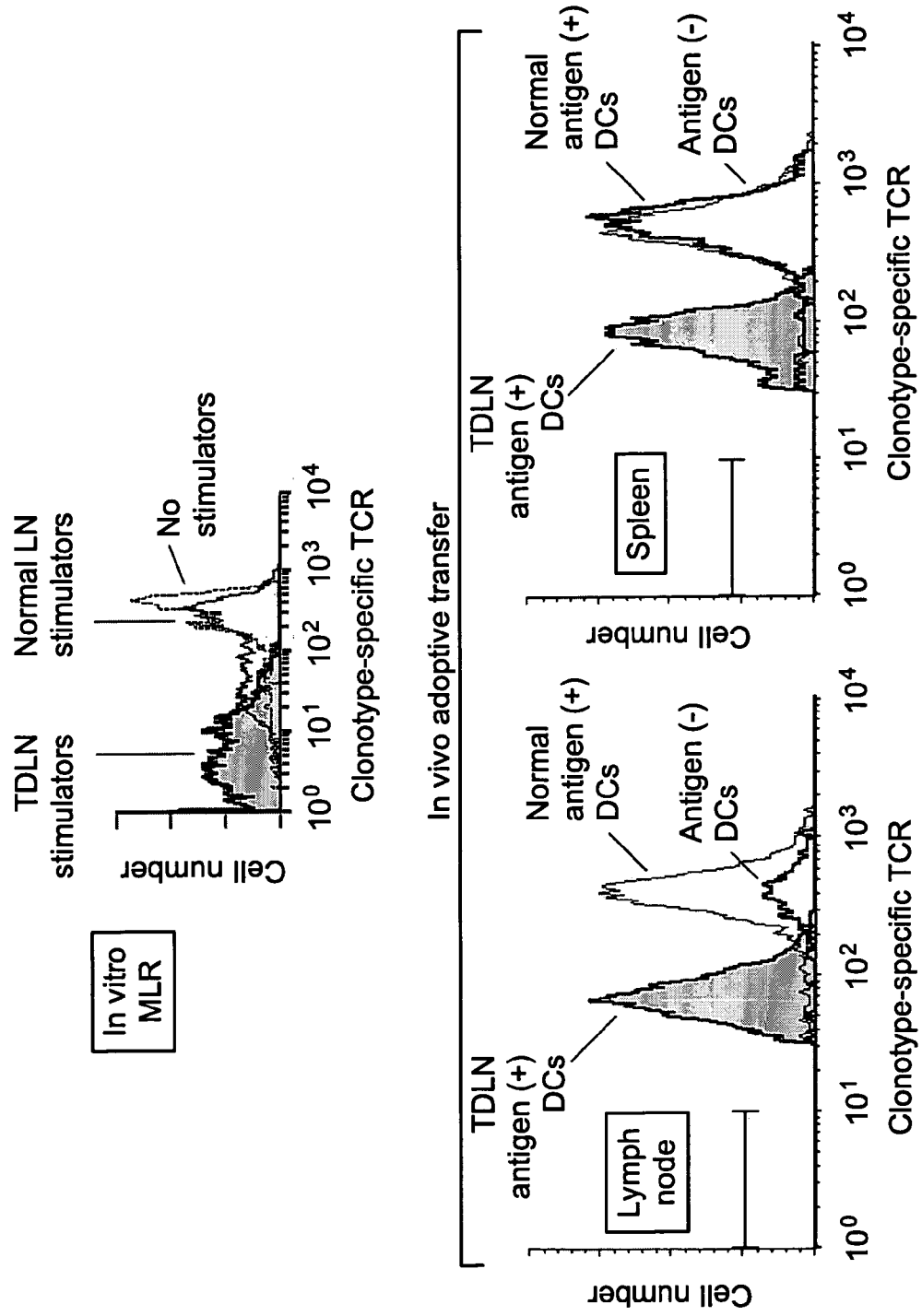

It was not clear whether T cells in the spleen became "aware" of antigens introduced on the transferred DCs. To address this question, the down regulation of clonotype-specific TCR on transgenic T cells was examined as a surrogate marker for antigen encounter (Tafuri et al., Science, 1995; 270:630). Although descriptive, this helps make the important distinction between true immunologic "ignorance" (no encounter with antigen) from encounter without activation. In vitro, it was found that BM3 T cells encountering antigen on TDLN cells showed a rapid and sustained down regulation of clonotype-specific TCR (FIG. 7A); in contrast, control BM3, stimulated by cells from normal LNs, retained TCR expression. Thus, sustained down regulation of TCR served as a marker for encounter with TDLN cells.

Applying this marker to adoptive transfer studies (FIG. 7A), it was found that BM3 T cells from hosts receiving TDLN DCs showed a uniform pattern of clonotype-specific TCR down regulation. In contrast, hosts receiving normal DCs showed no down regulation. This was observed in the LNs draining the site of adoptive transfer, but was equally present in spleens from the same animals. Thus, even at distant sites such as spleen, responding T cells were not truly "ignorant" of antigen, but had been affected the adoptively-transferred DCs (even though the affected cells were not anergic); and this effect was specific for TDLN DCs compared to normal DCs. When TDLN DCs were derived from IDO-knockout mice, there was little TCR down regulation following adoptive transfer (FIG. 7B), suggesting that most of the down regulation was mechanistically due to IDO expression by the TDLN DCs. A similar effect was seen when 1 MT was administered following adoptive transfer, also supporting the role of IDO. IDO-deficient TDLN DCs also did not create functional T cell unresponsiveness in the recipients (FIG. 7B, right panel), similar to recipient mice treated with 1 MT (FIG. 6C).

IDO$^+$ DCs Create Secondary Suppressor Mechanisms that are Independent of IDO

Next, it was addressed whether the T cell unresponsiveness created by adoptive transfer was due to intrinsic anergy of the responding T cells, or to some form of active suppression. Mixing experiments were performed using two groups of responder cells. One group of responder cells was control T cells isolated from CBA+BM3 recipients following adoptive transfer of normal DCs (fully responsive); and the second group of responder cells was T cells from the same mice following adoptive transfer of TDLN DCs (unresponsive). Mixing experiments (FIG. 7C) showed that the "unresponsive" cells entirely suppressed proliferation by the otherwise competent population (FIG. 7C, arrow). This was thus not consistent with simple anergy on the part of the unresponsive cells, but instead indicated a component of active, dominant suppression.

To test whether this suppression was mediated by IDO, recall MLRs were performed in the presence or absence of 1 MT. FIG. 7C (right panel) shows that 1 MT had no effect on suppression in recall MLRs, implying that IDO was not the mechanism of suppression. Thus, while the creation of unresponsiveness was absolutely dependent on IDO during its induction phase (FIGS. 6C and 7B), the unresponsive state was maintained, at least in part, by additional, IDO-independent mechanisms.

IDO-Mediated Suppression Segregates with a Small Subset of CD19$^+$ DCs

The preceding studies showed that some IDO-expressing cell type in TDLNs was responsible for creating immunologic unresponsiveness in vivo. To better define the specific DC subset, more detailed sorting experiments were performed. The experiments in FIG. 5 had shown that IDO-mediated suppressor activity segregated with the plasmacytoid (B220$^+$) DC fraction. Further phenotyping studies of this population showed it to be heterogeneous with respect to a number of markers, in particular expression of CD19. DCs from TDLN cells were sorted into CD19$^+$ and CD19$^{NEG}$ fractions of pDCs, as well as conventional B220$^{NEG}$ DCs, following the schema shown in FIG. 8. Immunohistochemistry on the sorted cells revealed that all three populations contained at least some cells with immunoreactive IDO. To quantitatively measure the IDO-mediated suppressor activity associated with each subset, the fractions were analyzed as stimulators in MLRs with and without 1 MT. Control MLRs received B cells from the same sorting run, which were good stimulators with no suppressor activity. FIG. 8 shows that virtually all of the IDO-mediated suppressor activity segregated with the novel CD19$^+$ DC fraction. When these CD19$^+$ DCs were removed, the remaining DCs showed minimal suppression (FIGS. 8B and 8C).

Despite comprising almost all of the IDO-mediated suppression, CD19$^+$ pDCs were a small fraction of total LN cells. In a total of 13 experiments (analyzing 2-6 pooled TDLNs each), the total CD11c$^+$ DCs were found to comprise 1-1.5% of cells. Of these, CD19$^+$ pDCs comprised 31±15% of DCs. Thus, the potent IDO-induced suppression seen in FIG. 5B, capable of dominantly inhibiting the proliferation stimulated by all of the other nonsuppressive DCs and B cells in mixing experiments, was mediated by 0.3-0.5% of total LN cells.

CD19$^+$ DCs Show a Phenotype of Mature Plasmacytoid DCs

Figure 9A:
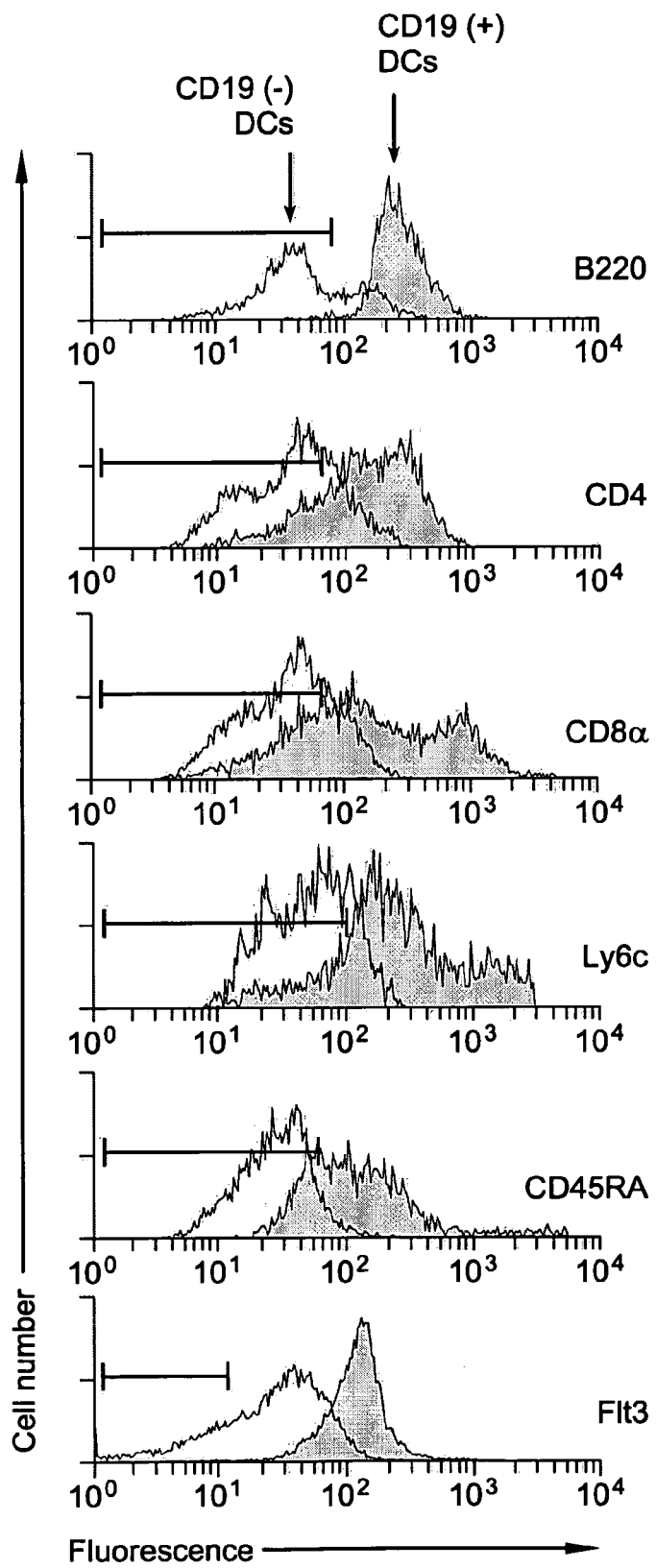
FIGS. 9A-9D. The CD19$^+$ DC subset displayed a phenotype consistent with mature plasmacytoid DCs.

FIG. 9A shows immunophenotyping of cells from TDLNs, gated first on the CD11c$^+$ DCs, then further gated into CD19$^+$ and CD19$^{NEG}$ fraction. Other markers (including B220) were analyzed in the third and fourth colors. FIG. 9A shows that all of the CD19$^+$ DCs in TDLNs expressed B220, consistent with their being a subset of pDCs (although not all of the B220$^+$ pDCs expressed CD19). Many of the CD19$^+$ DCs also expressed CD4 and/or CD8a, both of which can be found on pDCs (and both of which served to unambiguously distinguish CD19$^+$ pDCs from B cells). Many of the CD19$^+$ DCs also expressed Ly6c and CD45RA, which are markers associated with murine plasmacytoid DCs (O'Keeffe et al., *J. Exp. Med.*, 2002; 196:1307; and Martin et al., *Blood*, 2002; 100: 383). CD19$^+$ DCs also uniformly expressed the receptor tyrosine kinase Flt3 (CD135), which is expressed on DCs but not on mature B cells (Karsunky et al., *J. Exp. Med.*, 2003; 198:305).

Figure 9B:
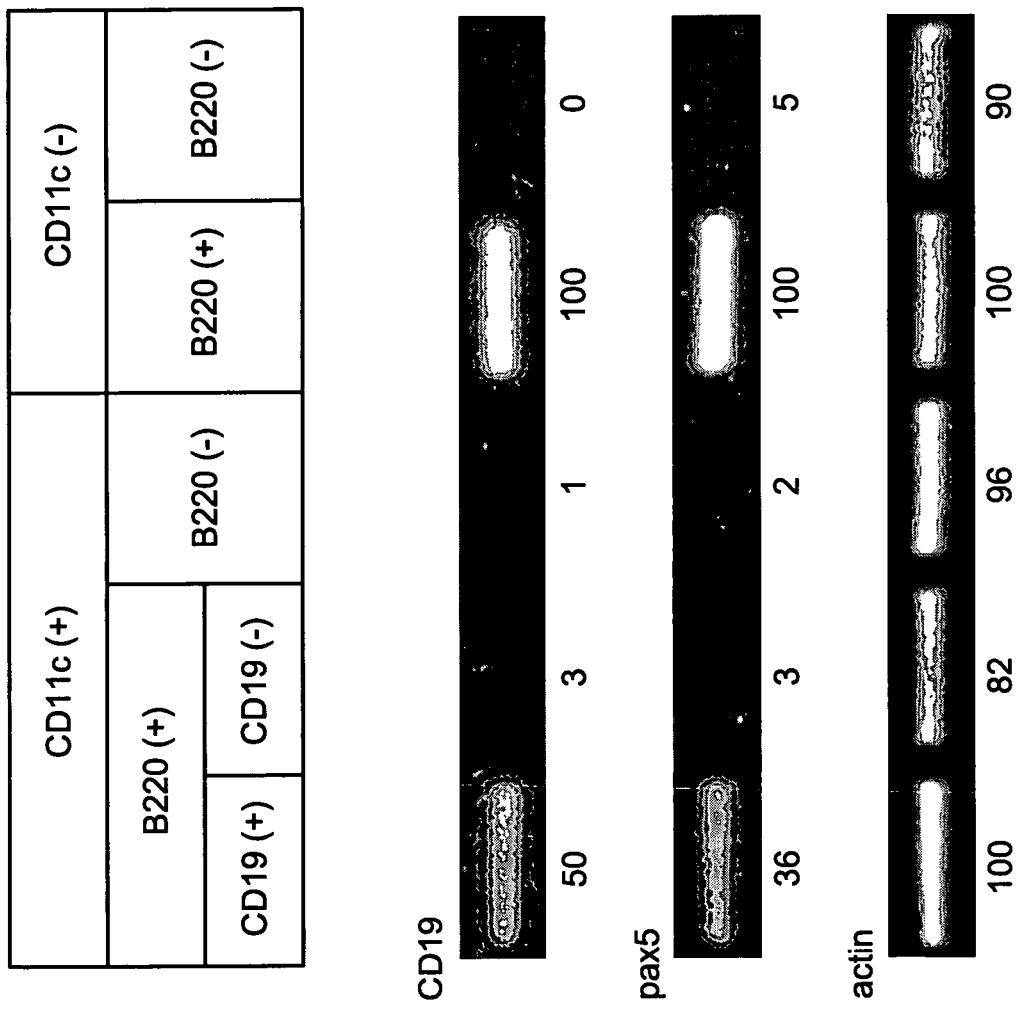

To confirm that the apparent expression of CD19 was authentic, mRNA for CD19 was measured by quantitative RT-PCR. The upstream transcription factor pax5 was also measured, since expression of CD19 is obligately dependent on expression of pax5 (Nutt et al., *EMBO J.*, 1998; 17:2319; and Mikkola et al., *Science*, 2002; 297:110). FIG. 9B confirms that cells of the CD19$^+$ pDC fraction expressed mRNA for both CD19 and pax5. Quantitatively, these genes were present at somewhat lower levels than in mature B cells (normalized to γ-actin), but they were expressed at much higher levels than in either the CD19$^{NEG}$ fraction of pDCs, or the B220$^{NEG}$ conventional DCs, and were thus unambiguously positive.

In other experiments CD19$^+$ pDCs of the same phenotype (CD11c$^+$CD19$^+$, B220$^+$, Ly6c$^+$, CD45RA$^+$) were also found in normal LNs from non-tumor-bearing hosts, as well as in the contralateral LNs of mice with B78H1•GM-CSF tumors, and in TDLNs from mice with B16F10 tumors. In the normal LNs they comprised 18±6% of total DCs (n=6 experiments), compared to 31±15% of total DCs in B78H1•GM-CSF TDLNs.

Figure 9C:
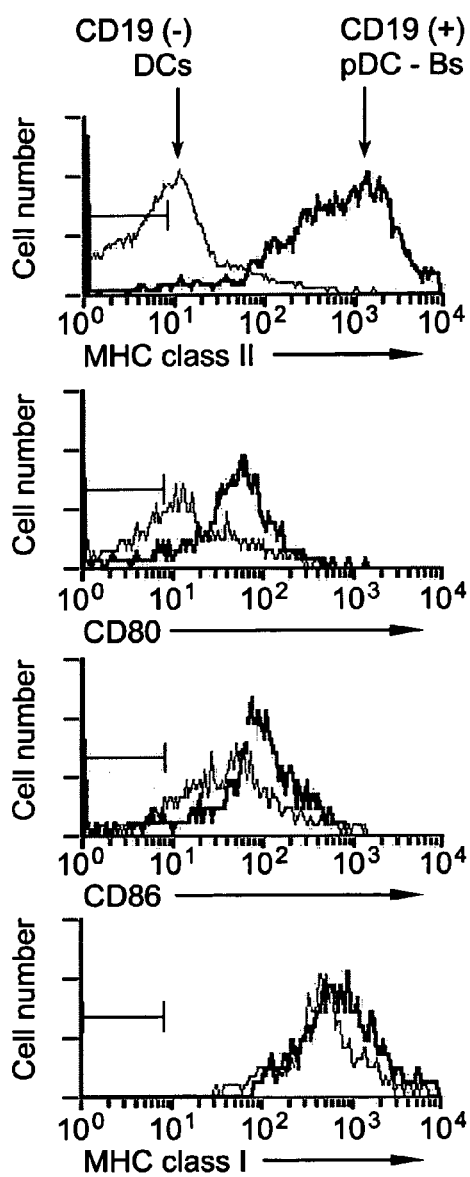

CD19$^+$ pDCs TDLNs uniformly expressed high levels of MHC class II molecules, and costimulatory molecules CD80 and CD86, suggestive of a mature phenotype (FIG. 9C). These were expressed at levels equal to or greater than the CD19$^{NEG}$ DCs from the same LN, many of which were immature, as shown. In different TDLNs, the CD19$^{NEG}$ subset of DCs showed significant variability in the number of mature versus immature DCs; however, all of the CD19$^+$ pDCs were invariably mature.

Figure 9D:
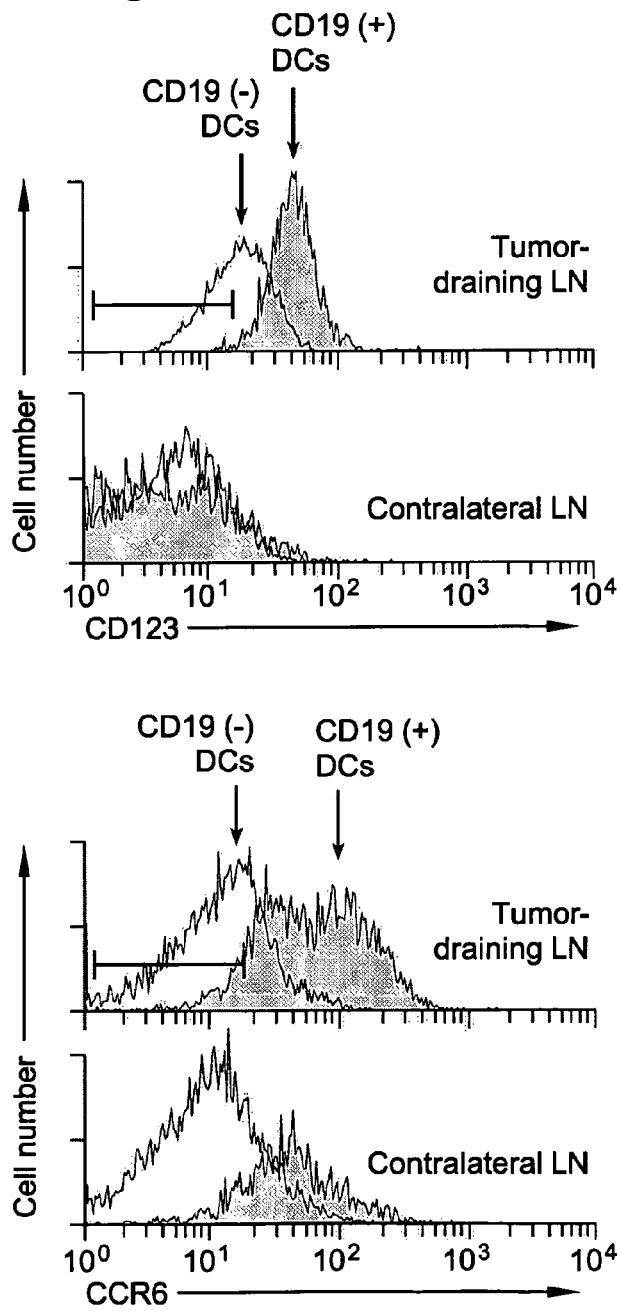

In addition to maturation markers, the CD19$^+$ pDCs also expressed two markers observed in the human system. As shown in Example 1, CD123 (IL3Ra) and the chemokine receptor CCR6 segregate closely with IDO expression in human monocyte-derived DCs and macrophages. In this example, it was found that in murine TDLNs, expression of CD123 and CCR6 preferentially associated with the CD19$^+$ subset of DCs in TDLNs (FIG. 9D). In contrast, the majority of CD19$^{NEG}$ DCs were low or negative for these markers (FIG. 9D), as were the majority of B cells, which were less than 20% positive for CCR6 and less than 2% positive for CD123.

Discussion

The current example identifies a small population of immunoregulatory DCs in TDLNs that are capable of mediating dominant immunosuppression in vitro, and creating profound immunologic unresponsiveness in vivo. Of the limited number of studies assessing DCs from TDLNs, most have reported a defect in their ability to stimulate T cells (Vicari et al., *J. Exp. Med.*, 2002; 196:541; Almand et al., *Clin. Cancer Res.*, 2000; 6:1755; and Yang et al., *J. Clin. Invest.*, 2003; 111:727). However, it has been unclear whether this was due to immaturity of the DCs, or to some form of active suppression. This example shows that one subset of DCs in TDLNs can create potent active suppression, mediated via the molecular mechanism of IDO.

The suppression created by IDO-expressing DCs was profound, but it was fundamentally local. First, the expression of IDO itself was strictly localized, being found in the LNs draining tumors, but not in other LNs from the same animal. Second, adoptive transfer of DCs from these nodes created complete T cell unresponsiveness in the new nodes draining the site of injection, while T cells in spleens of the same animals remained reactive. An analogous dichotomy has been observed in tumor-bearing hosts, where tumors may be locally tolerated despite the systemic presence of competent, tumor-specific T cells (Wick et al., *J. Exp. Med.*, 1997; 186: 229; Speiser et al., *J. Exp. Med.*, 1997; 186:645; and Nguyen et al., *J. Exp. Med.*, 2002; 195:423). The fact that tumors in this situation grow unchecked, ultimately killing their hosts, emphasizes the point that immunosuppression does not have to be systemic in order to be effective. Functionally, if all the draining LNs of all the sites of tumor create local unresponsiveness, the tumor is de facto tolerated.

In this regard, it is relevant to note that the immunosuppression created by IDO-expressing DCs was dominant. This was shown by in vitro mixing experiments, in which a small population of CD19$^+$ pDCs from TDLNs could completely suppress T cell responses, despite the presence of many other stimulatory APCs (for example, see FIG. 5). It remains to be elucidated how such a small population of IDO$^+$ DCs can effectively control a large T cell response, but this same phenomenon has been observed in other studies of IDO-expressing DCs (Grohmann et al., *J. Immunol.*, 2000; 165: 1357; and Mellor et al., *J. Immunol.*, 2003; 171:1652).

This example demonstrated that the adoptive transfer of TDLN DCs in vivo was able to create local immunologic unresponsiveness to a strong nominal antigen (H-2K$^b$), even in the presence of a large cohort of antigen-specific, TCR-transgenic T cells. This local effect was accompanied by a systemic effect on all transgenic T cells, as shown by sustained down regulation of TCR expression. It has been suggested that such TCR down regulation may serve as a marker for anergy (Benson et al., *J. Clin. Invest.*, 2000; 106:1031; and Tafuri et al., *Science*, 1995; 270:630), but anergy alone could not account for all of the immunosuppression created by the TDLN DCs. Mixing experiments revealed that there was also a potent component of active suppression, capable of inhibiting other, fully competent responder T cells in vitro (see FIG. 7C).

This secondary suppressor activity was not itself mediated by IDO, but it was obligately dependent on expression of functional IDO by TDLN DCs for its creation. Thus, the IDO expressed by TDLN DCs elicited a secondary mechanism to amplify and sustain its immunosuppressive effect.

These observations are consistent with findings in other studies using CD8a+ DCs from spleen, activated in vitro to express IDO. Adoptive transfer of even small numbers of such IDO-expressing DCs was capable of creating systemic unresponsiveness to antigen (Grohmann et al., *J. Immunol.*, 2000; 165:1357; and Fallarino et al., *Nat. Immunol.*, 2003; 4:1206-12).

In the present system, the immunosuppression mediated by IDO-expressing DCs was an active process, not merely a passive failure of immature DCs to stimulate T cells. It is well established that immature DCs can be tolerogenic (Hawiger et al., *J. Exp. Med.*, 2001; 194:769; and Probst et al., *Immunity*, 2003; 18:713), which has been attributed to their failure to provide adequate costimulation. However, it has been more controversial whether certain DCs may be tolerogenic even when mature (Moser, *Immunity*, 2003; 19:5). The CD19+ pDCs found in TDLNs appeared phenotypically mature (positive for CD80 and CD86, high MHC-II expression, and excellent stimulators of T cell proliferation when IDO was blocked). Despite this, they were also actively suppressive in vitro, as shown by mixing experiments. In order to clearly demonstrate the active nature of this suppression in vivo, the present adoptive transfer studies were designed so that vigorous T cell activation was the default response. A strong alloantigen (H-2K$^b$) was employed, constitutively expressed on all transferred DCs, recognized by a massive population of pre-positioned TCR-transgenic T cells (up to 40% of recipient CD8+ T cells). Because of this large "pre-expanded" clone of T cells, there was no need for any initial priming step in order to see a robust proliferative response in MLR assays. Even in this system, DCs from TDLNs were able to create acquired unresponsiveness to the H-2K$^b$ antigen, in an IDO-dependent fashion.

Fractionation studies of TDLN cells showed that virtually all of the IDO-mediated suppressor activity segregated with a novel population of CD19+ DCs. CD19, and its obligate transcription factor pax5, are markers of the B cell lineage (Fearon and Carroll, *Ann. Rev. Immunol.*, 2000; 18:393; and Nutt et al., *Nature*, 1999; 401:556), so expression of these genes suggests derivation from a B-lineage precursor (or a common lymphoid progenitor cell). Consistent with this possibility, it is known that early CD19+ pro-B cells can give rise to DCs in vitro (Bjorck and Kincade, *J. Immunol.*, 1998; 161:5795; and Izon et al., *J. Immunol.*, 2001; 167:1387). Recent analyses of both human and murine plasmacytoid DCs suggests a B-cell origin for a subset of pDCs (Rissoan et al., *Blood*, 2002; 100:3295; and Corcoran et al., *J. Immunol.*, 2003; 170:4926); in mice, up to one-third of DNA from murine splenic plasmacytoid DCs was found to show D-J rearrangement of the IgH locus (Corcoran et al., *J. Immunol.*, 2003; 170:4926). Despite this link, previous studies have failed to identify the CD19+ subset of pDCs. In part, this may be because many studies have specifically excluded the CD19+ cells, either by depletion or by back-gating (O'Keeffe et al., *J. Exp. Med.*, 2002; 196:1307; and Asselin-Paturel et al., *Nat. Immunol.*, 2001; 2:1144). Even if recognized as DCs, it would not be obvious that the CD19+ cells were tolerogenic, because resting CD19+ DCs do not constitutively express IDO, and are not suppressive. It was only in the context of TDLNs that the regulatory attributes of these cells became evident.

The key difference between TDLNs and normal LNs was not the presence or absence of CD19+ DCs, as they were present in both, although at higher numbers in the TDLNs, but rather the fact that CD19+ DCs from TDLNs constitutively expressed IDO. It has been previously shown that the IDO-inducing agent CTLA4-Ig up regulates IDO preferentially in the B220+ and CD8a+ DC subsets (Mellor et al., *J. Immunol.*, 2003; 171:1652). Prior to CTLA4-Ig treatment, these DCs were not inhibitory, but they became so after IDO was induced (Mellor et al., *J. Immunol.*, 2003; 171:1652), indicating that some factor in TDLNs acts to induce constitutive expression of IDO in CD19+ pDCs. This factor might be a microenvironmental signal, such as a cytokine, found selectively in TDLNs. Alternatively, it has recently been shown that CD25+ CD4+ Tregs can induce IDO in DCs via expression of CTLA4 (Fallarino et al., *Nat. Immunol.*, 2003; 4:1206-12). Thus, it is possible that TDLNs might contain a population of Tregs that triggers IDO. Elucidating the upstream factors responsible for the constitutive induction of IDO in TDLNs may offer significant insight into how tumors evolve to exploit the IDO mechanism.

Example 3

1-Methyl-[D]-Tryptophan, a Novel, Small-Molecule, Orally-Bioavailable Immune Modulator for Use in Cancer Immunotherapy Tumors actively create a state of tolerance toward their own antigens. This pathologic situation allows the tumors to escape from host immune surveillance and also imposes a barrier to effective anti-tumor immunotherapy. One molecular mechanism by which tumors may inhibit immune responses is via the immunosuppressive enzyme indoleamine 2,3-dioxygenase (IDO). IDO degrades the amino acid tryptophan, and this acts to inhibit T cell responses. The small-molecule 1-methyl-D-tryptophan (1 MT) acts as an inhibitor of IDO enzyme activity in vitro, and is capable of preventing IDO-mediated immunosuppression in vivo. 1 MT thus acts as an immune-enhancing agent in a variety of animal models where IDO limits or suppresses immunologic responses. In this example, administration of 1 MT to tumor-bearing hosts in conjunction with low-dose chemotherapy or radiation shows synergistic immune-mediated anti-tumor effect. 1 MT thus represents a novel small-molecule, orally-bioavailable immune modulator for use in cancer immunotherapy.

1 MT targets a previously unrecognized immunosuppressive pathway. This endogenous pathway may limit the efficacy of current immunotherapy approaches. One application of 1 MT is as a vaccine adjuvant, since anti-tumor vaccines have shown occasional encouraging responses but their overall response rates remain limited (Yu and Restifo, *Journal of Clinical Investigation* 2002; 110:289-294). Thus, adding 1 MT as an adjuvant to an existing (Phase 11) anti-tumor vaccine would be ethical and appropriate. Further, it is likely unnecessary to supply exogenous tumor antigen in the form of a vaccine. Chemotherapy and radiation already release large amounts of antigen from dying tumor cells, but these do not normally generate a useful immune response. 1 MT will allow immune responses to such antigens.

Comparison of D- Versus L-isomers of 1 MT

Figure 10:
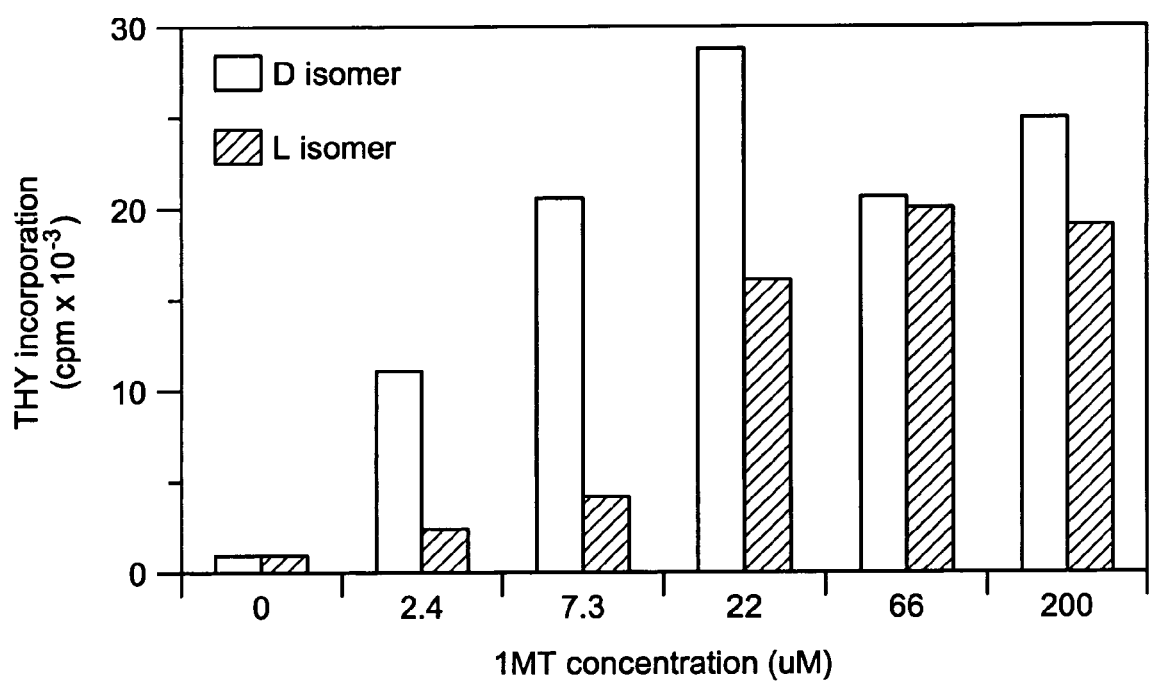
FIG. 10. Superior inhibitory activity of the D isomer of 1 MT in an in vitro bioassay. The ability of D- and L-1 MT to inhibit IDO-mediated suppression of human T cell proliferation was measured in allogeneic MLRs, using enriched IDO-expressing human DCs. Replicate MLRs received each compound at the concentrations shown. Bars represent T cell proliferation at the end of the 5-day activation period.

Cultured human dendritic cells (DCs) enriched for IDO expression were prepared as described by Munn et al., *Sci-* ence 2002; 297:1867-1870. DCs were used as stimulators in allogeneic mixed-leukocyte reactions (MLRs), with allogeneic lymphocytes as responder cells. The ability of 1 MT to inhibit IDO-mediated suppression is measured as the amount of T cell proliferation. FIG. 10 shows that the D isomer was significantly more effective than the L isomer at reversing IDO-mediated suppression.

IDO-expressing Cells in Human Tumor-Draining Lymph Nodes

Using a polyclonal antibody against human IDO, abnormal accumulation of IDO+ cells was seen in many tumor-draining (sentinel) lymph nodes from patients with malignant melanoma (Example 2 and as described in Lee et al., *Laboratory Investigation* 2003; 83:1457-1466). A retrospective analysis of sentinel nodes from 40 patients with locally-confined disease at diagnosis showed the presence of these IDO+ cells was an adverse prognostic factor, even prior to detectable metastasis.

IDO+ Cells are Selectively Recruited into Mouse Tumor-Draining Lymph Nodes

Tumor-draining lymph nodes from C57BL/6 mice implanted with B16F10 melanoma cells (day 14) showed significant accumulation of IDO+ cells compared contralateral lymph nodes from the same animals. Phenotypically, the IDO+ cells were mostly CD11c+B220+ "plasmacytoid" dendritic cells. To obtain larger lymph nodes for functional studies, B78H1.GMCSF, a GMCSF-transfected sub-line of B16 was also used (Huang et al., *Science* 1994; 264:961-965; and Borrello et al., *Human Gene Therapy* 1999; 10:1983-1991). These tumors recruited the same IDO+ cells, but yielded quantitatively more cells for study. GMCSF-transfected cell lines recruit large numbers of DCs (Dranoff, *Immunological Reviews* 2002; 188:147-154), but as viable tumors they have been found to induce tolerance instead of spontaneous immunity (Bronte et al., *J. Immunol.* 1999; 162:5728-5737).

IDO-Mediated Suppression Segregates with the Plasmacytoid DCs

FIG. 5 shows IDO-expressing suppressive APCs are present in tumor-draining LNs. Pooled draining LN cells (4 nodes) were stained and fractionated by 4-color MoFlo cell sorting for the two populations shown in the schematic of FIG. 5B. All other cells were collected in a third fraction. Each fraction was then used as stimulators in MLRs, using 50,000 BM3 T cells as responders. The number of stimulators used in each MLR was adjusted to be the same as would have been present in 50,000 cells of the original LN preparation, based on the measured percentage of each sorted fraction. Thus, 500 cells of the sorted B220+ CD11c+ fraction were added per well, and 1500 cells of the CD25+ CD4+ fraction, while 48,000 cells of the "all other" fraction were used. Replicate MLRs were performed with or without 1 MT, as shown. Tumor-draining LN cells from a wild-type (IDO-sufficient) C57BL/6 host and tumor-draining LN cells from an IDO-knockout host, showing no IDO-mediated inhibition (but with inhibition by Tregs intact) are shown in FIGS. 5C and 5D. The arrows in FIG. 5C indicate the IDO-mediated (1 MT-sensitive) component of inhibition.

Cells were harvested from tumor-draining lymph nodes (day 12) and used as APCs in allogeneic mixed-leukocyte reactions (MLRs). Responder T cells were taken from "BM3" TCR-transgenic mice (CD8+, recognizing H-2K$^b$ (Tarazona et al., *International Immunology* 1996; 8:351-358)). Cells were sorted into B220+ CD11c+ plasmacytoid DCs, and a separate CD25+CD4+ fraction of regulatory T cells. It was important to separate out these Tregs, otherwise they would nonspecifically inhibit proliferation in the readout MLRs. The third fraction collected comprised the remaining 96% of the lymph-node cells; these cells stimulated good T cell proliferation, and there was no enhancement by 1 MT (thus confirming that 1 MT had no nonspecific stimulatory effect in the absence of IDO). The plasmacytoid DC fraction was potently inhibitory, and this was fully reversed by 1 MT. Mice with a targeted deletion of IDO were as described in Mellor et al., *J. Immunol.* 2003; 171:1652-1655 9. These IDO-knockout mice showed no suppressor activity by plasmacytoid DCs, and no effect of 1 MT, thus confirming that the molecular target of 1 MT was indeed IDO.

Effect of 1 MT on Established Tumors, and Synergy with Radiation or Cyclophosphamide B16F10 melanomas were implanted in C57BL/6 mice, then 7 days later mice were treated with 1 MT or vehicle control (administered by SQ continuous infusion using implantable co-polymer pellets (Munn et al., *Science* 1998; 281:1191-1193)). The initial studies used the DL racemic form of 1 MT, at a total dose of 20 mg per mouse per day. In this established-tumor model, 1 MT alone had no effect. Not unexpected, given that the tumor had already been allowed to create tolerance in the host. However, when the established host/tumor milieu was transiently perturbed by a single dose of total-body radiation (500 cGy) or cyclophosphamide (150 mg/kg×1 dose), 1 MT acted synergistically with both interventions, to significantly reduce tumor growth (FIGS. 11A and 11B). Although the combination was not curative, this degree of growth delay was comparable to that seen with other immunologic interventions in this aggressive tumor model (van Elsas et al., *J Exp Med* 1999; 190(3):355-66; and Kotera et al., *Cancer Research* 2001; 61(22):8105-8109). Identical experiments performed in immunodeficient (RAG1-knockout) hosts showed no enhancing effect of 1 MT over cyclophosphamide alone (FIG. 11C), indicating that the effect of 1 MT was entirely immunologically mediated. Finally, the [D]-isomer of 1 MT was found to be effective at one quarter the dose used for the racemic preparation (FIG. 11D).

The radiation studies shown in FIG. 11A were replicated using a similar experimental design. The pattern of response observed in these studies was similar to that shown in FIG. 11A, with 1 MT alone having no effect, but with the combination of the [D]-isomer of 1 MT and radiation showing enhanced effect over radiation alone.

Pharmacokinetics

Comparative pharmacokinetic studies were initiated to characterize the in vivo disposition of the stereoisomers of 1-MT when administered by different routes, to determine the oral bioavailability, and to define the plasma concentrations associated with effective dosing regimens. Studies were conducted in conventional mice after IV, PO and SC doses of 50 mg/kg, and IP doses of 25 mg/kg, 50 mg/kg, and 100 mg/kg. In addition, plasma concentrations of 1-MT were determined in nude mice with implanted timed-release pellets designed to release the DL isomer for 7 days, and the D isomer for 14 days.

Peak plasma concentrations of D or L 1-MT were attained 2 hours after PO administration. The maximum concentration observed for the L isomer was approximately seven times greater than that for the D isomer. The AUC0-∞ for the L isomer was also substantially greater (9 fold) than that for the D isomer. Terminal disposition phase half-lives were similar for the two isomers, and also similar to those found after IV administration. The oral bioavailability for D and L 1-MT were 64% and 105%, respectively.

The in vivo disposition of the D and L isomers of 1-MT are remarkably different considering their nearly identical chemical structures. Analysis of their plasma pharmacokinetics suggests that the basis for the difference is a rapid partitioning of the D isomer into tissues compartments other than the plasma, while the L isomer is more predominantly distributed in the plasma. As a consequence, the AUC0-∞ observed for L 1-MT were from 5 to 9 times greater than those found for D 1-MT with equivalent routes of administration and doses. Given the comparatively lower plasma levels of the D isomer, while tempting to speculate regarding where the D isomer does reside, the experimental design of these studies did not encompass examination of the tissue or cellular distribution of 1-MT. However, one possible explanation to account for the relatively greater apparent volume of distribution of the D isomer is a higher intracellular localization, raising the possibility of a unique cellular transport mechanism for D 1-MT not shared by L1-MT. Cellular uptake studies will be performed with the two isomers to address this pivotal issue.

Both isomers were absorbed efficiently following IP, SC and PO administration, and the plasma pharmacokinetics were comparable regardless of the route of administration, indicating that any of the routes studied are equally suitable for efficacy testing. The oral bioavailability of the D isomer (64%) was somewhat lower than that observed when it was given by the intraperitoneal (IP) or subcutaneous (SC) route, and also lower than the oral bioavailability of L 1-MT.

Pilot Studies to Address the Tissue Biodistribution of the D-isomer

Mice were given 1 MT as the DL racemic mixture (10 mg/day, SQ implanted copolymer pellets, 72 hour infusion), then tissues were harvested, extracted, and tissue levels of the respective D and L isomers determined by generation of diastereomeric isoindoyl derivatives with OPA and Boc-L-Cys (Hashimoto et al., *J Chromatography* 1992; 582:41-48). Initial results showed at least equal, and possibly preferential, accumulation of the D isomer in liver, with equivalent distribution of D and L isomers into muscle and spleen. The results noted with spleen are particularly relevant because it is a lymphoid organ, and thus likely to be similar to tumor-draining lymph nodes. Initial results also showed lower levels of the D isomer in plasma and in brain, suggesting that the D isomer may not cross the blood-brain barrier efficiently. Thus, the lower plasma levels and shorter intravascular half-life do not necessarily imply lower levels in the relevant tissues.

Discussion

1-MT represents the lead compound in a new class of immunomodulatory agents, designed to block immunosuppression mediated by IDO. Many tumors, under the selection pressure of host immune surveillance, have evolved some means to exploit the tolerogenic activity of IDO, either directly, through expression of IDO by tumor cells, or by recruiting IDO-expressing APCs to induce systemic tolerance. Thus, 1 MT will be indicated as an immunologic adjuvant in combination with anti-tumor vaccines, including peptide, cell-lysate, or dendritic cell-based vaccines, and as an immunomodulatory agent in combination with chemotherapy or radiation. 1 MT is a lead compound, representative of a new class of immunomodulatory drugs designed to inhibit the IDO pathway. It is one of a number of small-molecule, orally-bioavailable immunostimulatory agents.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

SEQUENCE LISTING FREE TEXT

SEQ ID NO:1 peptide; human indoleamine-2,3-dioxygenase (IDO)
SEQ ID NO:2-7 Synthetic oligonucleotide primers

What is claimed is:

1. A method of treating a subject with cancer, the method comprising administering to the subject a pharmaceutical composition consisting essentially of 1-methyl-D-tryptophan, wherein said composition is administered before, during, or after at least one cytotoxic antineoplastic chemotherapeutic agent.

2. A method of treating a subject with cancer, the method comprising administering to the subject a pharmaceutical composition comprising 1-methyl-D-tryptophan, but not 1-methyl-L-tryptophan, wherein said composition is administered before, during, or after at least one cytotoxic antineoplastic chemotherapeutic agent.

3. A method of reducing tumor size or slowing tumor growth in a subject, the method comprising administering to the subject a pharmaceutical composition consisting essentially of 1-methyl-D-tryptophan, wherein said composition is administered before, during, or after at least one cytotoxic antineoplastic chemotherapeutic agent.

4. A method of reducing tumor size or slowing tumor growth in a subject, the method comprising administering to the subject a pharmaceutical composition comprising 1-methyl-D-tryptophan, but not 1-methyl-L-tryptophan, wherein the pharmaceutical composition is administered before, during, or after at least one cytotoxic antineoplastic chemotherapeutic agent.

5. The method of claim 1, 2, 3 or 4, wherein the antineoplastic chemotherapeutic agent is selected from the group consisting of: cyclophosphamide, methotrexate, fluorouracil, doxorubicin, vincristine, ifosfamide, cisplatin, gemcytabine, busulfan, and ara-C.

6. The method of claim 1, 2, 3 or 4 wherein the cancer is selected from the group consisting of melanoma, colon cancer, pancreatic cancer, breast cancer, prostate cancer, lung cancer, leukemia, brain tumors, lymphoma, sarcoma, ovarian cancer, Kaposi's sarcoma, Hodgkin's Disease, mutiple myeloma, neuroblastoma, stomach cancer, cervical cancer, endometrial cancer, testicular cancer, thyroid cancer, esophageal cancer, genitourinary tract cancer, premalignant skin lesions, and adrenal cortical cancer.

7. The method of claim 1, 2, 3, or 4 further comprising administering a cytokine.

8. The method of claim 7 wherein the cytokine is granulocyte macrophage colony stimulating factor (GM-CSF) or its flt3-ligand.

9. The method of claim 1, 2, 3, or 4 wherein the composition further comprises a pharmaceutically acceptable carrier.

10. The method of claim 1, 2, 3, or 4 wherein the composition is formulated for oral, rectal, nasal, topical, transdermal, aerosol, buccal, sublingual, vaginal, parenteral, subcutaneous, intramuscular, intravenous, intradermal, enteral, intraperitoneal, or intravesicular administration.

11. The method of claim 10, wherein the composition is formulated for oral delivery.

12. The method of claim 11 wherein the composition is formulated as a tablet or a capsule.

13. The method of claim 10, wherein the composition is formulated for a controlled or sustained release.

14. The method of claim 1, 2, 3, or 4 wherein the composition is formulated as an ointment, gel, solution, patch or implant.

15. The method of claim 1, 2, 3, or 4, wherein the composition further comprises one or more diluents, buffers, binders, disintegrants, surface active agents, thickeners, lubricants, or preservatives.

16. The method of claim 1, 2, 3, or 4 wherein the administration is carried out in a number of doses at intervals of time.

17. The method of claim 1, 2, 3, or 4, further comprising surgical resection, radiation therapy, chemotherapy, hormone therapy, anti-tumor vaccination, antibody based therapy, cytokine based therapy, whole body irradiation, bone marrow transplantation, and peripheral stem cell transplantation.

* * * * *

UNITED STATES PATENT AND TRADEMARK OFFICE
CERTIFICATE OF CORRECTION

PATENT NO.        : 7,598,287 B2  
APPLICATION NO.   : 10/780797  
DATED             : October 6, 2009  
INVENTOR(S)       : Munn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1218 days.

Signed and Sealed this

Twenty-eighth Day of September, 2010

David J. Kappos  
*Director of the United States Patent and Trademark Office*